US010071051B2

(12) United States Patent
Okubo et al.

(10) Patent No.: US 10,071,051 B2
(45) Date of Patent: *Sep. 11, 2018

(54) WT1 PEPTIDE CANCER VACCINE COMPOSITION FOR TRANSDERMAL ADMINISTRATION

(71) Applicants: NITTO DENKO CORPORATION, Osaka (JP); OSAKA UNIVERSITY, Osaka (JP)

(72) Inventors: Katsuyuki Okubo, Osaka (JP); Yoshiki Maeda, Osaka (JP); Arimichi Okazaki, Osaka (JP); Daisuke Asari, Osaka (JP); Takuya Shishido, Osaka (JP); Mitsuhiko Hori, Osaka (JP); Haruo Sugiyama, Osaka (JP)

(73) Assignees: NITTO DENKO CORPORATION, Osaka (JP); OSAKA UNIVERSITY, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/166,950

(22) Filed: Jan. 29, 2014

(65) Prior Publication Data

US 2014/0220057 A1 Aug. 7, 2014

(30) Foreign Application Priority Data

Feb. 5, 2013 (JP) ................................. 2013-020908

(51) Int. Cl.

| A61K 9/00 | (2006.01) |
|---|---|
| A61K 38/10 | (2006.01) |
| A61K 39/00 | (2006.01) |
| A61K 31/045 | (2006.01) |
| A61K 31/437 | (2006.01) |
| A61K 31/451 | (2006.01) |
| A61K 31/513 | (2006.01) |
| A61K 31/708 | (2006.01) |
| A61K 31/716 | (2006.01) |
| A61K 31/728 | (2006.01) |
| A61K 31/739 | (2006.01) |

(52) U.S. Cl.

CPC .......... *A61K 9/0014* (2013.01); *A61K 31/045* (2013.01); *A61K 31/437* (2013.01); *A61K 31/451* (2013.01); *A61K 31/513* (2013.01); *A61K 31/708* (2013.01); *A61K 31/716* (2013.01); *A61K 31/728* (2013.01); *A61K 31/739* (2013.01); *A61K 38/10* (2013.01); *A61K 39/0011* (2013.01); *A61K 2039/54* (2013.01)

(58) Field of Classification Search
None
See application file for complete search history.

(56) References Cited

U.S. PATENT DOCUMENTS

| 7,030,212 B1 | 4/2006 | Sugiyama et al. | |
|---|---|---|---|
| 2005/0215501 A1* | 9/2005 | Lipford et al. | 514/44 |
| 2007/0082860 A1 | 4/2007 | Sugiyama et al. | |
| 2008/0112974 A1 | 5/2008 | Czerkinsky et al. | |
| 2008/0193487 A1 | 8/2008 | Schild et al. | |
| 2008/0286296 A1 | 11/2008 | Ebensen et al. | |
| 2010/0047327 A1 | 2/2010 | Kuwahara et al. | |
| 2011/0070251 A1* | 3/2011 | Sugiyama | 424/185.1 |
| 2012/0045465 A1* | 2/2012 | Sugiyama | 424/185.1 |
| 2014/0220058 A1 | 8/2014 | Maeda et al. | |
| 2015/0150975 A1* | 6/2015 | Tanaka | A61K 47/12 424/185.1 |

FOREIGN PATENT DOCUMENTS

| EP | 2228072 A1 | 9/2010 |
|---|---|---|
| JP | 7-505883 A | 6/1995 |
| JP | 2002-531415 A | 9/2002 |
| JP | 2007-529531 A | 10/2007 |
| JP | 200874763 A | 4/2008 |
| JP | 2008127277 A * | 6/2008 |
| JP | 4422903 B2 | 12/2009 |
| JP | 2014169280 A | 9/2014 |
| RU | 2192884 C2 | 11/2002 |
| WO | 93/20847 A1 | 10/1993 |
| WO | 00/32228 A2 | 6/2000 |
| WO | 2003106682 A1 | 12/2003 |
| WO | 2005/087238 A2 | 9/2005 |
| WO | 2008093772 A1 | 8/2008 |

OTHER PUBLICATIONS

Inoue et al. (Journal of Investigative Dermatology, 2007, 127:614-621).*
Karande et al. (Annual Rev. Chem. Biomol. Eng., 2010, 1:175-201).*
Lim et al. Int. Immunopharmacol. Jan. 2003; 3(1): 115-118.*
Extended European search report issued with respect to European application No. 14000317.9, dated Apr. 7, 2014.
Yoshihiro Oka et al., Current Opinion in Immunology, 20: 211-220 (2008).
Hosoi Akihiro et al., Cancer Research, 68, 2008, pp. 3941-3949.
Zhengrong Cui et al., Pharmaceutical Research, vol. 19, No. 7, 2002, pp. 947-953.
European Office Action issued with respect to European Application No. 14000317.9, dated Dec. 15, 2016.
Chinese Office Action issued in Patent Application No. 201410042896. X, dated Mar. 1, 2017, along with an English translation thereof.

(Continued)

*Primary Examiner* — Daniel C Gamett
(74) *Attorney, Agent, or Firm* — Greenblum & Bernstein, P.L.C.

(57) ABSTRACT

The present invention provides a cancer vaccine composition for transdermal administration for cellular immunity induction, comprising (i) a WT1 peptide and/or a modified WT1 peptide; and (ii) a pharmacologically acceptable acid as a first cellular immunity induction promoter, or a pharmacologically acceptable salt thereof.

11 Claims, 1 Drawing Sheet

Specification includes a Sequence Listing.

(56) References Cited

OTHER PUBLICATIONS

European Search Report from Application No. 14000317.9 dated Jan. 12, 2018.
Japanese Office Action from Application No. 2014-014800 dated Oct. 31, 2017.
Russian Office Action and Search Report from Application No. 2014102940 dated Dec. 26, 2017.
Chinese Office Action from Application No. 201410042896.X dated Jan. 19, 2018.
Karande, Pankaj, "Transcutaneous immunization using common chemicals", 2009, Journal of Controlled Release, pp. 134-140, vol. 138.

* cited by examiner

SEQUENCE LISTING

```
<160> NUMBER OF SEQ ID NOS: 13

<210> SEQ ID NO 1
<211> LENGTH: 9
<212> TYPE: PRT
<213> ORGANISM: Homo sapiens

<400> SEQUENCE: 1

Arg Met Phe Pro Asn Ala Pro Tyr Leu
1               5

<210> SEQ ID NO 2
<211> LENGTH: 9
<212> TYPE: PRT
<213> ORGANISM: Homo sapiens

<400> SEQUENCE: 2

Cys Met Thr Trp Asn Gln Met Asn Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Tyr Thr Trp Asn Gln Met Asn Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Tyr Phe Pro Asn Ala Pro Tyr Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Ala Tyr Leu Pro Ala Val Pro Ser Leu
1               5

<210> SEQ ID NO 6
<211> LENGTH: 20
<212> TYPE: DNA
<213> ORGANISM: Unknown
<220> FEATURE:
<223> OTHER INFORMATION: Description of Unknown: Bacterial DNA
      sequence

<400> SEQUENCE: 6
tccatgacgt tcctgacgtt                                                   20

<210> SEQ ID NO 7
<211> LENGTH: 15
<212> TYPE: PRT
<213> ORGANISM: Mycobacterium tuberculosis

<400> SEQUENCE: 7

Phe Gln Asp Ala Tyr Asn Ala Ala Gly Gly His Asn Ala Val Phe
1               5                   10                  15

<210> SEQ ID NO 8
<211> LENGTH: 18
<212> TYPE: PRT
<213> ORGANISM: Homo sapiens

<400> SEQUENCE: 8

Trp Ala Pro Val Leu Asp Phe Ala Pro Pro Gly Ala Ser Ala Tyr Gly
1               5                   10                  15

Ser Leu

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (3)..(3)
<223> OTHER INFORMATION: Cyclohexylalanine
<220> FEATURE:
<221> NAME/KEY: MOD_RES
<222> LOCATION: (13)..(13)
<223> OTHER INFORMATION: D-Ala

<400> SEQUENCE: 9

Ala Lys Ala Val Ala Ala Trp Thr Leu Lys Ala Ala Ala
1               5                   10

<210> SEQ ID NO 10
<211> LENGTH: 16
<212> TYPE: PRT
<213> ORGANISM: Homo sapiens

<400> SEQUENCE: 10

Lys Arg Tyr Phe Lys Leu Ser His Leu Gln Met His Ser Arg Lys His
1               5                   10                  15
```

```
<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Gln Asp Ala Tyr Asn Ala Val His Ala Ala His Ala Val Phe
1               5                   10                  15

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Lys Lys Lys Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Asp Pro Lys His Pro Lys Ser Phe
1               5
```

WT1 PEPTIDE CANCER VACCINE COMPOSITION FOR TRANSDERMAL ADMINISTRATION

SEQUENCE LISTING

The instant application contains a Sequence Listing which has been submitted electronically in ASCII format and is hereby incorporated by reference in its entirety. Said ASCII copy, created on Mar. 18, 2014, is named P45215_SL.txt and is 3,362 bytes in size.

TECHNICAL FIELD

The present invention relates to a cancer vaccine for transdermal administration comprising a WT1 peptide and/or a modified WT1 peptide, and a cellular immunity induction promoter.

BACKGROUND ART

There are a cancer vaccine that prevents virus infection to prevent a cancer caused by the virus, and a cancer vaccine which provides the result that cancer cells are specifically attacked by the immune system via the recognition of a cancer-specific antigen by the immune mechanism, particularly, the cellular immune mechanism in which cytotoxic T cells (CTL) play an important role. The former is not effective at all for a cancer in which the virus does not participate. The latter is a cancer therapeutic strategy of targeting an antigen possessed by a cancer cell itself. It is considered that the latter is widely effective for cancers having antigen by specifying the antigen. Inter alia, a cancer vaccine based on the viewpoint of the latter can treat tumors that are difficult to remove by surgical operation because of their size, and causes less side effects as compared with the conventional therapies such as chemotherapy and radiation therapy.

WT1 (Wilm's tumor 1) gene is overexpressed in many hematopoietic tumors and solid cancers, for example, acute myelocytic leukemia, acute lymphocytic leukemia, chronic myelocytic leukemia, myelodysplastic syndrome, multiple myeloma, non-Hodgkin's lymphoma, lung cancer, breast cancer, stomach cancer, large intestine/rectum cancer, pancreas cancer, bile duct cancer, head and neck squamous cell cancer, thyroid cancer, kidney cancer, prostate cancer, ovarian cancer, uterine cancer, bone soft tissue sarcoma, malignant melanoma, malignant mesothelioma, testicular germ cell tumor and malignant glioma. Those cancers overproduce the WT1 protein. The WT1 protein is fragmented in the cancer cell to produce partial peptides consisting of 8 to 12 amino acids. A WT1 peptide is one of the peptide fragment which has been bound with the MHC class I molecule in a cancer cell, moved to the surface of the cancer cell, and presented as an antigen bound to the MHC class I molecule on the cancer cell surface. The WT1 peptide becomes a mark of the cancer cell. The amino acid sequence of the WT1 peptide conforms to the type of the MHC class I molecule of the cell. For example, in the case of a cell having HLA-A*0201-type MHC, a HLA-A*0201-type MHC restricted WT1 peptide such as Db126 peptide consisting of 9 amino acids is generated, and in the case of a cell having HLA-A*2402-type MHCa HLA-A*2402-type MHC restricted WT1 peptide such as Db235 peptide consisting of 9 amino acids is generated. In the case of a cell having other MHC, such as HLA-A26 type (WO 2005/095598), HLA-A*3303 type (WO 2007/097358), or HLA-A*1101 type (WO 2008/081701), each MHC restricted WT1 peptide is generated. When a WT1 peptide, or a modified WT1 peptide in which a part of amino acids of the WT1 peptide is substituted or modified is administered to a living body as an antigen (herein, a WT1 peptide or a modified WT1 peptide which has been administered as an antigen is referred to as "WT1 antigen peptide"), the WT1 antigen peptide is bound to the MHC Class I molecule on the surface of a dendritic cell which is an antigen presenting cell, or the WT1 antigen peptide is once taken into a dendritic cell, bound to the MHC class I molecule of the dendritic cell and then, is moved to the surface of the dendritic cell, thereby, is presented as an antigen bound to the MHC class I molecule on the surface of the dendritic cell. An activated dendritic cell having the WT1 antigen peptide/MHC class I molecule complex is moved to the regional lymph node, and activates a CD8-positive T lymphocyte which recognizes the WT1 antigen peptide/MHC class I molecule complex to differentiate and proliferate the cell into a cytotoxic T cell (CTL). CTL recognizes tumor cells having the complex of a WT1 peptide (derived from the endogenous WT1 protein) of the same amino acid sequence as the WT1 antigen peptide and the MHC class I molecule, or a tumor cell having a complex of a WT1 peptide (derived from the endogenous WT1 protein) of an amino acid sequence having cross immunoreactivity with the WT1 antigen peptide and the MHC class I molecule, and attacks the recognized tumor cells. Therefore, the aforementioned various MHC restricted WT1 peptides such as Db126 peptide and Db235 peptide, and modified WT1 peptides in which a part of amino acids of them are substituted or modified are useful as cancer vaccines (Non-Patent Document 1).

It is also known that an adjuvant is utilized in order to enhance the action as cancer vaccine of the WT1 peptide and/or the modified WT1 peptide. As the adjuvant for the WT1 peptide and/or the modified WT1 peptide, for example, mineral gels such as aluminum hydroxide; surfactants such as lysolecithin, and pluronicpolyol; polyanions; peptides; or oil emulsions (Patent Document 1), and GM-CSF, BCG-CWS and Montanide ISA51 (Non-Patent Document 1) are known. In addition to them, a variety of vaccine adjuvants including cyclic dinucleotide analogs (Patent Document 3 and Patent Document 4) such as 1H-imidazo[4,5-c]quinoline-4-amine, imiquimod (Patent Document 2), and cyclic di-GMP (c-di-GMP), and TLR2, 3, 7, 8 and 9 ligands (Patent Document 5) have been known. In addition, it is also known that immunity induced by transdermal administration of imiquimod-containing peptide is further enhanced by adding Peptide-25 (Non-Patent Document 2).

In general, vaccines are administered by subcutaneous or intradermal injection. In addition to those routes, immunity induction by a variety of administration routes, for example, transdermal administration (Patent Document 5 and Non-Patent Document 2), buccal administration, nasal administration, and sublingual administration (Non-Patent Document 3, Patent Document 6, and Patent Document 7) have been tried.

LIST OF DOCUMENTS

[Patent Document 1] Japanese Patent No. 4422903
[Patent Document 2] JP 7-505883 A
[Patent Document 3] JP 2007-529531 A
[Patent Document 4] US Patent Application Publication No. 2008/0286296
[Patent Document 5] US Patent Application Publication No. 2008/0193487

[Patent Document 6] JP 2002-531415 A
[Patent Document 7] US Patent Application Publication No. 2008/0112974

Non-Patent Documents

[Non-Patent Document 1] Yoshihiro Oka et al., Current Opinion in Immunology, 20: 211-220 (2008)
[Non-Patent Document 2] Hosoi Akihiro et al., Cancer Research, 68, 3941-3949 (2008)
[Non-Patent Document 3] Zhengrong Cui et al., Pharmaceutical Research, Vol. 19, No. 7, 947-953 (2002)

SUMMARY OF THE INVENTION

It is well-known that an adjuvant is used to enhance efficacy of a vaccine. Suitable adjuvants generally vary depending on, for example, the kind of the antigen, the administration route, and the immune response which is desired to be induced (i.e. cellular immunity or humoral immunity). Further, in addition to the adjuvant, there are a variety of substances which promote the induction of the immunity. Then, an object of the present invention is to provide a composition for use as a cancer vaccine with higher efficacy and is convenient for use.

A microorganism or a virus itself, or a part of them is contained in a widely used vaccine and the vaccine is administered to induce immune response. Usually, since invasion of the microorganism or virus is inhibited by the skin due to the size thereof, it is necessary that the vaccine is invasively administered into the body. Therefore, vaccines are usually administered by injection. However, the injection has some problems including pain, fear, injection scar, and subsequent scarring cicatrization. People other than health care workers are not permitted to perform the injection. Intradermal injection which can introduce higher immune response is a difficult administration technique. There is a risk of accidental infection of the health care workers due to needlestick injury. Patients are needed to visit the hospital repeatedly when administration is performed repetitively. Medical wastes which necessitate special disposition such as injection needles are generated. In view of the above issues, injection is not necessarily the optimal administration route.

A WT1 peptide and/or a modified WT1 peptide can activate CTL (cytotoxic T cell) via a MHC class I molecule, that is, the peptide can induce cellular immunity. The WT1 peptide and/or the modified WT1 peptide are a molecule having a molecular weight of about 700 to about 1600 and consisting of 8 to 12 amino acids, and are significantly smaller than microorganisms or virus itself although they are not considered as a small-molecule substance. It may be possible that they are administered by a route other than injection. However, a preparation for the administration of the peptide vaccine in a rout other than injection has not been developed yet. The reason includes many things, for example: a suitable substance that can promote to induce the cellular immunity has been unknown; it has also been unknown whether or not an antigen can be delivered to a tissue suitable for the induction of the cellular immunity. Inter alia, a substance that can promote to induce the cellular immunity, which can be used with the antigen when administered in a route other than injection has been unknown.

It was found out that, by transdermal administration, the cellular immunity induction effect which is equivalent to, or exceeds that of injection can be obtained. Then, a substance suitable for cellular immunity induction by transdermal administration of the WT1 peptide and/or the modified WT1 peptide was searched and, as a result, it was found out that use of a pharmacologically acceptable acid or a pharmacologically acceptable salt thereof is suitable. Further, it was found out that joint use of a pharmacologically acceptable acid with one or more kinds of cellular immunity induction promoters selected from the group consisting of a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor is suitable. In a particularly suitable aspect, cellular immunity was remarkably enhanced by a combination of a pharmacologically acceptable acid and a TLR ligand, or a combination of a pharmacologically acceptable acid, a TLR ligand and a helper peptide. Further, it was found out that, by administration under the mildly irritating condition, the high cellular immunity inducing effect is obtained. Specifically, the high cellular immunity inducing effect is obtained by selecting the mildly irritating state where the transepidermal water loss (TEWL) (g/h·m$^2$) which is an index of a skin of a model animal for skin irritation evaluation before administration of a cancer vaccine composition for transdermal administration is 50 or less, and administering a cancer vaccine composition for transdermal administration. Alternatively, the high cellular immunity inducing effect is also obtained by rendering skin irritation property of a cancer vaccine composition for transdermal administration such a mildly irritating property that the cutaneous TSLP level (pg/mg protein) of a model animal for skin irritation evaluation at completion of administration becomes 10000 or less.

Therefore, the present invention, in a first aspect, provides aspects listed below:

(1) A cancer vaccine composition for transdermal administration for cellular immunity induction, comprising:
(i) a WT1 peptide and/or a modified WT1 peptide; and
(ii) a pharmacologically acceptable acid as a first cellular immunity induction promoter or a pharmacologically acceptable salt thereof;
(2) The cancer vaccine composition for transdermal administration according to (1), wherein the pharmacologically acceptable acid or a pharmacologically acceptable salt thereof is an organic acid or a pharmacologically acceptable salt thereof;
(3) The cancer vaccine composition for transdermal administration according to (2), wherein the organic acid or a pharmacologically acceptable salt thereof is an organic compound containing carboxyl group or an organic compound containing sulfonate group, or a pharmacologically acceptable salt thereof;

(4) The cancer vaccine composition for transdermal administration according to (2), wherein the organic acid or a pharmacologically acceptable salt thereof is saturated or unsaturated straight or branched fatty acid in which a saturated straight chain part has 8 to 20 carbon atoms, lactic acid, malic acid, salicylic acid, maleic acid, citric acid, or an organic compound containing sulfonate group, or a pharmacologically acceptable salt thereof;

(5) The cancer vaccine composition for transdermal administration according to (2), wherein the organic acid or a pharmacologically acceptable salt thereof is fatty acid selected from the group consisting of decanoic acid, lauric acid, myristic acid, isostearic acid and oleic acid, or lactic acid, salicylic acid, citric acid or methanesulfonic acid, or a pharmacologically acceptable salt thereof;

(6) The cancer vaccine composition for transdermal administration according to any one of (1) to (5), further comprising a second cellular immunity induction promoter selected from a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor, and a combination of two or more kinds of them;

(7) The cancer vaccine composition for transdermal administration according to (6), wherein the second cellular immunity induction promoter is a TLR ligand;

(8) The cancer vaccine composition for transdermal administration according to (6), wherein the second cellular immunity induction promoter is a cyclic dinucleotide;

(9) The cancer vaccine composition for transdermal administration according to (6), wherein the second cellular immunity induction promoter is an immunomodulatory small molecule drug;

(10) The cancer vaccine composition for transdermal administration according to (6), wherein the second cellular immunity induction promoter is a cyclooxygenase inhibitor;

(11) The cancer vaccine composition for transdermal administration according to (6), wherein the second cellular immunity induction promoter is a prostaglandin receptor antagonist and, further, the prostaglandin receptor antagonist is an EP2 receptor antagonist, an EP4 receptor antagonist, a DP receptor antagonist, or an IP receptor antagonist;

(12) The cancer vaccine composition for transdermal administration according to (6), wherein the second cellular immunity induction promoter is a prostaglandin receptor agonist and, further, the prostaglandin receptor agonist is an EP3 receptor agonist;

(13) The cancer vaccine composition for transdermal administration according to (6), wherein the second cellular immunity induction promoter is a TSLP production inhibitor;

(14) The cancer vaccine composition for transdermal administration according to (6), wherein the second cellular immunity induction promoter is an adenylate cyclase inhibitor;

(15) The cancer vaccine composition for transdermal administration according to (6), wherein the second cellular immunity induction promoter is an omega-3 fatty acid;

(16) The cancer vaccine composition for transdermal administration according to (6), wherein the second cellular immunity induction promoter is a PPAR agonist and, further, the PPAR agonist is a PPAR-α agonist, a PPAR-δ agonist, or a PPAR-γ agonist;

(17) The cancer vaccine composition for transdermal administration according to (6), wherein the second cellular immunity induction promoter is a dopamine receptor antagonist and, further, the dopamine receptor antagonist is a D1 receptor antagonist, or a D5 receptor antagonist;

(18) The cancer vaccine composition for transdermal administration according to (6), wherein the second cellular immunity induction promoter is a dopamine receptor agonist and, further, the dopamine receptor agonist is a D2 receptor agonist, a D3 receptor agonist, or a D4 receptor agonist;

(19) The cancer vaccine composition for transdermal administration according to (6), wherein the second cellular immunity induction promoter is a histamine receptor antagonist and, further, the histamine receptor antagonist is a H1 receptor antagonist, or a H2 receptor antagonist;

(20) The cancer vaccine composition for transdermal administration according to (6), wherein the second cellular immunity induction promoter is a histamine receptor agonist and, further, the histamine receptor agonist is a H1 receptor agonist, a H3 receptor agonist, or a H4 receptor agonist;

(21) The cancer vaccine composition for transdermal administration according to (6), wherein the second cellular immunity induction promoter is a serotonin receptor antagonist and, further, the serotonin receptor antagonist is a 5-HT2 receptor antagonist, a 5-HT4 receptor antagonist, a 5-HT6 receptor antagonist, or a 5-HT7 receptor antagonist;

(22) The cancer vaccine composition for transdermal administration according to (6), wherein the second cellular immunity induction promoter is a serotonin receptor agonist and, further, the serotonin receptor agonist is a 5-HT1 receptor agonist, or a 5-HT2 receptor agonist;

(23) The cancer vaccine composition for transdermal administration according to (6), wherein the second cellular immunity induction promoter is a vasopressin receptor antagonist and, further the vasopressin receptor antagonist is a V2 receptor antagonist;

(24) The cancer vaccine composition for transdermal administration according to (6), wherein the second cellular immunity induction promoter is a vasopressin receptor agonist and, further, the vasopressin receptor agonist is a V1 receptor agonist;

(25) The cancer vaccine composition for transdermal administration according to (6), wherein the second cellular immunity induction promoter is a muscarine receptor antagonist and, further, the muscarine receptor antagonist is a M1 receptor antagonist, a M3 receptor antagonist, or a M5 receptor antagonist;

(26) The cancer vaccine composition for transdermal administration according to (6), wherein the second cellular immunity induction promoter is a muscarine receptor agonist and, further, the muscarine receptor agonist is a M1 receptor agonist, a M2 receptor agonist, a M3 receptor agonist, a M4 receptor agonist, or a M5 receptor agonist;

(27) The cancer vaccine composition for transdermal administration according to (6), wherein the second cellular immunity induction promoter is an adrenalin receptor antagonist and, further, the adrenalin receptor antagonist is an α1 receptor antagonist, a β1 receptor antagonist, a β2 receptor antagonist or a β3 receptor antagonist;

(28) The cancer vaccine composition for transdermal administration according to (6), wherein the second cellular immunity induction promoter is an adrenalin receptor agonist and, further, the adrenalin receptor agonist is an α1 receptor agonist, or an α2 receptor agonist;

(29) The cancer vaccine composition for transdermal administration according to (6), wherein the second cellular immunity induction promoter is an angiotensin receptor agonist and, further, the angiotensin receptor agonist is an AT2 receptor agonist;

(30) The cancer vaccine composition for transdermal administration according to (6), wherein the second cellular immunity induction promoter is a GABA receptor agonist and, further, the GABA receptor agonist is a $GABA_B$ receptor agonist;

(31) The cancer vaccine composition for transdermal administration according to (6), wherein the second cellular immunity induction promoter is a thrombin receptor antagonist and, further the thrombin receptor antagonist is a PAR-1 receptor antagonist;

(32) The cancer vaccine composition for transdermal administration according to (6), wherein the second cellular immunity induction promoter is a thrombin receptor agonist and, further the thrombin receptor agonist is a PAR-1 receptor agonist;

(33) The cancer vaccine composition for transdermal administration according to (6), wherein the second cellular immunity induction promoter is an opioid receptor agonist;

(34) The cancer vaccine composition for transdermal administration according to (6), wherein the second cellular immunity induction promoter is a leukotriene receptor antagonist and, further, the leukotriene receptor antagonist is a CysLT1 receptor antagonist, or a CysLT2 receptor antagonist;

(35) The cancer vaccine composition for transdermal administration according to (6), wherein the second cellular immunity induction promoter is a leukotriene receptor agonist and, further, the leukotriene receptor agonist is a BLT receptor agonist;

(36) The cancer vaccine composition for transdermal administration according to (6), wherein the second cellular immunity induction promoter is a melatonin receptor agonist;

(37) The cancer vaccine composition for transdermal administration according to (6), wherein the second cellular immunity induction promoter is a somatostatin receptor agonist;

(38) The cancer vaccine composition for transdermal administration according to (6), wherein the second cellular immunity induction promoter is a cannabinoid receptor agonist;

(39) The cancer vaccine composition for transdermal administration according to (6), wherein the second cellular immunity induction promoter is a sphingosine-1 phosphate receptor agonist;

(40) The cancer vaccine composition for transdermal administration according to (6), wherein the second cellular immunity induction promoter is a metabotropic glutamate receptor agonist and, further, the metabotropic glutamate receptor agonist is an mGluR2 receptor agonist, an mGluR3 receptor agonist, an mGluR4 receptor agonist, an mGluR6 receptor agonist, an mGluR7 receptor agonist, or an mGluR8 receptor agonist;

(41) The cancer vaccine composition for transdermal administration according to (6), wherein the second cellular immunity induction promoter is an ADP receptor agonist;

(42) The cancer vaccine composition for transdermal administration according to (6), wherein the second cellular immunity induction promoter is a phospholipase A2 inhibitor;

(43) The cancer vaccine composition for transdermal administration according to (6), wherein the second cellular immunity induction promoter is a TGF-β production inhibitor;

(44) The cancer vaccine composition for transdermal administration according to (6), wherein the second cellular immunity induction promoter is a Th2 cytokine inhibitor;

(45) The cancer vaccine composition for transdermal administration according to (6), wherein the second cellular immunity induction promoter is a helper peptide;

(46) The cancer vaccine composition for transdermal administration according to (6), wherein the second cellular immunity induction promoter is a combination of one or more kinds selected from the group consisting of a TLR ligand, a cyclic dinucleotide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor, with a helper peptide;

(47) The cancer vaccine composition for transdermal administration according to any one of (1) to (46), which is in a form of a cream formulation;

(48) The cancer vaccine composition for transdermal administration according to any one of (1) to (46), which is in a form of a liquid formulation;

(49) The cancer vaccine composition for transdermal administration according to any one of (1) to (48), which is administered under a mildly irritating condition;

(50) The cancer vaccine composition for transdermal administration according to (49), wherein the mildly irritating condition is a condition under which transepidermal water loss (TEWL) before administration in a model animal for skin irritation evaluation is 50 g/h·m$^2$ or less; and

(51) The cancer vaccine composition for transdermal administration according to (49) or (50), wherein the mildly irritating condition is a condition under which the cutaneous TSLP level at completion of administration in a model animal for skin irritation evaluation is 10000 pg/mg protein or less.

In other aspect, the cancer vaccine of the present invention can be used for treating or preventing a cancer. Therefore, the present invention also provides aspects listed below:

(52) A method of treating or preventing a cancer comprising transdermally administering a therapeutically effective amount of (i) a WT1 peptide and/or a modified WT1 peptide, and (ii) a pharmacologically acceptable acid or a pharmacologically acceptable salt thereof to a subject;

(53) A method of treating or preventing a cancer comprising transdermally administering, to a subject, a therapeutically effective amount of (i) a WT1 peptide and/or a modified WT1 peptide, (ii) a pharmacologically acceptable acid as a first cellular immunity induction promoter, or a pharmacologically acceptable salt thereof, and (iii) a second cellular immunity induction promoter selected from a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, a Th2 cytokine inhibitor, and a combination of two or more kinds of them;

(54) A method of treating or preventing a cancer comprising administering a therapeutically effective amount of the cancer vaccine composition for transdermal administration according to any one of (1) to (51) to a subject;

(55) A pharmacologically acceptable acid or a pharmacologically acceptable salt thereof, for use as a cellular immunity induction promoter for transdermally administering a WT1 peptide and/or a modified WT1 peptide; and

(56) A combination of (i) a pharmacologically acceptable acid or a pharmacologically acceptable salt thereof, and (ii) one or more kinds of substances selected from the group consisting of a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor, for use as a cellular immunity induction promoter for transdermally administering a WT1 peptide and/or a modified WT1 peptide;

(57) A method of inducing cellular immunity, comprising transdermally administering to a subject (i) WT1 peptide and/or modified WT1 peptide and (ii) a pharmacologically acceptable acid or a pharmacologically acceptable salt thereof as a first cellular immunity induction promoter;

(58) A pharmacologically acceptable acid or a pharmacologically acceptable salt thereof for use in accelerating the induction of cellular immunity by the transdermal administration of WT1 peptide and/or modified WT1 peptide;

(59) A combination of (i) a pharmacologically acceptable acid or a pharmacologically acceptable salt thereof and (ii) one or more substances selected from the group consisting of TLR ligand, cyclic dinucleotide, helper peptide, immunomodulatory small molecule drug, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor and Th2 cytokine inhibitor, for use in accelerating the induction of cellular immunity by the transdermal administration of WT1 peptide and/or modified WT1 peptide;

(60) A combination of (i) WT1 peptide and/or modified WT1 peptide and (ii) a pharmacologically acceptable acid or a pharmacologically acceptable salt thereof as a first cellular immunity induction promoter, for use in inducing cellular immunity by the transdermal administration of WT1 peptide and/or modified WT1 peptide;

(61) A combination of (i) WT1 peptide and/or modified WT1 peptide and (ii) a pharmacologically acceptable acid or a pharmacologically acceptable salt thereof for use in treating or preventing a cancer, wherein the combination is transdermally administered; and

(62) Use of (i) WT1 peptide and/or modified WT1 peptide and (ii) a pharmacologically acceptable acid or a pharmacologically acceptable salt thereof as a first cellular immunity induction promoter, for the manufacture of a cancer vaccine composition for transdermal administration intended for the induction of cellular immunity.

Since the cancer vaccine composition of the present invention can be transdermally administered, it has the following advantages: excellent compliance, for example, non-invasive administration, no pain, and release from fear of injection; patients can administer the cancer vaccine composition by himself/herself since the administration is simple; a risk of accidental infection due to needlestick injury by health care workers can be avoided; in the case of repetitive administration, the ambulatory frequency can be reduced, and this can contribute to the improvement in quality of life of the patient; and medical wastes which necessitate special disposition such as an injection needle are not generated. In addition, if the cancer vaccine composition is in a form of a patch preparation such as a cataplasm preparation or a tape preparation, a predetermined dose can be surely administered, the drug releasing rate can be arbitrarily controlled, and the cancer vaccine composition is not adhered to other site upon administration. Further, since the patch preparation can be easily detached, in the case where a side effect is generated, the patient himself/ herself can instantaneously stop the administration by removing the patch from the application site. Further, there is also an advantage that efficacy of the cancer vaccine composition of the present invention is remarkably improved, as compared with administration of the WT1 peptide and/or the modified WT1 peptide alone. Further, there is also has an advantage that, by using a pharmacologically acceptable acid or a pharmacologically acceptable salt thereof, efficacy of the cancer vaccine composition for transdermal administration is more improved. Further, the cancer vaccine composition of the present invention also has an advantage that transdermal administration of the composition induces stronger cellular immunity as compared with injection administration.

DETAILED DESCRIPTION OF THE INVENTION

Figure 1:
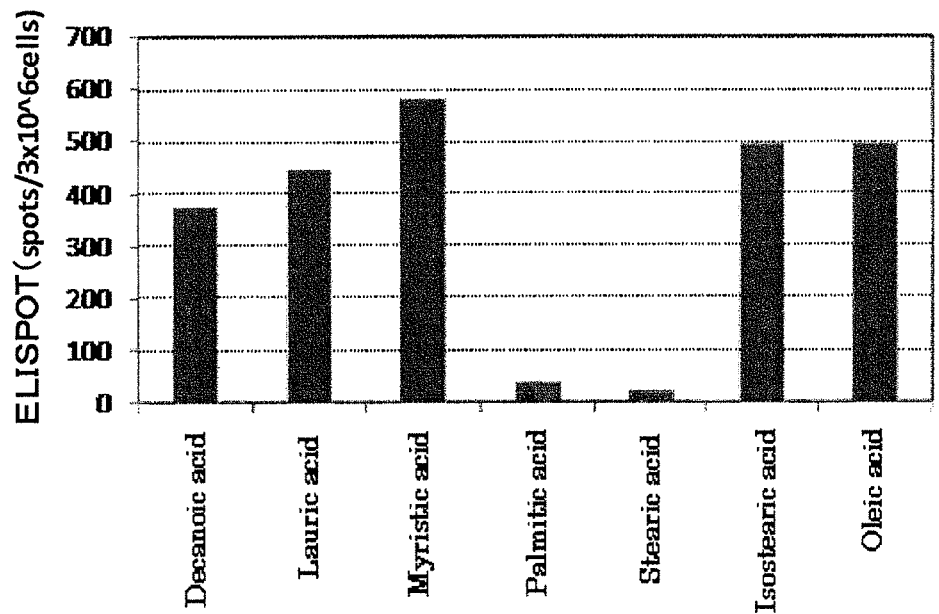
FIG. 1 is a view showing cellular immunity inducing effect by a PIB tape preparation with various acids incorporated therein.

First, terms used in the present specification will be defined so that the present invention can be more easily understood. Terms having no definition have the meaning which is normally understood by a person skilled in the art in the fields of, particularly, medicine, pharmacy, immunology, cell biology, biochemistry, polymer chemistry and the like, unless the context requires otherwise.

I. Definition

As used herein, the term "WT1 peptide" means a partial peptide consisting of about 8 to about 15, preferably about 8 to about 12 amino acids, which is obtained by fragmenting a WT1 protein which is a product of a cancer gene WT1 (Wilm's tumor), and includes a Db126 peptide, a Db235 peptide and the like. In addition, a partial peptide of a WT1 product disclosed in WO 2000/06602, a WT1-derived HLA-A26 binding cancer antigen peptide described in WO 2005/095598, a HLA-A*3303-restricted WT1 peptide described in WO 2007/097358, and a HLA-A*1101-restricted WT1 peptide described in WO 2008/081701 are also included in the "WT1 peptide" of the present invention.

The term "Db126 peptide" means a WT1 peptide consisting of a sequence Arg Met Phe Pro Asn Ala Pro Tyr Leu (SEQ ID No.: 1). The term "Db235 peptide" means a WT1 peptide consisting of a sequence Cys Met Thr Trp Asn Gln Met Asn Leu (SEQ ID No.: 2) (Patent Document 1).

As used herein, the term "modified WT1 peptide" means a peptide in which all or a part of amino acids of a WT1 peptide are modified by substitution, modification or the like.

The modified WT1 peptide includes, for example,
(a) a peptide consisting of an amino acid sequence in which one to several, for example, 1, 2, 3, 4 or 5 amino acids are substituted, deleted or added in an amino acid sequence of a WT1 peptide; and
(b) a peptide consisting of an amino acid sequence in which all or a part of amino acids, for example, one or more, for example, 1, 2, 3, 4, 5, 6, 7, 8, 9, 10, 11 or 12 amino acids are modified in an amino acid sequence of a WT1 peptide.

Examples of "modification" of an amino acid which can be possessed by a modified WT1 peptide include, but not limited to, aliphatic chain addition modification such as alkylation such as acetylation and methylation, glycosylation, hydroxylation, carboxylation, aldehydization, phosphorylation, sulfonylation, formylation, myristoylation, palmitoylation and stearoylation, octanoylation, esterification, amidation, deamidation, disulfide bond formation modification such as cystine modification, glutathione modification and thioglycolic acid modification, glycation, ubiquitination, succinimide formation, glutamylation, prenylation and the like. The modified WT1 peptide may contain a combination of substitution, deletion or addition of one or more amino acids, and modification of one or more amino acids.

As a specific example, a Db235m peptide in which a part of a Db235 peptide is modified is a modified WT1 peptide consisting of a sequence Cys Tyr Thr Trp Asn Gln Met Asn Leu (SEQ ID No.: 3) (WO 2002/079253), and is included in the modified WT1 peptide in the present invention. A WT1 substitution type peptide described in WO 2004/026897, a $WT1_{235-293}$ peptide derivative disclosed in WO 2007/063903 A1, and a HLA-A24 restrictive cancer antigen peptide disclosed in WO 2003/106682 are also included in the modified WT1 peptide in the present invention. Specific examples of the HLA-A24 restrictive modified WT1 peptide described in WO 2003/106682 include a RYF peptide of a sequence Arg Tyr Phe Pro Asn Ala Pro Tyr Leu (SEQ ID No.: 4), and an AYL peptide of a sequence Ala Tyr Leu Pro Ala Val Pro Ser Leu (SEQ ID No.: 5).

The WT1 peptide and/or the modified WT1 peptide can be in the free form or any pharmacologically acceptable salt form, for example, a form of acid salts (acetic acid salt, TFA salt, hydrochloric acid salt, sulfuric acid salt, phosphoric acid salt, lactic acid salt, tartaric acid salt, maleic acid salt, fumaric acid salt, oxalic acid salt, hydrobromic acid salt, succinic acid salt, nitric acid salt, malic acid salt, citric acid salt, oleic acid salt, palmitic acid salt, propionic acid salt, formic acid salt, benzoic acid salt, picric acid salt, benzenesulfonic acid salt, dodecylsulfuric acid salt, methanesulfonic acid salt, p-toluenesulfonic acid salt, glutaric acid salt, various amino acid salts, etc.), metal salts (alkali metal salts (e.g. sodium salt, potassium salt), alkaline earth metal salts (e.g. calcium salt, magnesium salt), aluminum salt etc.), or amine salts (triethylamine salt, benzylamine salt, diethanolamine salt, t-butylamine salt, dicyclohexylamine salt, arginine salt, dimethylammonium salt, ammonium salt, etc.). A preferable pharmacologically acceptable salt is an acetic acid salt or a TFA salt. The WT1 peptide and/or the modified WT1 peptide which has been synthesized or produced, and isolated and purified by a well-known method can be used.

As used herein, the term "cellular immunity induction promoter" means any substance which can enhance the cellular immune response induced by an antigen which is administered together with the substance, as compared with the immune response induced by the antigen without the substance. The cellular immunity induction promoter may include substances specified in the present specification, though it is not limited by the action mechanism by which induction of the cellular immunity is promoted.

As used herein, the term "TLR ligand" means a ligand of a Toll-like receptor (TLR), and includes, for example, ligands of TLR1 to 9. Examples of the TLR ligand include a TLR1/2 ligand, a TLR2/6 ligand, a TLR2 and Dectin1 ligand, a TLR3 ligand, a TLR4 ligand, a TLR5 ligand, a TLR7 and/or TLR8 ligand, a TLR9 ligand and the like. In a preferable aspect of the present invention, the TLR ligand is a TLR1/2 ligand, a TLR2 and Dectin1 ligand, a TLR3 ligand, a TLR4 ligand, a TLR7 and/or TLR8 ligand, and/or a TLR9 ligand.

As used herein, the term "TLR1/2 ligand" means a ligand of a heterodimer of a Toll-like receptor (TLR) 1 and a Toll-like receptor (TLR) 2, and includes, for example, a triacylated lipoprotein derived from a cell wall of a bacterium and a salt thereof, and these may be an extract, a product or a synthetic product, and are not limited to them.

In a preferable aspect of the present invention, the TLR1/2 ligand is Pam₃CSK₄. Pam₃CSK₄ has the formula ("Ser-Lys-Lys-Lys-Lys" disclosed as SEQ ID NO: 12):

and includes, for example, a single-stranded RNA, imiquimod, resiquimod (R848), TLR7-II and other compounds, for example, loxoribine and bropirimine, but is not limited to them.

In a preferable aspect of the present invention, the TLR7 and/or TLR8 ligand is imiquimod. Imiquimod is 1-(2-methylpropyl)-1H-imidazo[4,5-c]quinoline-4-amine of the formula:

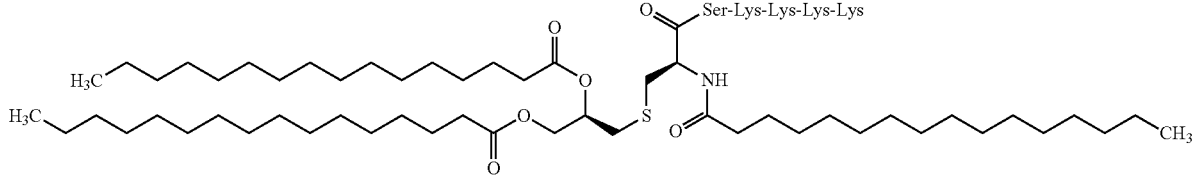

As used herein, the term "TLR2 and Dectin1 ligand" means a ligand of a Toll-like receptor (TLR) 2 and a β1,3-glucan receptor (Dectin1), and includes, for example, a β1,3-glucan derived from a cell wall of a fungus and a salt thereof, and these may be an extract, a product or a synthetic product, and are not limited to them. In a preferable aspect of the present invention, the TLR2 and Dectin1 ligand is Zymosan derived from a yeast cell wall.

As used herein, the term "TLR3 ligand" means a ligand of a Toll-like receptor (TLR) 3, and includes, for example, a double-stranded RNA (dsRNA) derived from a virus and a salt thereof, and these may be an extract, a product or a synthetic product, and are not limited to them. In a preferable aspect of the present invention, the TLR3 ligand is polyinosinic-polycytidylic acid (Poly(I:C)) which is a synthetic product and/or a salt thereof.

As used herein, the term "TLR4 ligand" means a ligand of a Toll-like receptor (TLR) 4, and includes, for example, a lipopolysaccharide (LPS) derived from a bacterium or a plant, particularly, a lipid A derivative, for example, monophosphoryl lipid A, a 3 deacylated monophosphoryl lipid A (3D-MPL), OM174, OM 294 DP or OM 197 MP-Ac DP and the like, alkyl glucosaminide phosphate (AGP), for example, AGP disclosed in WO 98/50399 or U.S. Pat. No. 6,303,347, or a salt of AGP as disclosed in U.S. Pat. No. 6,764,840, and a lipopolysaccharide, a glucopyranosyl lipid, and sodium hyaluronate derived from a *Pantoea* bacterium, but is not limited to them.

In a preferable aspect of the present invention, as the TLR4 ligand, lipopolysaccharides derived from genus *Acetobacter* (e.g. *Acetobacter aceti*, *Acetobacter xylinum*, *Acetobacter orientalis* etc.), genus *Zymomonas* (e.g. *Zymomonas mobilis* etc.), genus *Xanthomonas* (e.g. *Xanthomonas campestris* etc.), genus *Enterobacter* (e.g. *Enterobacter cloacae* etc.), and genus *Pantoea* (e.g. *Pantoea agglomerans* etc.) are preferable. Extracts derived from these lipopolysaccharides or purified lipopolysaccharides can be used as they are. In addition, for example, lipopolysaccharides (IP-PA1) derived from *Pantoea agglomerans* can be purchased from Funakoshi Corporation. In addition, in a preferable aspect of the present invention, the TLR4 ligand is a lipopolysaccharide, glucopyranosyl lipid, and/or sodium hyaluronate derived from a *Pantoea* bacterium.

As used herein, the term "TLR7 and/or TLR8 ligand" means a ligand of a Toll-like receptor (TLR) 7 and/or TLR8,

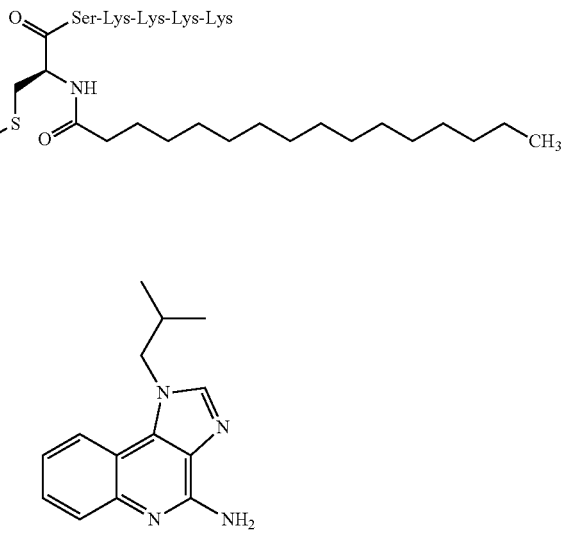

and, for example, the characteristics and a production process thereof are described in JP 7-505883 A (Patent Document 2).

In other preferable aspect, the TLR7 and/or TLR8 ligand is resiquimod. Resiquimod is 4-amino-2-(ethoxymethyl)-α,α-dimethyl-1H-imidazo[4,5-c]quinoline-1-ethanol of the formula:

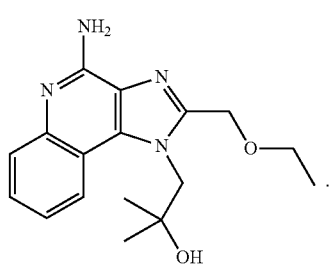 [SMILES: CCOCc1nc2c(N)nc3ccccc3c2n1CC(C)(C)O]

In other preferable aspect, the TLR7 and/or TLR8 ligand is TLR7-II. TLR7-II is represented by the formula:

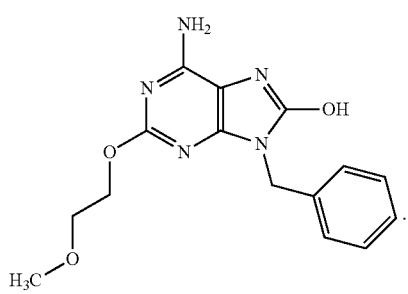 [SMILES: COCCOc1nc(N)c2nc(O)n(Cc3ccccc3)c2n1]

In other preferable aspect, the TLR7 and/or TLR8 ligand is bropirimine. Bropirimine is represented by the formula:

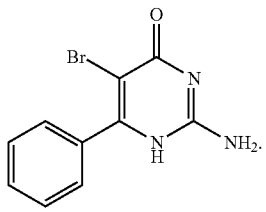 [SMILES: Nc1nc(=O)c(Br)c(-c2ccccc2)[nH]1]

As used herein, the term "TLR9 ligand" means a ligand of a Toll-like receptor (TLR) 9, and includes, for example, ODN1826 and the like. The TLR9 ligand used in the present invention may be an extract, a product or a synthetic product, and is not limited to them. In a preferable aspect of the present invention, the TLR9 ligand is ODN1826.

ODN1826 is an oligodeoxynucleotide consisting of the following sequence (SEQ ID No.: 6).

```
5'-tccatgacgttcctgacgtt-3'
```

As used herein, the term "TLR2/6 ligand" means a ligand of a heterodimer of Toll-like receptor (TLR) 2 and a Toll-like receptor (TLR) 6, and includes, for example, a diacylated lipoprotein derived from a cell wall of mycoplasma and a salt thereof, and these may be an extract, a product or a synthetic product, and are not limited to them. In a preferable aspect of the present invention, the TLR2/6 ligand is Pam$_2$CSK$_4$, MALP-2 and/or FSL-1.

Pam$_2$CSK$_4$ is represented by the following formula ("Ser-Lys-Lys-Lys-Lys" disclosed as SEQ ID NO: 12).

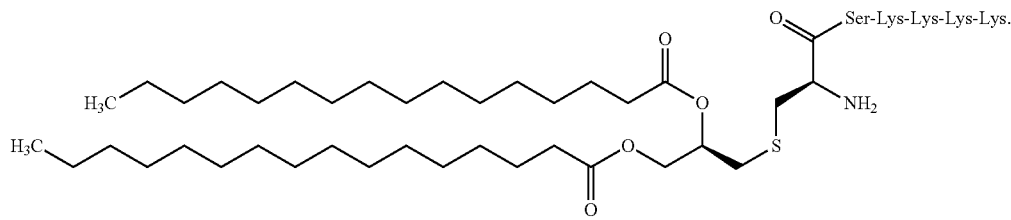

FSL-1 is represented by the following formula ("Gly-Asp-Pro-Lys-His-Pro-Lys-Ser-Phe" disclosed as SEQ ID NO: 13).

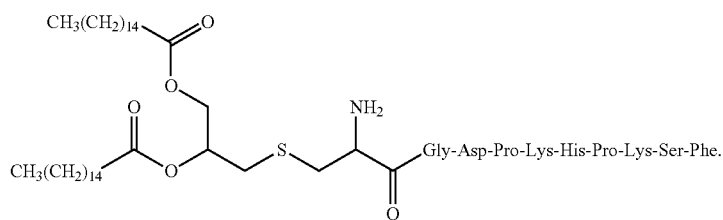

As used herein, the term "TLR5 ligand" means a ligand of a Toll-like receptor (TLR) 5, and includes, for example, flagellin and the like. The TLR5 ligand used in the present invention may be an extract, a product or a synthetic product, and is not limited to them. In a preferable aspect of the present invention, the TLR5 ligand is flagellin.

The Toll-like receptor (TLR) is a family of 1-type transmembrane proteins which initiates congenital immune response in which a specific cytokine, a specific chemokine and a growth factor participate, by in vivo activation thereof. All TLRs can activate a certain intracellular signal transmission molecule, for example, a nuclearity factor κB (NF-κB) and a mitogen-activated protein kinase (MAP kinase) or the like, while a specific population of a cytokine and a chemokine which are released seems to be inherent to each TLR. TLR3, 7, 8 and 9 include a subfamily of TLR which is present in an endosome fraction or a lysosome fraction of an immune cell (e.g. dendritic cell and monocyte). Specifically, TLR3 is expressed by a wide range of cells such as a dendritic cell and a fibroblast, TLR7 is expressed by a plasma cell-like dendritic cell, and is expressed by a monocyte to a lesser extent, TLR8 is expressed by a monocyte as well as a monocyte-derived dendritic cell and a myelogenous dendritic cell, and TLR9 is expressed by a plasma cell-like dendritic cell. This subfamily mediates recognition of a microorganism nucleic acid (single-stranded RNA, double-stranded RNA, single-stranded DNA etc.). Agonists of TLR3, TLR7 and/or TLR8, and TLR9 stimulate production of a variety of inflammatory cytokines (including, for example, interleukin-6, interleukin-12, TNF-α, and interferon-γ). Such agonists also promote increase in expression of a costimulating molecule (e.g. CD40, CD80, and CD86), a major histocompatibility complex molecule, and a chemokine receptor. I-type interferons (IFNα and IFNβ) are produced by a cell upon activation with TLR7 and/or TLR8 agonists.

As used herein, the term "cyclic dinucleotide" means a molecule in which two OH groups of a sugar part of two nucleotides produce an ester for each same phosphoric acid molecule, and thereby nucleotides are cyclized, and an analog thereof, and includes, for example, cyclic di-AMP (c-di-AMP), cyclic di-GMP (c-di-GMP), c-dGpGp, c-dGp-dGp, c-GpAp, c-GpCp, c-GpUp and the like, but is not limited to them. The cyclic dinucleotide activates a dendritic cell or a T cell. Further examples of the cyclic dinucleotide, use of them as an adjuvant, and a process for producing them are described in JP 2007-529531 A (Patent Document 3). In a preferable aspect of the present invention, the cyclic dinucleotide is cyclic di-GMP and/or cyclic di-AMP. The cyclic di-GMP has the formula:

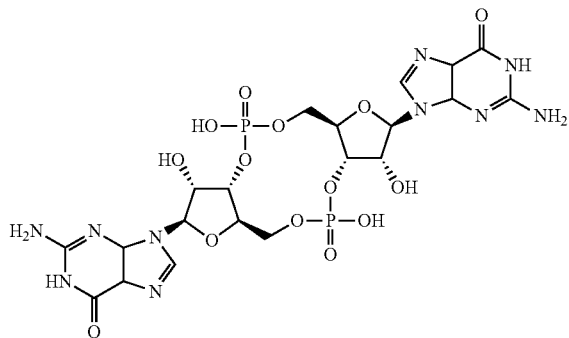 [SMILES: NC1=NC2C(N=CN2[C@@H]2O[C@@H]3COP(=O)(O)O[C@H]4[C@@H](O)[C@H](N5C=NC6C(=O)NC(N)=NC65)O[C@@H]4COP(=O)(O)O[C@H]3[C@H]2O)C(=O)N1]

and a process for synthesizing it is described in Kawai et al., Nucleic Acids Research Suppl. 3: 103-4.

As used in the present specification, the term "helper peptide" means any peptide which activates a helper T cell, and includes, for example, tubercle *bacillus*-derived helper peptide, measles virus-derived helper peptide, hepatitis B virus-derived helper peptide, hepatitis C virus-derived helper peptide, *Chlamydia trachomatis*-derived helper peptide, *Plasmodium falciparum* sporozoite-derived helper peptide, keyhole limpet haemocyanin-derived helper peptide, tetanus toxin-derived helper peptide, pertussis toxin-derived helper peptide, diphtheria toxin-derived helper peptide, cancer cell-derived helper peptide (e.g. WT1_{332-347} helper peptide (described in Japanese Patent No. 4621142 "WT1-derived HLA-DR binding Antigen Peptide"), hWT1_{35} helper peptide, hWT1_{86} helper peptide, hWT1_{294} helper peptide (above three kinds are described in WO 2010/123065 "Cancer Antigen Helper Peptide"), IMA-MMP-001 helper peptide, CEA-006 helper peptide, MMP-001 helper peptide, TGFBI-004 helper peptide, HER-2/neu (aa776-790) helper peptide, AE36 helper peptide, AE37 helper peptide, MET-005 helper peptide, BIR-002 helper peptide etc.), and universal helper analog (e.g. PADRE). In a preferable aspect of the present invention, the helper peptide consists of 10 to 20 amino acids, preferably 12 to 19 amino acids, more preferably 13 to 18 amino acids. In a preferable aspect of the present invention, the helper peptide is Peptide-25, hWT1_{35}, PADRE, or WT1_{332-347}. Peptide-25 is a peptide of 15 amino acids consisting of a sequence Phe Gln Asp Ala Tyr Asn Ala Ala Gly Gly His Asn Ala Val Phe (SEQ ID No.: 7), corresponding to amino acid residues 240 to 254 of Ag85B which is one of main proteins secreted by human tubercle *bacillus* (*Mycobacterium tuberculosis*). Further, hWT1_{35} is a peptide of 18 amino acids consisting of a sequence Trp Ala Pro Val Leu Asp Phe Ala Pro Pro Gly Ala Ser Ala Tyr Gly Ser Leu (shown as SEQ ID No.: 8 in the present application), described in WO 2010/123065 "Cancer Antigen Helper Peptide". PADRE is a peptide of 13 amino acids consisting of a sequence D-Ala Lys cyclohexyl-Ala Val Ala Ala Trp Thr Leu Lys Ala Ala D-Ala (shown as SEQ ID No.: 9 in the present application). WT$^1$_{332-347} is a peptide of 16 amino acids consisting of a sequence Lys Arg Tyr Phe Lys Leu Ser His Leu Gln Met His Ser Arg Lys His (shown as SEQ ID No.: 10 in the present application), described in Japanese Patent No. 4621142 "WT1-derived HLA-DR binding Antigen Peptide".

In addition, in the present invention, in place of the aforementioned helper peptides, or in combination therewith, peptides in which all or a part of amino acids of the helper peptides are modified by substitution, modification, or the like (hereinafter, referred to as "modified helper peptide") can also be used.

The modified helper peptide includes, for example, (a) a peptide consisting of an amino acid sequence in which one to several, for example, 1, 2, 3, 4 or 5 amino acids are substituted, deleted or added, in an amino acid sequence of the original helper peptide; and (b) a peptide consisting of an amino acid sequence in which all or a part of amino acids, for example, one or more, for example, 1, 2, 3, 4, 5, 6, 7, 8, 9, 10, 11, 12, 13, 14, 15, 16, 17, or 18 amino acids are modified, in an amino acid sequence of the original helper peptide.

One example of the modified helper peptide is Peptide-25B. Peptide-25B is one example of modified Peptide-25, in which a part of amino acids of Peptide-25 are modified in order to enhance the immunostimulation effect, and is a peptide of 15 amino acids consisting of a sequence Phe Gln Asp Ala Tyr Asn Ala Val His Ala Ala His Ala Val Phe (SEQ ID No. 11).

Examples of the "modification" of an amino acid which can be possessed by the modified helper peptide include, but are not limited to, aliphatic chain addition modification such as acetylation, alkylation such as methylation, glycosylation, hydroxylation, carboxylation, aldehydization, phosphorylation, sulfonylation, formylation, addition of fatty acid such as myristoylation, palmitoylation and stearoylation, octanoylation, esterification, amidation, deamidation, disulfide bond formation modification such as cystine modification, glutathione modification and thioglycolic acid modification, glycation, ubiquitination, succinimide formation glutamylation, prenylation and the like. In addition, the modified helper peptide may contain a combination of substitution, deletion or addition of one or more amino acids, and modification of one or more amino acids.

As used herein, the term "cyclooxygenase inhibitor" means a substance which inhibits the function of cyclooxygenase (COX). This is also referred to as "COX inhibitor" hereinafter. As COX inhibitors, there are a COX inhibitor which selectively acts on particular cyclooxygenase (e.g. COX-1 or COX-2), and a COX inhibitor having no selectivity. Examples of COX inhibitors which can be used in the present invention include etodolac, loxoprofen, celecoxib, valdecoxib, parecoxib, lumiracoxib, meloxicam, tenoxicam, diclofenac, mefenamic acid, tolfenamic acid, flufenamic acid, meclofenamic acid, niflumic acid, benzydamine, indobufen, triflusal, tolmetin, fenoprofen, tiaprofenic acid, felbinac, nepafenac, amfenac, pravadoline, zaltoprofen, sulindac, nabumetone, diflunisal, piroxicam, ibuprofen, naproxen, fenoprofen, aspirin, methyl salicylate, salicylamide, salsalate, aloxiprin, tolmetin, indomethacin, proglumetacine, acemetacin, flurbiprofen, pranoprofen, acetaminophen, floctafenine, lornoxicam, tenoxicam, tiaprofenic acid, oxaprozin, ketoprofen, dexketoprofen, dexibuprofen, alminoprofen, ketorolac, mofezolac, phenylbutazone, oxyphenylbutazone, ketophenylbutazone, feprazone, phenbutazone, ethenzamide, tiaramide, tinoridine, epirizole, emorfazone and a derivative thereof, as well as a pharmacologically acceptable salt thereof. In a preferable aspect of the present invention, the COX inhibitor is etodolac and/or loxoprofen.

Loxoprofen is represented by the formula:

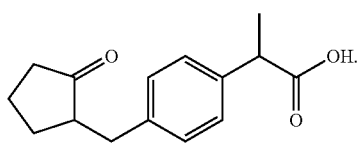 [SMILES: CC(C(=O)O)c1ccc(CC2CCCC2=O)cc1]

As used herein, the term "prostaglandin receptor antagonist" means a substance having the function of preventing prostaglandin from acting on a receptor, and includes, for example, an EP2 receptor antagonist, an EP4 receptor antagonist, a DP receptor antagonist, and an IP receptor antagonist.

As used herein, the term "EP2 receptor antagonist" means a substance having the function of preventing prostaglandin E2 from acting on an EP2 receptor. Examples of the EP2 receptor antagonist include AH6809 and a derivative thereof, as well as a pharmacologically acceptable salt thereof.

AH6809 is represented by the formula:

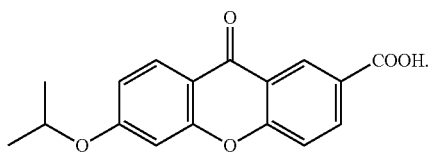 [SMILES: CC(C)Oc1ccc2c(=O)c3cc(C(=O)O)ccc3oc2c1]

As used herein, the term "EP4 receptor antagonist" means a substance having the function of preventing prostaglandin $E_2$ from acting on an EP4 receptor. Examples of the EP4 receptor antagonist include GW627368X and a derivative thereof, as well as a pharmacologically acceptable salt thereof.

GW627368X is represented by the formula:

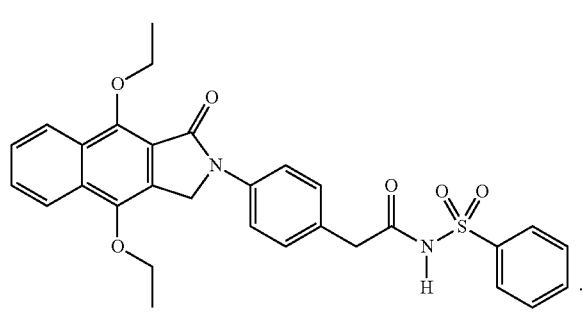 [SMILES: CCOc1c2c(c(OCC)c3ccccc13)C(=O)N(c1ccc(CC(=O)NS(=O)(=O)c3ccccc3)cc1)C2]

As used herein, the term "DP receptor antagonist" means a substance having the function of preventing prostaglandin $D_2$ from acting on a DP receptor. Examples of the DP receptor antagonist include S-5751, BWA868C and a derivative thereof, as well as a pharmacologically acceptable salt thereof.

BWA868C is represented by the formula:

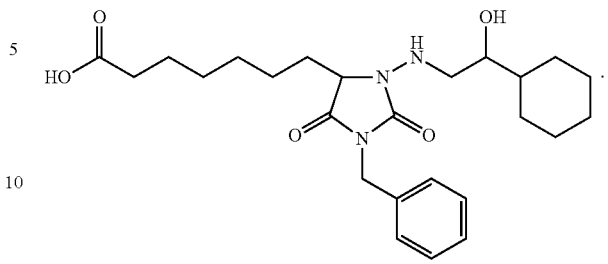

As used herein, the term "IP receptor antagonist" means a substance having the function of preventing prostaglandin $I_2$ from acting on an IP receptor. Examples of the IP receptor antagonist include RO1138452 and a derivative thereof, as well as a pharmacologically acceptable salt thereof.

RO1138452 is represented by the formula:

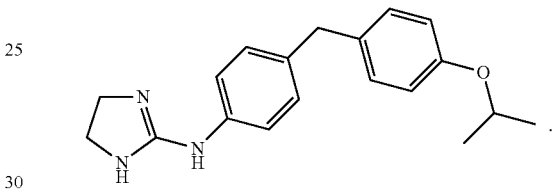

As used herein, the term "prostaglandin receptor agonist" means a substance having the function of acting on a prostaglandin receptor, and includes, for example, an EP3 receptor agonist.

As used herein, the term "EP3 receptor agonist" means a substance having the function of acting on an EP3 receptor. Examples of the EP3 receptor agonist include sulprostone, GR63799, cloprostenol, ONO-AE-248, carbacyclin, and a derivative thereof, as well as a pharmacologically acceptable salt thereof.

Sulprostone is represented by the formula:

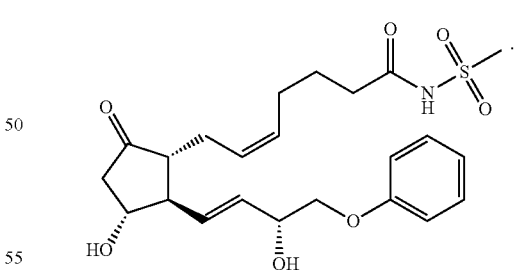

As used herein, the term "TSLP production inhibitor" means a substance having the function of inhibiting production of TSLP. Since a drug which inhibits NF-κB is thought to indirectly inhibit the production of TSLP, it is included in this category. Examples of the TSLP production inhibitor include naringenin, berberine, resveratrol, luteolin, apigenin, chrysoeriol, velutin, rutin, hesperidin, quercetin, daidzein, genistein, noscapine, diindolylmethane, xanthone, parthenolide and a derivative thereof, as well as a pharmacologically acceptable salt thereof.

Berberine is represented by the formula:

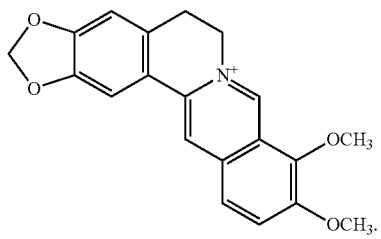 [SMILES: COc1ccc2cc3[n+](cc2c1OC)CCc1cc2c(cc1-3)OCO2]

As used herein, the term "adenylate cyclase inhibitor" means a substance having the function of inhibiting the activity of adenylate cyclase. Examples of the adenylate cyclase inhibitor include 2',5'-dideoxyadenosine, niacin, insulin, and a derivative thereof, as well as a pharmacologically acceptable salt thereof.

2',5'-Dideoxyadenosine is represented by the formula:

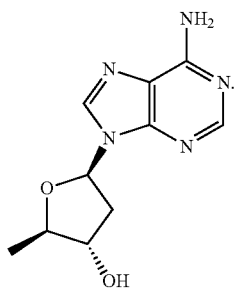 [SMILES: C[C@H]1O[C@@H](n2cnc3c(N)ncnc32)C[C@@H]1O]

As used herein, the term "omega-3 fatty acid" refers to an unsaturated fatty acid having a carbon-carbon double bond at a ω-3 position. Examples of the omega-3 fatty acid include eicosapentaenoic acid, α-linolenic acid, docosahexaenoic acid, and a derivative thereof, as well as a pharmacologically acceptable salt thereof.

Eicosapentaenoic acid is represented by the formula:

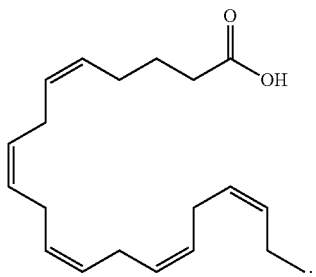 [SMILES: CC/C=C\C/C=C\C/C=C\C/C=C\C/C=C\CCCC(=O)O ; "."]

As used herein, the term "PPAR agonist" means a substance having the function of acting on a peroxisome proliferator-activated receptor, and includes, for example, a PPAR-α agonist, a PPAR-δ agonist, and a PPAR-γ agonist.

As used herein, the term "PPAR-α agonist" means a substance having the function of acting on an α type peroxisome proliferator-activated receptor. The term "PPAR-δ agonist" means a substance having the function of acting on a δ type peroxisome proliferator-activated receptor. The term "PPAR-γ agonist" means a substance having the function of acting on a γ type peroxisome proliferator-activated receptor. Examples of the PPAR-α agonist, and/or the PPAR-δ agonist, and/or the PPAR-γ agonist include clofibrate, fenofibrate, bezafibrate, ciprofibrate, etofibrate, telmisartan, oleyl ethanolamide, tetradecylthioacetic acid, troglitazone, pioglitazone, rosiglitazone, balaglitazone, rivoglitazone, ciglitazone, darglitazone, edaglitazone, netoglitazone, indeglitazar, tesaglitazar, muraglitazar, aleglitazar, and a derivative thereof, as well as a pharmacologically acceptable salt thereof.

Clofibrate is represented by the formula:

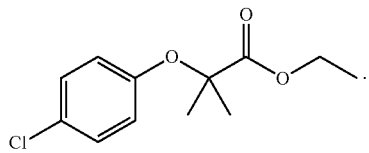 [SMILES: CCOC(=O)C(C)(C)Oc1ccc(Cl)cc1 ; "."]

As used herein, the term "dopamine receptor antagonist" means a substance having the function of preventing dopamine from acting on a receptor, and includes, for example, a D1 receptor antagonist, and a D5 receptor antagonist.

As used herein, the term "D1 receptor antagonist" means a substance having the function of preventing dopamine from acting on a D1 receptor. Examples of the D1 receptor antagonist include benzazepine, fenoldopam, lorcaserin, SCH23390, SCH39166, LE300 and a derivative thereof, as well as a pharmacologically acceptable salt thereof.

Benzazepine is represented by the formula:

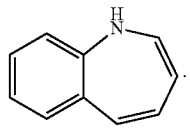 [SMILES: C1=CNc2ccccc2C=C1 ; "."]

As used herein, the term "D5 receptor antagonist" means a substance having the function of preventing dopamine from acting on a D5 receptor. Examples of the D5 receptor antagonist include SCH39166 and a derivative thereof, as well as a pharmacologically acceptable salt thereof.

SCH39166 is represented by the formula:

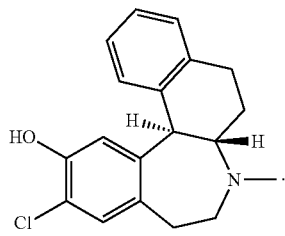 [SMILES: CN1CCc2cc(Cl)c(O)cc2[C@H]2c3ccccc3CC[C@@H]21 ; "."]

As used herein, the term "dopamine receptor agonist" means a substance having the function of acting on a dopamine receptor, and includes, for example, a D2 receptor agonist, a D3 receptor agonist, and a D4 receptor agonist.

As used herein, the term "D2 receptor agonist" means a substance having the function of acting on a D2 receptor. Examples of the D2 receptor agonist include cabergoline, bromocriptine, pergolide, ropinirole, talipexole, aripiprazole, lurasidone, and a derivative thereof, as well as a pharmacologically acceptable salt thereof.

Ropinirole is represented by the formula:

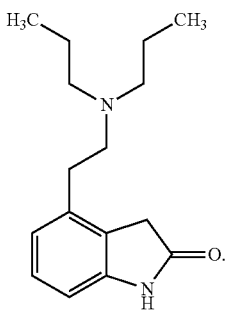

As used herein, the term "D3 receptor agonist" means a substance having the function of acting on a D3 receptor. Examples of the D3 receptor agonist include piribedil, rotigotine, PD1289077, OH-DPAT and a derivative thereof, as well as a pharmacologically acceptable salt thereof.

Rotigotine is represented by the formula:

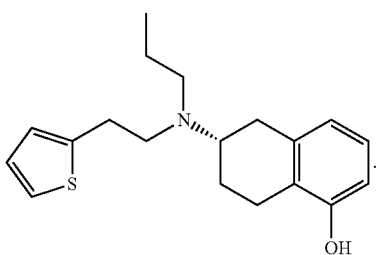 [SMILES: CCCN(CCc1cccs1)[C@H]1CCc2c(O)cccc2C1]

As used herein, the term "D4 receptor agonist" means a substance having the function of acting on a D4 receptor. Examples of the D4 receptor agonist include flibanserin, ABT724, PD168077, CP226269 and a derivative thereof, as well as a pharmacologically acceptable salt thereof.

Flibanserin is represented by the formula:

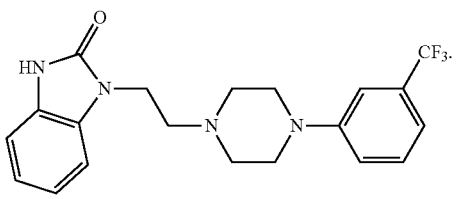 [SMILES: O=c1[nH]c2ccccc2n1CCN1CCN(c2cccc(C(F)(F)F)c2)CC1]

As used herein, the term "histamine receptor antagonist" means a substance having the function of preventing histamine from acting on a receptor, and includes, for example, a H1 receptor antagonist, and a H2 receptor antagonist.

As used herein, the term "H1 receptor antagonist" means a substance having the function of preventing histamine from acting on a H1 receptor. Examples of the H1 receptor antagonist include ketanserin, thonzylamine, mepyramine, tripelenamine, dimethindene, clemastine, bamipine, isothipendyl, chlorphenoxamine, dimetotiazine, chlorpromazine, hydroxyzine, opipramol, betahistine, cinnarizine, levocabastine, antazoline, diphenylpyraline, carbinoxamine, doxylamine, alimemazine, cyclizine, meclozine, levocetirizine, cyproheptadine, phenindamine, triprolidine, azatadine, astemizole, terfenadine, acrivastine, ebastine, desloratadine, rupatadine, bilastine, mizolastine, noberastine, rocastine, temelastine, bepotastine, diphenhydramine, chlorpheniramine, ketotifen, promethazine, cyproheptadine, epinastine, olopatadine, bepotastine, astemizole, emedastine, mequitazine, oxatomide, loratadine, fexofenadine, cetirizine, azelastine, and a derivative thereof, as well as a pharmacologically acceptable salt thereof.

Diphenhydramine is represented by the formula:

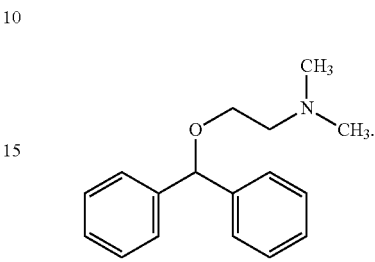

As used herein, the term "H2 receptor antagonist" means a substance having the function of preventing histamine from acting on a H2 receptor. Examples of the H2 receptor antagonist include cimetidine, ranitidine, famotidine, nizatidine, roxatidine, lafutidine, and a derivative thereof, as well as a pharmacologically acceptable salt thereof.

Famotidine is represented by the formula:

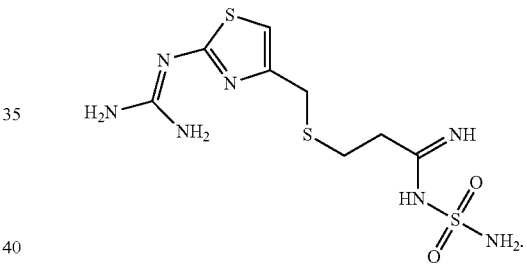

As used herein, the term "histamine receptor agonist" means a substance having the function of acting on a histamine receptor, and includes, for example, a H1 receptor agonist, a H3 receptor agonist, and a H4 receptor agonist.

As used herein, the term "H1 receptor agonist" means a substance having the function of acting on a H1 receptor. Examples of the H1 receptor agonist include 2-pyridylethylamine, 2-thiazolylethylamine and a derivative thereof, as well as a pharmacologically acceptable salt thereof.

2-Pyridylethylamine is represented by the formula:

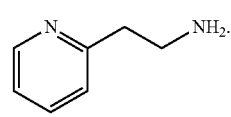

As used herein, the term "H3 receptor agonist" means a substance having the function of acting on a H3 receptor. Examples of the H3 receptor agonist include imethridine, imetit, immepip, α-methylhistamine, proxyfan, and a derivative thereof, as well as a pharmacologically acceptable salt thereof.

Proxyfan is represented by the formula:

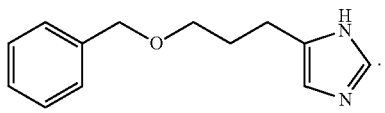 [SMILES: c1ccc(COCCCc2cnc[nH]2)cc1 ; "."]

As used herein, the term "H4 receptor agonist" means a substance having the function of acting on a H4 receptor. Examples of the H4 receptor agonist include 4-methylhistamine, VUF8430, immepip and a derivative thereof, as well as a pharmacologically acceptable salt thereof.

4-Methylhistamine is represented by the formula:

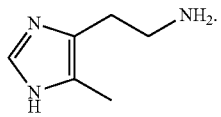

As used herein, the term "serotonin receptor antagonist" means a substance having the function of preventing serotonin from acting on a receptor, and includes, for example, a 5-HT2 receptor antagonist, a 5-HT4 receptor antagonist, a 5-HT6 receptor antagonist, and a 5-HT7 receptor antagonist.

As used herein, the term "5-HT2 receptor antagonist" means a substance having the function of preventing serotonin from acting on a 5-HT2 receptor. Examples of the 5-HT2 receptor antagonist include pizotifen, risperidone, olanzapine, quetiapine, aripiprazole, blonanserin, clozapine, paliperidone, ritanserin, yohimbine, mesulergine, agomelatine, cyclobenzaprine, sarpogrelate, methysergide, ketanserin, and a derivative thereof, as well as a pharmacologically acceptable salt thereof.

Olanzapine is represented by the formula:

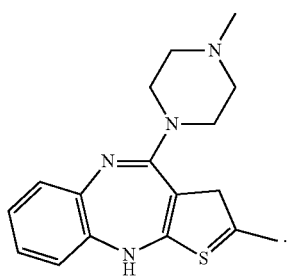

As used herein, the term "5-HT4 receptor antagonist" means a substance having the function of preventing serotonin from acting on a 5-HT4 receptor. Examples of the 5-HT4 receptor antagonist include piboserod, GR113808, GR125487, RS39604, SB204070 and a derivative thereof, as well as a pharmacologically acceptable salt thereof.

Piboserod is represented by the formula:

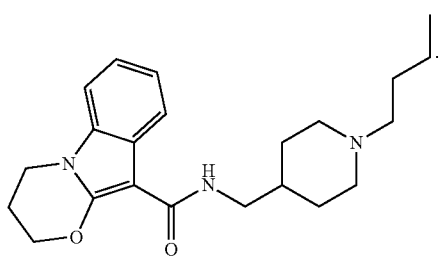 [SMILES: CCCCN1CCC(CNC(=O)c2c3n(c4ccccc24)CCCO3)CC1 ; "."]

As used herein, the term "5-HT6 receptor antagonist" means a substance having the function of preventing serotonin from acting on a 5-HT6 receptor. Examples of the 5-HT6 receptor antagonist include cerlapirdine, clozapine and a derivative thereof, as well as a pharmacologically acceptable salt thereof.

Cerlapirdine is represented by the formula:

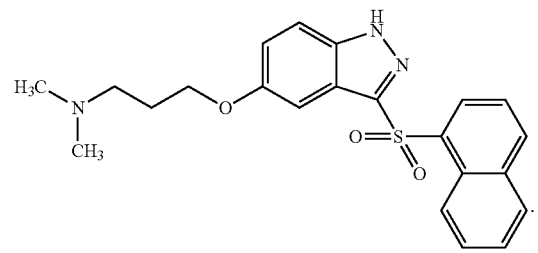 [SMILES: CN(C)CCCOc1ccc2[nH]nc(S(=O)(=O)c3cccc4ccccc34)c2c1]

As used herein, the term "5-HT7 receptor antagonist" means a substance having the function of preventing serotonin from acting on a 5-HT7 receptor. Examples of the 5-HT7 receptor antagonist include lurasidone, metergoline, and a derivative thereof, as well as a pharmacologically acceptable salt thereof.

Metergoline is represented by the formula:

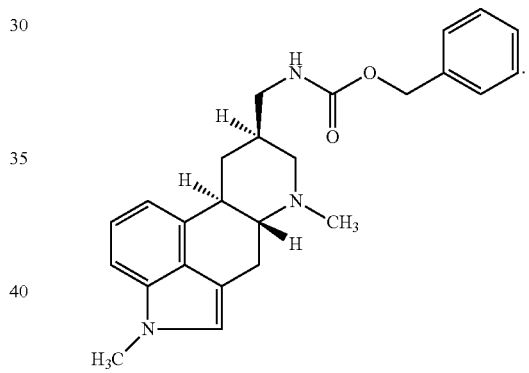

As used herein, the term "serotonin receptor agonist" means a substance having the function of acting on a serotonin receptor, and includes, for example, a 5-HT1 receptor agonist, and a 5-HT2 receptor agonist.

As used herein, the term "5-HT1 receptor agonist" means a substance having the function of acting on a 5-HT1 receptor. Examples of the 5-HT1 receptor agonist include piclozotan, tandospirone, sumatriptan, zolmitriptan, eletriptan, rizatriptan, naratriptan, almotriptan, frovatriptan, avitriptan, ergotamine, ergot alkaloid, and a derivative thereof, as well as a pharmacologically acceptable salt thereof.

Zolmitriptan is represented by the formula:

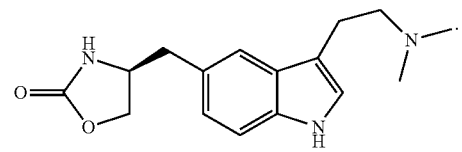 [SMILES: CN(C)CCc1c[nH]c2ccc(C[C@H]3COC(=O)N3)cc12]

As used herein, the term "5-HT2 receptor agonist" means a substance having the function of acting on a 5-HT2 receptor. Examples of the 5-HT2 receptor agonist include α-methyl-5-HT, agomelatine, norfenfluramine, meta-chlorophenylpiperazine and a derivative thereof, as well as a pharmacologically acceptable salt thereof.

Agomelatine is represented by the formula:

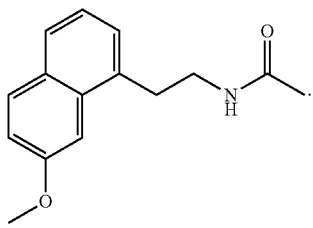 [SMILES: COc1ccc2cccc(CCNC(C)=O)c2c1]

As used herein, the term "vasopressin receptor antagonist" means a substance having the function of preventing vasopressin from acting on a receptor, and includes, for example, a V2 receptor antagonist.

As used herein, the term "V2 receptor antagonist" means a substance having the function of preventing vasopressin from acting on a V2 receptor. Examples of the V2 receptor antagonist include tolvaptan, mozavaptan, conivaptan, lixivaptan, and a derivative thereof, as well as a pharmacologically acceptable salt thereof.

Mozavaptan is represented by the formula:

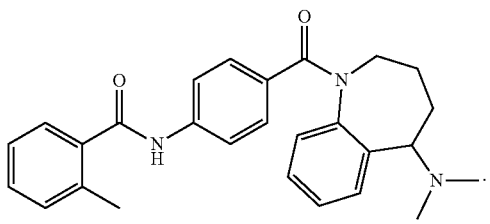 [SMILES: Cc1ccccc1C(=O)Nc1ccc(C(=O)N2CCCC(N(C)C)c3ccccc32)cc1]

As used herein, the term "vasopressin receptor agonist" means a substance having the function of acting on a vasopressin receptor, and includes, for example, a V1 receptor agonist.

As used herein, the term "V1 receptor agonist" means a substance having the function of acting on a V1 receptor. Examples of the V1 receptor agonist include vasopressin, felypressin, desmopressin, lypressin, terlipressin, ornipressin, argipressin, and a derivative thereof, as well as a pharmacologically acceptable salt thereof.

Desmopressin is represented by the formula:

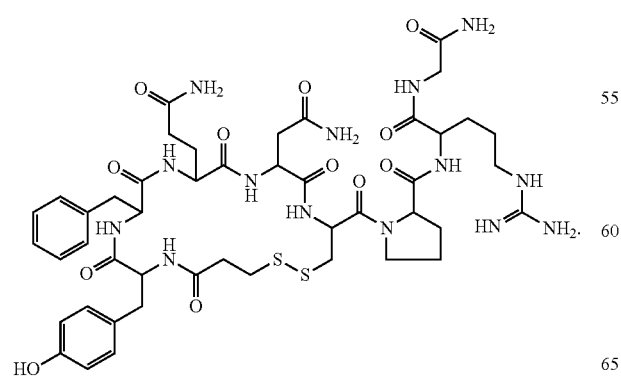

As used herein, the term "muscarine receptor antagonist" means a substance having the function of acting on a muscarine receptor, and includes, for example, a M1 receptor antagonist, a M3 receptor antagonist, and a M5 receptor antagonist.

As used herein, the term "M1 receptor antagonist" means a substance having the function of preventing acetylcholine from acting on a M1 receptor. The term "M3 receptor antagonist" means a substance having the function of preventing acetylcholine from acting on a M3 receptor. The term "M5 receptor antagonist" means a substance having the function of preventing acetylcholine from acting on a M5 receptor. Examples of the M1 receptor antagonist, and/or the M3 receptor antagonist, and/or the M5 receptor antagonist include pirenzepine, atropine, trimebutine, piperidolate, oxybutynin, tropicamide, propiverine, tolterodine, solifenacin, darifenacin, imidafenacin, oxyphencyclimine, tiotropium bromide, esoxybutynin, tiquizium, and a derivative thereof, as well as a pharmacologically acceptable salt thereof.

Oxybutynin is represented by the formula:

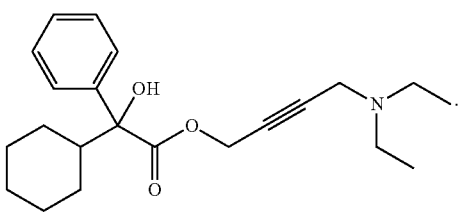 [SMILES: CCN(CC)CC#CCOC(=O)C(O)(c1ccccc1)C1CCCCC1]

As used herein, the term "muscarine receptor agonist" means a substance having the function of acting on a muscarine receptor, and includes, for example, a M1 receptor agonist, a M2 receptor agonist, a M3 receptor agonist, a M4 receptor agonist, and a M5 receptor agonist.

As used herein, the term "M1 receptor agonist" means a substance having the function of acting on a M1 receptor. The term "M2 receptor agonist" means a substance having the function of acting on a M2 receptor. The term "M3 receptor agonist" means a substance having the function of acting on a M3 receptor. The term "M4 receptor agonist" means a substance having the function of acting on a M4 receptor. The term "M5 receptor agonist" means a substance having the function of acting on a M5 receptor. Examples of the M1 receptor agonist, and/or the M2 receptor agonist, and/or the M3 receptor agonist, and/or the M4 receptor agonist, and/or the M5 receptor agonist include acetylcholine, aceclidine, alvameline, talsaclidine, xanomeline, pilocarpine, cevimeline, bethanechol, mazaticol, muscarine, and a derivative thereof, as well as a pharmacologically acceptable salt thereof.

Bethanechol is represented by the formula:

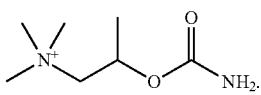

As used herein, the term "adrenalin receptor antagonist" means a substance having the function of preventing adrenalin from acting on a receptor, and includes, for example, an α1 receptor antagonist, a β1 receptor antagonist, a β2 receptor antagonist, and a β3 receptor antagonist.

As used herein, the term "α1 receptor antagonist" means a substance having the function of preventing adrenalin from acting on an α1 receptor. Examples of the α1 receptor antagonist include prazosin, doxazosin, bunazosin, trimazosin, alfuzosin, silodosin, terazosin, tamusulosin, and a derivative thereof, as well as a pharmacologically acceptable salt thereof.

Tamusulosin is represented by the formula:

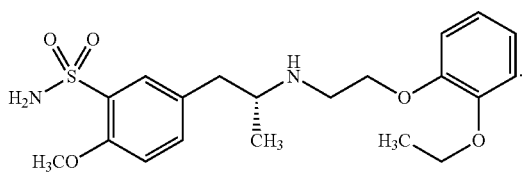 [SMILES: CCOc1ccccc1OCCN[C@H](C)Cc1ccc(OC)c(S(N)(=O)=O)c1]

As used herein, the term "β1 receptor antagonist" means a substance having the function of preventing adrenalin from acting on a β1 receptor. The term "β2 receptor antagonist" means a substance having the function of preventing adrenalin from acting on a β32 receptor. The term "β3 receptor antagonist" means a substance having the function of preventing adrenalin from acting on a β3 receptor. Examples of the β1 receptor antagonist, and/or the β2 receptor antagonist, and/or the β3 receptor antagonist include bopindolol, pindolol, timolol, dichloroisoprenaline, alprenolol, carteolol, indenolol, bunitrolol, penbutolol, propranolol, nadolol, nipradilol, tilisolol, acebutolol, celiprolol, metoprolol, atenolol, bisoprolol, betaxolol, practolol, bevantolol, butoxamine, carvedilol, amosulalol, arotinolol, labetalol, and a derivative thereof, as well as a pharmacologically acceptable salt thereof.

Propranolol is represented by the formula:

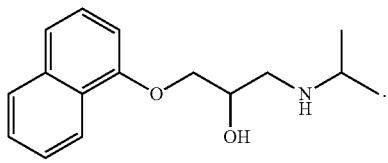 [SMILES: CC(C)NCC(O)COc1cccc2ccccc12]

As used herein, the term "angiotensin receptor agonist" means a substance having the function of acting on an angiotensin receptor, and includes, for example, an AT2 receptor agonist.

As used herein, the term "adrenalin receptor agonist" means a substance having the function of acting on an adrenalin receptor, and includes, for example, an α1 receptor agonist, and an α2 receptor agonist.

As used herein, the term "α1 receptor agonist" means a substance having the function of acting on an α1 receptor. The term "α2 receptor agonist" means a substance having the function of acting on an α2 receptor. Examples of the α1 receptor agonist, and/or the α2 receptor agonist include norepinephrine, norfenefrine, etilefrine, naphazoline, phenylephrine, midodrine, methoxamine, oxedrine, metaraminol, arbutamine, ephedrine, oxymetazoline, tetryzoline, xylometazoline, tramazoline, pseudoephidrene, dipivefrine, amidephrine, methylephedrine, rilmenidine, brimonidine, medetomidine, xylazine, tizanidine, guanfacine, methyldopa, guanabenz, and a derivative thereof, as well as a pharmacologically acceptable salt thereof.

Xylazine is represented by the formula:

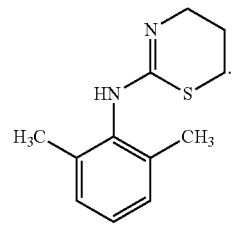

As used herein, the term "angiotensin receptor agonist" means a substance having the function of acting on an angiotensin receptor, and includes, for example, an AT2 receptor agonist.

As used herein, the term "AT2 receptor agonist" means a substance having the function of acting on an AT2 receptor. Examples of the AT2 receptor agonist include novokinin, angiotensin and a derivative thereof, as well as a pharmacologically acceptable salt thereof.

Angiotensin is represented by the formula:

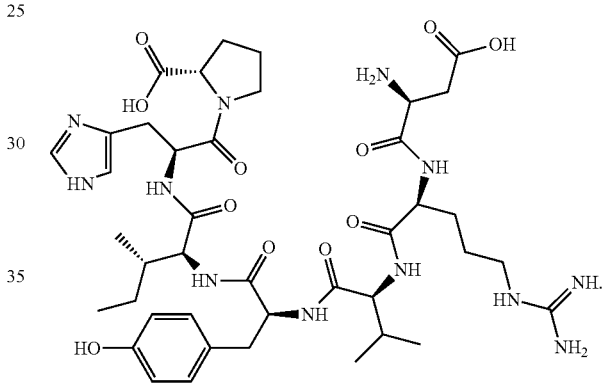

As used herein, the term "GABA receptor agonist" means a substance having the function of acting on a GABA receptor, and includes, for example, a $GABA_B$ receptor agonist.

As used herein, the term "$GABA_B$ receptor agonist" means a substance having the function of acting on a $GABA_B$ receptor. Examples of the $GABA_B$ receptor agonist include baclofen, γ-aminobutyric acid, arbaclofen and a derivative thereof, as well as a pharmacologically acceptable salt thereof.

Baclofen is represented by the formula:

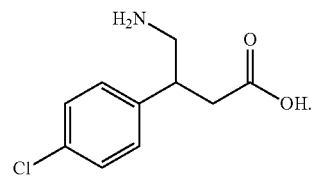 [SMILES: NCC(CC(=O)O)c1ccc(Cl)cc1]

As used herein, the term "thrombin receptor antagonist" means a substance having the function of preventing thrombin from acting on a receptor, and includes, for example, a PAR-1 receptor antagonist.

As used herein, the term "PAR-1 receptor antagonist" means a substance having the function of preventing thrombin from acting on a PAR-1 receptor. Examples of the PAR-1 receptor antagonist include vorapaxar, atopaxar, FR171113, RWJ56110, dabigatran, dabigatran etexilate, melagatran, ximelagatran, hirudin, hirulog, argatroban and a derivative thereof, as well as a pharmacologically acceptable salt thereof.

Vorapaxar is represented by the formula:

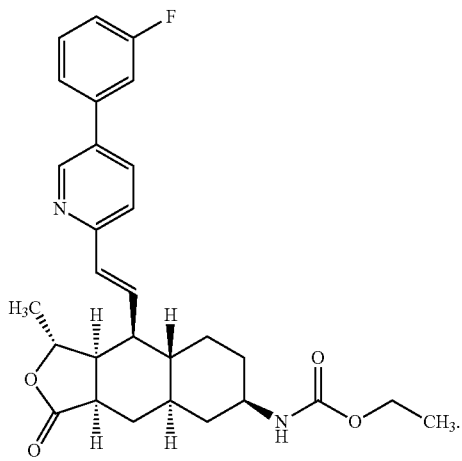 [SMILES: CCOC(=O)N[C@@H]1CC[C@@H]2[C@@H](C1)C[C@H]1C(=O)O[C@H](C)[C@H]1[C@H]2/C=C/c1ccc(-c2cccc(F)c2)cn1]

As used herein, the term "thrombin receptor agonist" means a substance having the function of acting on a thrombin receptor, and includes, for example, a PAR-1 receptor agonist.

As used herein, the term "PAR-1 receptor agonist" means a substance having the function of acting on a PAR-1 receptor. Examples of the PAR-1 receptor agonist include TRAP-6, TRAP-14, NAT6-$NH_2$ and a derivative thereof, as well as a pharmacologically acceptable salt thereof.

TRAP-6 is represented by the formula:

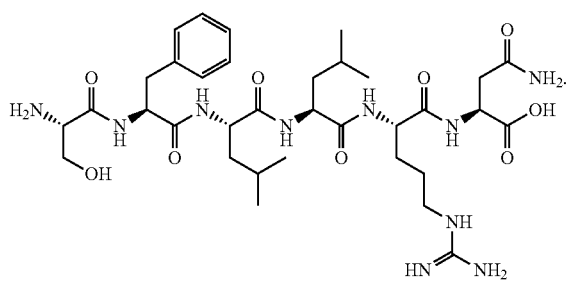 [SMILES: CC(C)C[C@H](NC(=O)[C@H](CC(C)C)NC(=O)[C@H](Cc1ccccc1)NC(=O)[C@@H](N)CO)C(=O)N[C@@H](CCCNC(=N)N)C(=O)N[C@@H](CC(N)=O)C(=O)O]

As used herein, the term "opioid receptor agonist" means a substance having the function of acting on an opioid receptor. Examples of the opioid receptor agonist include trimebutine, alvimopan, morphine, oxycodone, dihydrocodeine, diamorphine, pethidine, pentazocine, buprenorphine, butorphanol, nalbuphine, tilidine, dezocine, meptazinol, tapentadol, naltrexone, methadone, ethylmorphine, hydrocodone, acetyldihydrocodeine, nalorphine, loperamide, remoxipride, opipramol, and a derivative thereof, as well as a pharmacologically acceptable salt thereof.

Buprenorphine is represented by the formula:

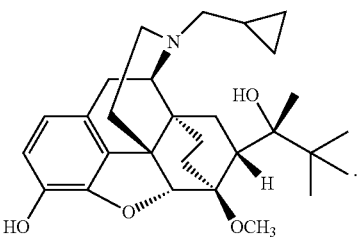 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

As used herein, the term "leukotriene receptor antagonist" means a substance having the function of preventing leukotriene from acting on a receptor, and includes, for example, a CysLT1 receptor antagonist, and a CysLT2 receptor antagonist.

As used herein, the term "CysLT1 receptor antagonist" means a substance having the function of preventing leukotriene from acting on a CysLT1 receptor. The term "CysLT2 receptor antagonist" means a substance having the function of preventing leukotriene from acting on a CysLT2 receptor. Examples of the CysLT1 receptor antagonist, and/or the CysLT2 receptor antagonist include montelukast, zafirlukast, pranlukast, and a derivative thereof, as well as a pharmacologically acceptable salt thereof. Examples of the pharmacologically acceptable salt of montelukast include montelukast sodium and the like.

Montelukast sodium is represented by the formula:

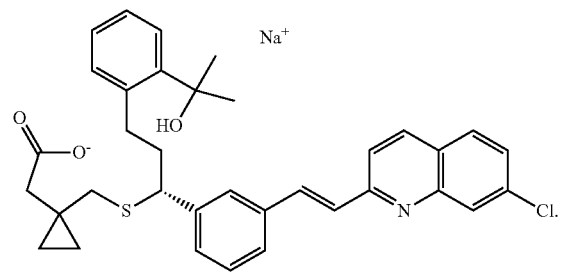 [SMILES: CC(C)(O)c1ccccc1CC[C@@H](SCC1(CC(=O)[O-])CC1)c1cccc(/C=C/c2ccc3ccc(Cl)cc3n2)c1 ; [Na+]]

As used herein, the term "leukotriene receptor agonist" means a substance having the function of acting on a leukotriene receptor, and includes, for example, a BLT receptor agonist.

As used herein, the term "BLT receptor agonist" means a substance having the function of acting on a BLT receptor. Examples of the BLT receptor agonist include leukotriene B4, CAY10583 and a derivative thereof, as well as a pharmacologically acceptable salt thereof.

Leukotriene B4 is represented by the formula:

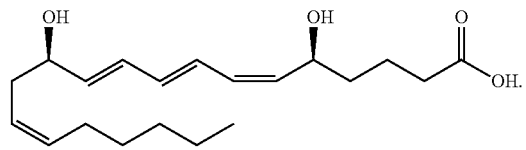 [SMILES: CCCCC/C=C\C[C@@H](O)/C=C/C=C/C=C\[C@@H](O)CCCC(=O)O]

As used herein, the term "ADP receptor agonist" means a substance having the function of acting on an ADP receptor. Examples of the ADP receptor agonist include adenosine diphosphate, and a derivative thereof, as well as a pharmacologically acceptable salt thereof.

Adenosine diphosphate is represented by the formula:

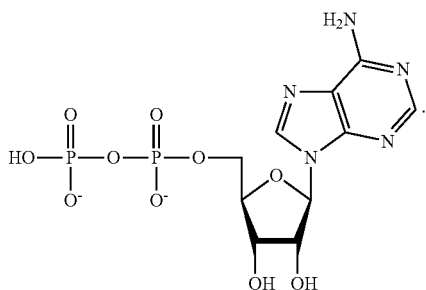

As used herein, the term "melatonin receptor agonist" means a substance having the function of acting on a melatonin receptor. Examples of the melatonin receptor agonist include melatonin, perlapine, tasimelteon, and a derivative thereof, as well as a pharmacologically acceptable salt thereof.

Melatonin is represented by the formula:

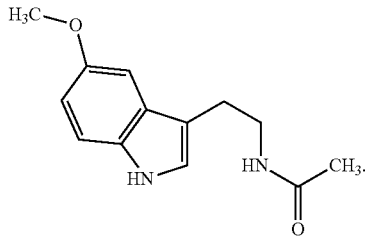 [SMILES: COc1ccc2[nH]cc(CCNC(C)=O)c2c1]

As used in the present specification, the term "somatostatin receptor agonist" means a substance having the function of acting on a somatostatin receptor. Examples of the somatostatin receptor agonist include somatostatin, somatostatin-14, octreotide, and a derivative thereof, as well as a pharmacologically acceptable salt thereof.

Octreotide is represented by the formula:

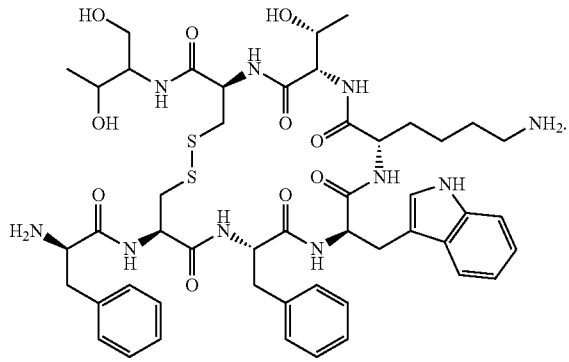 [SMILES: CC(O)C(CO)NC(=O)[C@@H]1CSSC[C@H](NC(=O)[C@H](N)Cc2ccccc2)C(=O)N[C@@H](Cc2ccccc2)C(=O)N[C@H](Cc2c[nH]c3ccccc23)C(=O)N[C@@H](CCCCN)C(=O)N[C@@H]([C@@H](C)O)C(=O)N1]

As used herein, the term "cannabinoid receptor agonist" means a substance having the function of acting on a cannabinoid receptor. Examples of the cannabinoid receptor agonist include dronabinol, nabilone, levonantradol, otenabant, GW833972A, GW405833, and a derivative thereof, as well as a pharmacologically acceptable salt thereof.

Dronabinol is represented by the formula:

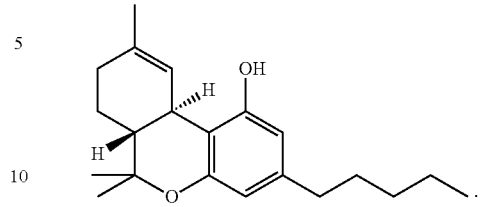

As used herein, the term "sphingosine-1 phosphate receptor agonist" means a substance having the function of acting on a sphingosine-1 phosphate receptor. Examples of the sphingosine-1 phosphate receptor agonist include fingolimod, ponesimod, RPC-1063, ONO-4641, SEW2871, sphingosine-1 phosphate and a derivative thereof, as well as a pharmacologically acceptable salt thereof.

Fingolimod is represented by the formula:

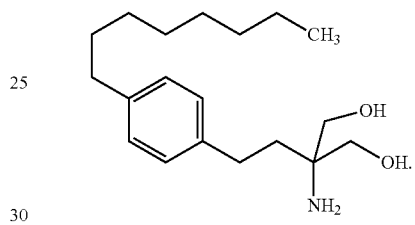

As used herein, the term "metabotropic glutamate receptor agonist" means a substance having the function of acting on a metabotropic glutamate receptor, and includes, for example, an mGluR2 receptor agonist, an mGluR3 receptor agonist, an mGluR4 receptor agonist, an mGluR6 receptor agonist, an mGluR7 receptor agonist, and an mGluR8 receptor agonist.

As used herein, the term "mGluR2 receptor agonist" means a substance having the function of acting on an mGluR2 receptor. The term "mGluR3 receptor agonist" means a substance having the function of acting on an mGluR3 receptor. The term "mGluR4 receptor agonist" means a substance having the function of acting on an mGluR4 receptor. The term "mGluR6 receptor agonist" means a substance having the function of acting on an mGluR6 receptor. The term "mGluR7 receptor agonist" means a substance having the function of acting on an mGluR7 receptor. The term "mGluR8 receptor agonist" means a substance having the function of acting on an mGluR8 receptor. Examples of the mGluR2 receptor agonist, and/or the mGluR3 receptor agonist, and/or the mGluR4 receptor agonist, and/or the mGluR6 receptor agonist, and/or the mGluR7 receptor agonist, and/or the mGluR8 receptor agonist include VU0361737, VU0155041, biphenylindanone A, PBDA, L-AP4, and a derivative thereof, as well as a pharmacologically acceptable salt thereof.

VU0361737 is represented by the formula:

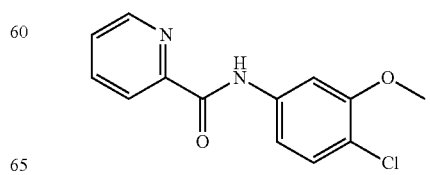

As used herein, the term "phospholipase A2 inhibitor" means a substance having the function of inhibiting the activity of phospholipase A2. Examples of the phospholipase A2 inhibitor include glycyrrhizic acid, glycyrrhetic acid, and a derivative thereof, as well as a pharmacologically acceptable salt thereof.

Glycyrrhetic acid is represented by the formula:

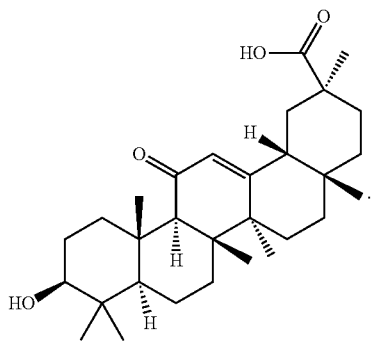

As used herein, the term "TGF-β production inhibitor" means a substance having the function of inhibiting production of TGF-β. Examples of the TGF-β production inhibitor include pirfenidone, tranilast, and a derivative thereof, as well as a pharmacologically acceptable salt thereof.

Pirfenidone is represented by the formula:

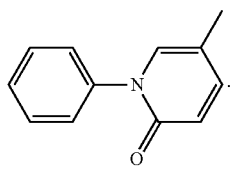

As used herein, the term "Th2 cytokine inhibitor" means a substance having the function of inhibiting production of a Th2 cytokine such as IL-4 and IL-5. Examples of the Th2 cytokine inhibitor include suplatast and a derivative thereof, as well as a pharmacologically acceptable salt thereof. Examples of the pharmacologically acceptable salt of suplatast include suplatast tosylate. In a preferable aspect of the present invention, the Th2 cytokine inhibitor is suplatast tosylate.

Suplatast tosylate is represented by the formula:

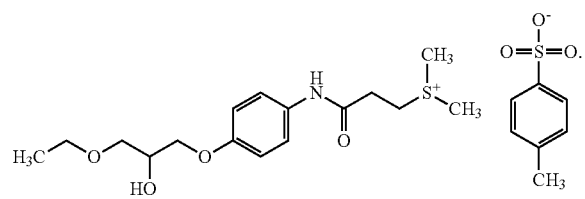 [SMILES: CCOCC(O)COc1ccc(NC(=O)CC[S+](C)C)cc1 ; Cc1ccc(S(=O)(=O)[O-])cc1]

As used herein, the term of "acid" means a Broensted acid, and includes inorganic acids and organic acids, preferably carboxylic acids, for example, fatty acid and lactic acid. As used in the present specification, the "pharmacologically acceptable acid" as a first cellular immunity induction promoter, which can be contained in the composition of the present invention, means an acid which has no harmful effect on an administration subject, and does not lose the pharmacological activity of ingredients in the composition. In a preferable aspect of the present invention, the pharmacologically acceptable acid is an organic acid, more preferably an organic compound containing carboxyl group or an organic compound containing sulfonate group, more preferably saturated or unsaturated straight or branched fatty acid in which a saturated straight chain part has 8 to 20 carbon atoms, lactic acid, malic acid, salicylic acid, maleic acid, citric acid, or an organic compound containing sulfonate group, more preferably saturated or unsaturated straight or branched fatty acid in which a saturated straight chain part has 8 to 16 carbon atoms, lactic acid, malic acid, salicylic acid, maleic acid, citric acid, or an organic compound containing sulfonate group, further preferably fatty acid selected from the group consisting of decanoic acid, lauric acid, myristic acid, isostearic acid and oleic acid, or lactic acid, salicylic acid, citric acid or methanesulfonic acid.

As used herein, the "pharmacologically acceptable salt" which can be contained in the composition of the present invention means a salt which has no harmful effect on an administration subject, and does not lose the pharmacological activity of ingredients in the composition, and includes inorganic acid salts (e.g. hydrochloride and phosphate), organic acid salts (e.g. acetate, phthalate, and TFA salt), metal salts (alkali metal salts (e.g. sodium salt and potassium salt), alkaline earth metal salts (e.g. calcium salt and magnesium salt), aluminum salt etc.), amine salts (triethylamine salt, benzylamine salt, diethanolamine salt, t-butylamine salt, dicyclohexylamine salt, arginine salt, dimethylammonium salt, ammonium salt etc.), but is not limited to them.

As used in the present specification, the term "immunomodulatory small molecule drug" means a substance which activates or suppresses immune cells such as a T cell, a NK cell, a macrophage and the like, and which does not correspond to any of the aforementioned TLR ligand, cyclic dinucleotide, helper peptide, immunomodulatory small molecule drug, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-β production inhibitor, and Th2 cytokine inhibitor. Examples of the immunomodulatory small molecule drug include bestatin, pidotimod, levamisole, golotimod, forphenicinol, and a derivative thereof, as well as a pharmacologically acceptable salt thereof. Examples of the pharmacologically acceptable salt of levamisole include levamisole hydrochloride and the like.

Bestatin is represented by the formula:

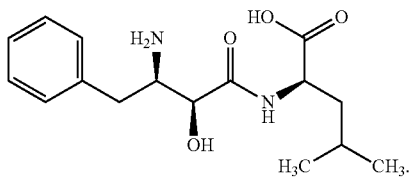 [SMILES: CC(C)C[C@@H](NC(=O)[C@@H](O)[C@H](N)Cc1ccccc1)C(=O)O]

Pidotimod is represented by the formula:

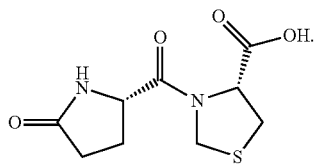 [SMILES: O=C1CC[C@@H](C(=O)N2CSC[C@H]2C(=O)O)N1]

Levamisole hydrochloride is represented by the formula:

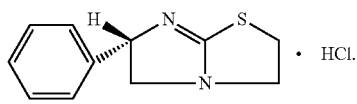

In the present invention, the immunomodulatory small molecule drug is usually a compound having the molecular weight of less than 1000, preferably less than 500. In a preferable aspect of the present invention, the immunomodulatory small molecule drug is one or more compounds selected from the group consisting of bestatin, pidotimod and levamisole hydrochloride.

As described above, the inventors have found that, among a variety of cellular immunity induction promoters, a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor are particularly suitable for transdermally administering the WT1 peptide antigen and/or the modified WT1 peptide antigen and, therefore, in one aspect, a second cellular immunity induction promoter which can be used together with a pharmacologically acceptable acid or a pharmacologically acceptable salt thereof in the present invention is selected from one or more kinds of them. As a method of quantitatively measuring induction of cellular immunity, a variety of methods have been developed, and one or more of them, for example, the ELISPOT method described in Examples may be used.

As used herein, the non-invasive administration means administration without actively giving physical irritation and/or chemical irritation, preferably without giving physical irritation (e.g. without giving irritation by tape stripping or microneedle) to a skin.

As used herein, the term "mildly irritating condition" means a condition under which irritation to be given to the skin is lower than the irritation generally given in order to improve the skin permeability of the antigen contained in conventional vaccines, or a condition under which irritation is not given to the skin at all. In general, physical and/or chemical stimulation is given to the skin before or simultaneously with the transdermal administration of a conventional vaccine composition so that the antigen can penetrate through the skin. In a preferable aspect of this invention, examples of the mildly irritating condition include a condition of low physical irritation and a condition of low chemical irritation. The condition of low physical irritation is, for example, a condition under which transepidermal water loss (TEWL) (g/h·m$^2$) of a model animal for skin irritation evaluation is 50 or less, preferably 45 or less, more preferably 40 or less, even more preferably 35 or less, still more preferably 30 or less. Since the TEWL level is about 2 (g/h·m$^2$) in the non-treated skin, the TEWL level before the administration is 2 (g/h·m$^2$) or more. The condition of low chemical irritation is, for example, a condition under which the thymic stromal lymphopoietin (TSLP) level (pg/mg protein) in the skin of the model animal for skin irritation evaluation is 10000 or less, preferably 9000 or less, more preferably 8000 or less, further preferably 7000 or less. Since the TSLP level is about 1 (pg/mg protein) in a non-treated skin, the TSLP level at completion of the administration of the vaccine composition exceeds 1 (pg/mg protein), preferably exceeds 2 (pg/mg protein), more preferably exceeds 3 (pg/mg protein). The "Thymic stromal lymphopoietin (TSLP)" is a cytokine which participates in differentiation and recruitment of a T cell, and can be utilized as an index of the degree of skin irritation in the present invention. Greater TSLP value means stronger skin irritation. Examples of means for attaining the condition of low physical irritation include not conducting the conventional pre-treatment of the skin before the administration such as not conducting tape stripping, microneedle puncture or the like before the administration. Examples of means for attaining the condition of low chemical irritation include avoiding administration of an irritating chemical ingredient such as ethanol, a surfactant or the like at a certain amount or more. The procedure for attaining the mildly irritating condition can be determined by using a model animal for skin irritation evaluation, and the determined procedure can be applied to the subject to be treated by the vaccine composition, for example, a human subject.

As used herein, the term "cancer" means a cancer associated with abnormal expression, for example, overexpression of a WT1 gene. Examples of cancer may include hematopoietic tumors or solid cancers. Examples of the hematopoietic tumors associated with abnormal expression of the WT1 gene include, but are not limited to, leukemia such as acute myelocytic leukemia, acute lymphocytic leukemia and chronic myelocytic leukemia, myelodysplastic syndrome, multiple myeloma, as well as malignant lymphoma such as non-Hodgkin's lymphoma. Examples of the solid cancers associated with abnormal expression of the WT1 gene include, but are not limited to, lung cancer, breast cancer, stomach cancer, large intestine/rectum cancer, germ cell cancer, liver cancer, skin cancer, pancreas cancer, bile duct cancer, head and neck squamous cell cancer, thyroid cancer, kidney cancer, bladder cancer, prostate cancer, ovarian cancer, uterine cancer, cervical cancer, bone soft tissue sarcoma, malignant melanoma, malignant mesothelioma, testicular germ cell tumor and malignant glioma.

As used herein, the term "abnormal expression of a gene" means that the expression level of the gene in a cell is increased or decreased remarkably, for example, by 2 times or more such as 4 times or more, as compared with the other cells in the same tissue. The term "overexpression" means that the abnormal expression is an increase in the expression level. The expression level of a gene can be easily measured using any method well-known in the art.

As used herein, the term "subject" means any animal having the WT1 gene whose immune response can be induced by the transdermal administration of a cancer vaccine composition for transdermal administration at a practical stage. Typically the subject may be a mammal such as a human, mouse, rat, dog, cat, rabbit, horse, cow, sheep, pig, goat, monkey, chimpanzee or the like. A particularly preferable subject is human.

As used herein, the term "model animal for immunological evaluation" means a model animal for evaluating the property of a cancer vaccine composition for transdermal administration immunity. Specifically, it means a model animal for evaluating the property of inducing cellular immunity. The model animal for immunological evaluation should be delected in view of compatibility between the antigen in the vaccine composition to be exalated and the MHC class I molecule of the animal. An animal model suitable for evaluating the property of the vaccine composition to induce cellular immunity should be used. For example, in the case of a vaccine composition comprising a HLA-A*24 type MHC restricted class I peptide, the property may be evaluated by a BALB/c mouse. In the case of a vaccine composition comprising a HLA-A*02 type MHC restricted peptide, the property may be evaluated in a genetically modified mouse by which immunity induction by the HLA-A*02 type MHC restricted peptide can be evaluated. In the case of a vaccine composition comprising other HLA type MHC restricted peptide, the property is evaluated by an animal by which immunity induction by the HLA type MHC restricted peptide can be evaluated. In the case of a vaccine composition comprising a protein antigen, the property is evaluated by an animal having MHC compatible with a class I epitope to be used to induce immunity, among various class I epitopes included in the an amino acid sequence of the protein antigen. In addition, in the case of a cancer vaccine composition for transdermal administration using Db126 peptide which is compatible with not only HLA-A*02 type but also MHC-H-2Db type, not only a genetically modified mouse by which immunity induction by the HLA-A*0201 type MHC restricted peptide can be evaluated, but also a C57BL/6 mouse which is an animal having MHC-H-2 Db type can be used as the model animal for immunological evaluation. When the hair of the animal is cut to ensure the place for transdermal administration, the animal should be used after it is recovered from the skin damage caused by the hair cut.

As used herein, the term "model animal for skin irritation evaluation" means a model animal for evaluating transepidermal water loss (TEWL) as an index of physical irritation of the skin, or a model animal for evaluating TSLP as an index of the skin irritation property of a cancer vaccine composition for transdermal administration. Regardless of the kind of the antigen contained in the cancer vaccine composition for transdermal administration, C57BL/6 mouse may be used as model animal for skin irritation evaluation. When the hair of the animal is cut to ensure the place for the transdermal administration, the animal should be used after it is recovered from the skin damage caused by the hair cut.

II. Cancer Vaccine Composition for Transdermal Administration

It has already been revealed that WT1 peptides and/or the modified WT1 peptides are useful as a cancer vaccine (e.g. Patent Document 1).

As used herein, the term composition "for transdermal administration" may be provided in any preparation or formulation which is usually used for the transdermal administration, for example, a liquid formulation for external use such as a liniment formulation or a lotion formulation, a spray formulation for external use such as an aerosol formulation, an ointment formulation, a plaster formulation, a cream formulation, a gel formulation, or a patch formulation such as a tape preparation or a cataplasm formulation. Grouping, definition, nature, production process and the like of these preparations or formulation are well-known in the art. For example, see Japanese Pharmacopoeia $16^{th}$ edition. A composition for transdermal administration suitable in the present invention is in a form of a cream formulation, a liquid formulation for external use or a tape preparation.

Examples of the base for the liniment formulation include water; alcohols such as ethanol and propylene glycol; fat oils such as hard paraffin, soft paraffin, liquid paraffin, glycerin, paraffin oil, beeswax and metal soap; mucilage; natural oils (e.g. almond oil, corn oil, peanut oil, castor oil, olive oil, or a derivative thereof (such as polyoxyl castor oil)); mutton tallow or a derivative thereof, fatty acids and/or esters (e.g. stearic acid, oleic acid, isopropyl myristate), as well as a mixture thereof.

The lotion formulation is a preparation in which the active ingredient is finely and homogenously dispersed in an aqueous liquid, and there are a suspending lotion formulation, and an emulsified lotion formulation. Examples of the suspending agent include gum arabic, sodium alginate, carboxymethylcellulose sodium, methylcellulose, bentonite and the like. Examples of the emulsifying agent include sodium lauryl sulfate, sorbitan fatty acid ester and the like.

For example, as an ointment base, hydrophobic base such as fats or oils, waxes and hydrocarbon compounds can be generally used. Specifically, examples of the ointment base include mineral bases such as yellow vaseline, white vaseline, paraffin, liquid paraffin, plastibase, silicone and the like, and animal or plant bases such as beeswax, animal or vegetable fat or oil and the like.

Examples of the base for cream formulation include water/oil type bases such as hydrophilic ointment, vanishing cream and the like; and oil/water type bases such as hydrophilic vaseline, purified lanolin, Aquahole, Eucerin, Neocerin, hydrous lanolin, cold cream, hydrophilic plastibase and the like.

As a gel base, for example, the followings can be used: a carboxyvinyl polymer, a gel base, a fat-free ointment, polyvinylpyrrolidone, polyvinyl alcohol, sodium polyacrylate, carboxymethylcellulose, starch, xanthan gum, karaya gum, sodium alginate, methylcellulose, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, a carboxyvinyl polymer, tragacanth, gum arabic, tara gum, tamarind seed gum, psyllium seed gum, agar, gellan gum, glucomannan, locust bean gum, guar gum, carrageenan, dextrin, dextran, amylose, carboxymethylcellulose potassium, carboxymethylcellulose sodium, carboxymethylcellulose calcium, pullulan, chitosan, sodium carboxymethyl starch, plantago testa, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate/methacrylic acid/methyl methacrylate copolymer, ethyl acrylate/methyl methacrylate copolymer, polyvinylacetal diethylaminoacetate, casein, alginic acid alkyl ester, gelatin, polyethylene glycol and the like as a hydrogel base.

Examples of the base for a cataplasm preparation include gelatin, carboxymethylcellulose sodium, methylcellulose, sodium polyacrylate, kaolin, polyvinyl alcohol, polyvinylpyrrolidone, glycerin, propylene glycol, water and the like.

For example, a tape preparation comprises an adhesive layer comprising an acrylic adhesive, a natural rubber adhesive, a synthetic rubber adhesive (including rubber elastomer such as synthetic isoprene rubber, polyisobutylene (PIB), styrene-butadiene rubber, styrene-isoprene-styrene (SIS) rubber etc.), a silicone adhesive, a vinyl ester adhesive, a vinyl ether adhesive or the like, and a support which supports the adhesive layer. Optionally, the preparation may further contain a release liner which covers the adhesive layer to avoid exposure thereof before use and can be easily peeled from the adhesive layer upon use.

The amount of the WT1 peptide and/or the modified WT1 peptide, the pharmacologically acceptable acid or a pharmacologically acceptable salt thereof, and the cellular immunity induction promoter in the cancer vaccine composition for transdermal administration of the present invention is not particularly limited. In one aspect, the cancer vaccine composition for transdermal administration of the present invention contains the WT1 peptide and/or the modified WT1 peptide preferably in an amount of 0.01 to 40% by weight, more preferably 0.1 to 30% by weight based on the total weight of the composition. In one aspect, the cancer vaccine composition for transdermal administration of the present invention contains the pharmacologically acceptable acid or a pharmacologically acceptable salt thereof preferably in an amount of 0.001 to 30% by weight, more preferably 0.01 to 20% by weight based on the total weight of the composition. When the cancer vaccine composition for transdermal administration of the present invention contains a cellular immunity induction promoter, the cellular immunity induction promoter is contained preferably in an amount of 0.001 to 30% by weight, more preferably 0.01 to 20% by weight based on the total weigh of the composition.

When the cancer vaccine composition for transdermal administration of the present invention is provided in the form of a tape preparation, an adhesive layer of the tape preparation (hereinafter, also referred to as "tape preparation of the present invention") comprises an antigen and, optionally, further comprises a cellular immunity induction promoter. In one aspect, the adhesive layer of the tape preparation of the present invention comprises an antigen preferably in an amount of 0.01 to 40% by weight, more preferably 0.1 to 30% by weight based on the total weight of the adhesive layer. When the adhesive layer of the tape preparation of the present invention comprises a cellular immunity induction promoter, the cellular immunity induction promoter is comprised preferably in an amount of 0.001 to 30% by weight, more preferably 0.01 to 20% by weight based on the total weight of the adhesive layer.

An adhesive which is to form the adhesive layer of the tape preparation of the present invention is not particularly limited, and examples thereof include acrylic adhesives consisting of an acrylic polymer; rubber adhesives comprising a rubber elastomer such as a styrene-diene-styrene block copolymer (e.g. styrene-isoprene-styrene block copolymer, styrene-butadiene-styrene block copolymer etc.), polyisoprene, polyisobutylene, butyl rubber, polybutadiene and the like; silicone adhesives such as silicone rubber, dimethylsiloxane base, diphenylsiloxane base and the like; vinyl ether adhesives such as polyvinyl methyl ether, polyvinyl ethyl ether, polyvinyl isobutyl ether and the like; vinyl ester adhesives such as vinyl acetate-ethylene copolymer and the like; and polyester adhesives consisting of a carboxylic acid component such as dimethyl terephthalate, dimethyl isophthalate, dimethyl phthalate, and a polyhydric alcohol component such as ethylene glycol. A particularly preferable adhesive is an acrylic adhesive, a rubber adhesive, and a silicone adhesive. These adhesives are contained in the adhesive layer preferably in an amount of 10 to 90% by weight, more preferably 20 to 80% by weight, as a solid matter thereof, based on the total weight of the adhesive layer.

Examples of the acrylic adhesive include an acrylic acid ester adhesive containing, as a main component, a polymer comprising (meth)acrylic acid C2-C18 alkyl ester as a first monomer. Examples of the (meth)acrylic acid alkyl ester (first monomer) include (meth)acrylic acid alkyl esters in which an alkyl group is a straight, branched or cyclic alkyl group having 1 to 18 carbon atoms (e.g. methyl, ethyl, propyl, butyl, pentyl, hexyl, cyclohexyl, heptyl, octyl, 2-ethylhexyl, nonyl, decyl, undecyl, dodecyl, tridecyl etc.). Preferred are (meth)acrylic acid alkyl esters in which an alkyl group is a straight, branched or cyclic alkyl group having 4 to 18 carbon atoms (e.g. butyl, pentyl, hexyl, cyclohexyl, heptyl, octyl, 2-ethylhexyl, nonyl, decyl, undecyl, dodecyl, tridecyl etc.). Further, since use of a monomer component which lowers the glass transition temperature of a polymer is suitable in order to impart adhesiveness at room temperature, (meth)acrylic acid alkyl esters in which an alkyl group is a straight, branched or cyclic alkyl group having 4 to 8 carbon atoms (e.g. butyl, pentyl, hexyl, cyclohexyl, heptyl, octyl, 2-ethylhexyl etc., preferably butyl, 2-ethylhexyl, and cyclohexyl, particularly preferably 2-ethylhexyl) are more preferable. Specifically, butyl acrylate, 2-ethylhexyl acrylate, 2-ethylhexyl methacrylate, cyclohexyl acrylate, cyclohexyl methacrylate and the like are more preferable and, among them, 2-ethylhexyl acrylate is most preferable. These (meth)acrylic acid alkyl esters (first monomer component) can be used alone, or can be used by combining two or more thereof.

In addition, the acrylic adhesive may contain a second monomer copolymerizable with the (meth)acrylic acid alkyl ester, and examples of the second monomer include monomers having a functional group which can become a crosslinking point upon use of a crosslinking agent. Examples of the functional group which can participate in a crosslinking reaction include a hydroxy group, a carboxyl group, a vinyl group and the like, and a hydroxy group and a carboxyl group are preferable. Specific examples of the monomer (second monomer component) include (meth)acrylic acid hydroxyethyl ester, (meth)acrylic acid hydroxypropyl ester, N-hydroxyalkyl(meth)acrylamide, (meth)acrylic acid, itaconic acid, maleic acid, maleic anhydride, mesaconic acid, citraconic acid, glutaconic acid and the like. Among them, from the viewpoint of easy availability, acrylic acid, methacrylic acid, and acrylic acid hydroxyethyl ester (particularly, 2-hydroxyethyl acrylate) are preferable, and acrylic acid is most preferable. These monomers (second monomer component) can be used alone, or can be used by combining two or more thereof.

Further, the acrylic adhesive may optionally contain a third monomer in addition to the second monomer. Examples of the third monomer (third monomer component) include vinyl esters such as vinyl acetate, vinyl propionate and the like; vinyl ethers such as methyl vinyl ether, ethyl vinyl ether and the like; vinyl amides such as N-vinyl-2-pyrrolidone, N-vinylcaprolactam and the like; (meth)acrylic acid alkoxy esters such as (meth)acrylic acid methoxyethyl ester, (meth)acrylic acid ethoxyethyl ester, (meth)acrylic acid tetrahydrofurfuryl ester and the like; hydroxy group-containing monomers (since this is used as a third monomer component, it is not a crosslinking point) such as hydroxypropyl (meth)acrylate, α-hydroxymethyl acrylate and the like; (meth)acrylic acid derivatives having an amide group such as (meth)acrylamide, dimethyl(meth)acrylamide, N-butyl(meth)acrylamide, N-methylol(meth)acrylamide and the like; (meth)acrylic acid aminoalkyl esters such as (meth)acrylic acid aminoethyl ester, (meth)acrylic acid dimethylaminoethyl ester, (meth)acrylic acid t-butylaminoethyl ester and the like; (meth)acrylic acid alkoxyalkylene glycol esters such as (meth)acrylic acid methoxyethylene glycol ester, (meth)acrylic acid methoxydiethylene glycol ester, (meth)acrylic acid methoxypolyethylene glycol ester, (meth)acrylic acid methoxypolypropylene glycol ester and the like; (meth)acrylonitriles; monomers having sulfonic acid such as styrenesulfonic acid, allylsulfonic acid, sulfopropyl(meth)acrylate, (meth)acryloyloxynaphthalenesulfonic acid, acrylamidemethylsulfonic acid and the like; and vinyl-group-containing monomers such as vinylpiperidone, vinylpyrimidine, vinylpiperazine, vinylpyrrole, vinylimidazole, vinyloxazole, vinylmorpholine and the like. Among them, vinyl esters, and vinyl amides are preferable, vinyl acetate is preferable as vinyl esters, and N-vinyl-2-pyrrolidone is preferable as vinyl amides. These monomers (third monomer component) can be used alone, or can be used by combining two or more thereof.

When the acrylic adhesive is a copolymer of a (meth)acrylic acid alkyl ester (first monomer component) and a vinyl monomer having a functional group which can participate in a crosslinking reaction (second monomer component), the (meth)acrylic acid alkyl ester and the vinyl monomer having a functional group which can participate in a crosslinking reaction are copolymerized by blending the components at a weight ratio of (meth)acrylic acid alkyl ester:vinyl monomer having a functional group which can participate in a crosslinking reaction of preferably 99 to 85:1 to 15, more preferably 99 to 90:1 to 10.

Further, when the acrylic adhesive is a copolymer of a (meth)acrylic acid alkyl ester (first monomer component), a vinyl monomer having a functional group which can participate in a crosslinking reaction (second monomer component), and a monomer other than them (third monomer component), the (meth)acrylic acid alkyl ester, the vinyl monomer having a functional group which can participate in a crosslinking reaction, and the monomer other than them are copolymerized by blending the components at a weight ratio of (meth)acrylic acid alkyl ester:vinyl monomer having a functional group which can participate in a crosslinking reaction:monomer other than them of preferably 40 to 94:1 to 15:5 to 50, more preferably 50 to 89:1 to 10:10 to 40.

The components may be polymerized by a known method. For example, the monomers in a solvent such as ethyl acetate may be reacted in the presence of a polymerization initiator (e.g. benzoyl peroxide, azobisisobutyronitrile etc.) at 50 to 70° C., for 5 to 48 hours.

Particularly preferable acrylic adhesives in the present invention are, for example, a copolymer of acrylic acid 2-ethylhexyl ester/acrylic acid/N-vinyl-2-pyrrolidone, a copolymer of acrylic acid 2-ethylhexyl ester/N-(2-hydroxyethyl)acrylamide/N-vinyl-2-pyrrolidone, a copolymer of acrylic acid 2-ethylhexyl ester/acrylic acid 2-hydroxyethyl ester/vinyl acetate and a copolymer of acrylic acid 2-ethylhexyl ester/acrylic acid and, more preferably, a copolymer of acrylic acid 2-ethylhexyl ester/acrylic acid/N-vinyl-2-pyrrolidone.

Optionally, these acrylic adhesives may be subjected to physical crosslinking treatment by ultraviolet irradiation, or radiation irradiation such as electron beam irradiation, or chemical crosslinking treatment using various crosslinking agents such as an isocyanate compound such as trifunctional isocyanate, organic peroxide, organic metal salt, metal alcoholate, metal chelate compound, polyfunctional compound (polyfunctional external crosslinking agent, a monomer for polyfunctional internal crosslinking such as diacrylate and dimethacrylate).

Examples of the rubber adhesive include rubber adhesives in which a rubber elastomer such as polyisobutylene/polybutene elastomer, styrene/diene/styrene block copolymer, styrene/butadiene elastomer, nitrile elastomer, chloroprene elastomer, vinylpyridine elastomer, polyisobutylene elastomer, butyl elastomer, or isoprene/isobutylene elastomer is blended. Among them, in view of solubility of the peptide and the cellular immunity induction promoter in the adhesive and the skin adhesiveness, polyisobutylene (PIB), styrene/diene/styrene block copolymer (e.g. styrene/butadiene/styrene block copolymer (SBS), styrene/isoprene/styrene block copolymer (SIS) etc.) and the like are preferably used. A mixture of two or more of those adhesives may also be used.

Further, in order to achieve a suitable adhesive force and drug solubility of the rubber adhesive, the rubber adhesive may be a mixture of two or more rubber elastomers of the same or different monomer components each having different average molecular weights. For example, with respect to polyisobutylene, a mixture of polyisobutylene of high molecular weight having an average molecular weight of 150,000 to 5,500,000, polyisobutylene of medium molecular weight having an average molecular weight of 10,000 to 150,000 and/or polyisobutylene of low molecular weight having an average molecular weight of 500 to 4,000 is preferable. In this case, it is preferable to blend polyisobutylenes of high molecular weight, medium molecular weight and low molecular weight at a weight ratio of high molecular weight:medium molecular weight:low molecular weight=10 to 80, preferably 20 to 70:0 to 90, preferably 10 to 80:0 to 80, preferably 10 to 60.

As used herein, the average molecular weight means the viscosity average molecular weight calculated from the viscosity expression of Flory, and is obtained by calculating the Staudinger index ($J_0$) from the flow time of the capillary 1 of a Ubbelohde viscometer at 20° C. by the Schulz-Blaschke expression, and using this $J_0$ value with the following expression.

$$J_0 = \eta_{sp}/c(1+0.31\eta_{sp}) \quad \text{(Schulz-Blaschke equation)}$$

$$\eta_{sp} = t/t_0 - 1 \quad \text{(Formula)}$$

t: Flow time of solution (according to Hagenbach-couette correction formula)

$t_0$: Flow time of solvent (according to Hagenbach-couette correction formula)

c: Concentration of solution (g/cm$^3$)

$$J_0 = 3.06 \times 10^{-2} \overline{Mv}^{0.65}$$

$\overline{Mv}$: Viscosity average molecular weight

In order to impart suitable adhesiveness, for example, a tackifier such as a rosin resin, a polyterpene resin, a coumarone-indene resin, a petroleum resin, a terpene-phenol resin, a xylene resin, an alicyclic saturated hydrocarbon resin or the like may be blended in the rubber adhesive. One or two or more kinds of tackifiers can be blended in an amount of 50% by weight or less, preferably 5 to 40% by weight based on the total weight of the rubber adhesive.

Examples of the silicone adhesive include silicone adhesives consisting of polyorganosiloxane adhesive, polydimethylsiloxane adhesive, polydimethyldiphenyl-siloxane adhesive. Inter alia, a commercially available silicone adhesive such as BIO PSA from Dow Corning Corporation is preferably used.

The support which supports the adhesive layer is not particularly limited, and a support that is substantially impervious to the peptide and the cellular immunity induction promoter so that the peptide, the cellular immunity induction promoter, additives or the like contained in the adhesive layer will not pass through the support and leaked from the rear surface.

As the support, for example, a single film of polyester, polyamide, poly(vinylidene chloride), polyethylene, polypropylene, poly(vinyl chloride), ethylene-ethyl acrylate copolymer, polytetrafluoroethylene, ionomer resin, metal foil or the like, or a laminate film of them can be used. Among them, in order to make adhesiveness (anchorability) between the support and the adhesive layer good, it is preferable that the support is a laminate film of a nonporous plastic film and a porous film made of the aforementioned material. In this case, it is desirable that the adhesive layer is formed on the porous film side. As such a porous film, a porous film which improves anchorability with the adhesive layer is adopted, and specific examples thereof include a paper sheet, a woven fabric, a non-woven fabric, a knitted fabric, a sheet which has been mechanically perforation-treated, and the like. Among them, from the viewpoint of handling property and the like, particularly, a paper sheet, a woven fabric and a non-woven fabric are preferable. As the porous film, in view of improvement in anchorability, softness and sticking operability of a tape preparation and the like, a porous film having a thickness in the range of 1 to 200 μm is adopted. In addition, when a woven fabric or a non-woven fabric is used as the porous film, the weight per unit area is preferably 5 to 30 g/m$^2$, more preferably 6 to 15 g/m$^2$.

Examples of a most suitable support include a laminate film of a polyester film (preferably, polyethylene terephthalate film) having a thickness of 1.5 to 6 μm, and a non-woven fabric made of polyester (preferably, polyethylene terephthalate) having a weight per unit area of 6 to 15 g/m$^2$.

In the tape preparation of the present invention, in order to protect the surface of the adhesive layer until use, it is desirable that a release liner is laminated on the adhesive surface. The release liner is not particularly limited as far as it is treated so that it has the releasing property and it can be released with a sufficiently small peeling force. For example, a film of polyester, poly(vinyl chloride), poly(vinylidene chloride), polyethylene terephthalate or the like, paper such as pure paper, glassine paper and the like, or a laminate film of pure paper or glassine paper and polyolefin may be treated with the adhesive layer and is used as the release liner. The thickness of the release liner is preferably 10 to 200 μm, more preferably 25 to 100 μm. As the release liner, polyester layer, particularly, polyethylene terephthalate layer is preferable in view of the barrier property and the cost. Further, in this case, in terms of handling property, a release liner having a thickness of around 25 to 100 μm is preferable.

It is preferable that the composition of the present invention is administered to a subject under the mildly irritating condition. Administration under the mildly irritating condition can be attained by, for example, (i) administering the composition of the present invention to a subject under such an administration condition that transepidermal water loss (TEWL) (g/h·m$^2$) evaluated in a model animal for skin irritation evaluation is 50 or less, (ii) administering to a subject the composition providing the cutaneous TSLP level (pg/mg protein) of 10000 or less evaluated in a model animal for skin irritation evaluation.

In addition, the composition of the present invention may contain an additive, if necessary. The additive is selected from, for example, isotonizing agents, antiseptics/germicides, antioxidants, resolvents, solubilizers, suspending agents, fillers, pH adjusting agents, stabilizers, absorption promoters, release rate controlling agents, coloring agents, plasticizers, crosslinking agents, adhesives and the like, or a combination of two or more kinds of them, depending on the compatibility with the main ingredient of the base, the WT1 peptide and/or the modified WT1 peptide and the cellular immunity induction promoter, intended administration regimen and the like. In addition, when the composition of the present invention is in a tape preparation, the tape preparation can contain a skin permeability enhancer as an additive.

As used herein, the term "skin permeability enhancer" means any substance which can improve an efficiency of permeation of a transdermally administered antigen through the skin, as compared with the efficiency obtained without the substance. The skin permeability enhancer is not particularly limited as far as it is liquid at room temperature (25° C.), that is, has fluidity at that temperature and has an absorption promoting effect. When the skin permeability enhancer is a mixture of two or more substances, the mixture is liquid at room temperature (25° C.), and has an absorption promoting effect. The skin permeability enhancer may be an organic liquid and preferably, a hydrophobic liquid in view of their compatibility with the adhesive layer.

Examples of skin permeability enhancers include higher alcohols such as oleyl alcohol, octyldodecanol and the like; polyhydric alcohols such as glycerin, ethylene glycol, polypropylene glycol and the like; higher fatty acids such as oleic acid, caprylic acid and the like; fatty acid esters such as isopropyl myristate, isopropyl palmitate, ethyl oleate and the like; polybasic acid esters such as diethyl sebacate, diisopropyl adipate and the like; polyhydric alcohol fatty acid esters such as diglyceryl triisostearate, monooleic acid sorbitan, dicaprylic acid propylene glycol, monolauric acid polyethylene glycol, tetraoleic acid polyoxyethylene sorbit and the like; polyoxyethylene alkyl ethers such as polyoxyethylene lauryl ether and the like; hydrocarbons such as squalane, liquid paraffin and the like; plant oils such as olive oil, castor oil and the like; silicone oils; pyrrolidones such as N-methylpyrrolidone, N-dodecylpyrrolidone and the like; sulfoxides such as decylmethyl sulfoxide and the like, and these can be used alone, or can be used by mixing two or more kinds thereof.

When the rubber or acrylic adhesive is used, a second skin permeability enhancer can be used. Specific examples of the second skin permeability enhancer include polyvinylpyrrolidone, crospovidone, polypropylene glycol, polyvinyl alcohol, carboxyvinyl polymer, hydroxypropylcellulose and the like, or a mixture thereof, but not limited to them. In a preferable aspect, the second skin permeability enhancer of the present invention is polyvinylpyrrolidone, crospovidone and/or polypropylene glycol.

From the viewpoint of skin permeability enhancement of the WT1 peptide and/or the modified WT1 peptide, a higher alcohol, more specifically, a higher alcohol having 8 to 18 (preferably 8 to 14) carbon atoms, a fatty acid ester, more specifically, a fatty acid ester of fatty acid having 8 to 18 (preferably 12 to 16) carbon atoms and a monohydric alcohol having 1 to 18 carbon atoms, a polyhydric alcohol fatty acid ester or the like, particularly, a fatty acid ester, particularly, isopropyl myristate, isopropyl palmitate, or diethyl sebacate is preferably used as the skin permeability enhancer. The amount of such a skin permeability enhancer is preferably 0.1% by weight to 70% by weight, more preferably 1% by weight to 65% by weight, more preferably 5% by weight to 60% by weight based on the total amount of the adhesive layer. When the amount of the skin permeability enhancer is 0.1% by weight or more, the high transdermal absorption promoting effect can be obtained. When the amount is 70% by weight or less, high transdermal absorbability can be obtained while suppressing reduction in an adhesive force or a cohesive force of the whole adhesive layer and, therefore, this is advantageous.

The therapeutically effective amount of the WT1 peptide and/or the modified WT1 peptide may widely vary depending on severity of the disease, age and relative health of a subject as well as other known factors. In general, satisfactory result may be obtained at one day dose of about 0.1 μg to 1 g/kg body weight. The pharmacologically acceptable acid or a pharmacologically acceptable salt thereof is administered simultaneously with an antigen, or sequentially, and preferred is simultaneous administration. The effective amount of the pharmacologically acceptable acid or a pharmacologically acceptable salt thereof can widely vary depending on a specific acid or salt to be used, the presence or absence of a cellular immunity induction promoter to be used together and the like, and satisfactory result is obtained at 0.01 μg to 1 g/kg body weight. When the cellular immunity induction promoter is used together, the cellular immunity induction promoter is administered simultaneously with the WT1 peptide and/or the modified WT1 peptide, or sequentially, and preferred is simultaneous administration. The effective amount of the cellular immunity induction promoter can widely vary depending on a specific cellular immunity induction promoter to be used, the presence or absence of other cellular immunity induction promoter and the like, and satisfactory result is obtained at 0.01 μg to 1 g/kg body weight. The effective amount of a helper peptide can widely vary depending on a specific other ingredient to be used, the quantity thereof and the like, and satisfactory result is obtained at 0.01 μg to 1 g/kg body weight. One day dose may be administered in a single dose or in several divided portions at several times, such as two times or more, for example, two, three, four or five times. The composition may be applied continuously for a period of between 1 minute and 7 days per one administration. The administration interval is appropriately selected from once every day to one year (e.g. once per 1 day, once per 2 days, once per 3 days, once per 1 week, once per 2 weeks, once per 1 month, once per 3 months, once per 6 months, once per 1 year) and longer depending on the state of the patient, severity of the cancer, whether it is for therapeutic purpose or preventive purpose. Generally, for the purpose of treating a patient actually having a severe cancer, the WT1 peptide and/or the modified WT1 peptide are administered at higher frequency and a higher dose, and for the preventive purpose for a patient having no cancer, the WT1 peptide and/or the modified WT1 peptide are administered at lower frequency and a lower dose.

In the present invention, physical irritation means any physical irritation which gives damage to corneum, including scratch and scraping. For example, operation of tape stripping which removes corneum with an adhesive tape or the like, operation of giving damage to the skin with a cutter, and operation using a microneedle such as perforation in corneum with a fine needle are also included in the physical irritation.

Transepidermal water loss means the water amount (g) transpired from 1 $m^2$ of keratin per one hour. Transepidermal water loss can be easily measured with a water loss measuring device in a short time, and is widely used as an index for evaluating the damage degree of the skin. Also in the present invention, transepidermal water loss was used as an index of the physical irritation level.

TSLP (Thymic stromal lymphopoietin) is one of IL-7-like cytokines which is produced from keratinocyte of the skin, thymus, and a mucosal epithelial cells, and is known to be involved in the maturation of dendritic cells, and the differentiation of T cells. In the present invention, TSLP was used as an index of the chemical irritation level which is irritation derived from a drug.

The present invention will be explained in more detail and specifically below by way of Examples. The present invention is not limited to the scope of Examples.

EXAMPLES

Cream Formulation

A cream formulation having ingredients of the following Table 2 was produced. Specifically, Db126 peptide (HLA-A*02 type MHC restricted peptide) or RYF peptide (HLA-A*24 type MHC restricted peptide) or AYL peptide (HLA-A*24 type MHC restricted peptide), cellular immunity induction promoters other than a helper peptide, a helper peptide, a pharmacologically acceptable acid, and optionally, an additive were weighed at the amounts explicitly described in Table 2, 15 parts by weight of DMSO was further blended, and a base (base cream) was added thereto to the total of 100 parts by weight, to obtain a cream formulation. In cream formulations of Examples or Comparative Examples in which the blending amounts are specifically described in Table 2, the blending amounts of respective ingredients were as described in the table.

Each base cream in Table 2 was prepared by blending and kneading materials according to the ratio described in the following Table 1.

TABLE 1

|  | Base cream |
| --- | --- |
| White vaseline | 69.0 wt % |
| Sorbitan monostearate | 0.8 wt % |
| Benzyl alcohol | 2.7 wt % |
| Cetanol | 2.7 wt % |
| Stearyl alcohol | 4.0 wt % |

TABLE 1-continued

| | Base cream |
|---|---|
| Polysorbate 60 | 4.0 wt % |
| Concentrated glycerin | 2.7 wt % |
| Water | 14.1 wt % |

White vaseline, sorbitan monostearate, benzyl alcohol, stearyl alcohol, Polysorbate 60, concentrated glycerin, and dimethyl sulfoxide (DMSO) were purchased from Wako Pure Chemical Industries, Ltd. A TFA salt of Db126 antigen peptide, a TFA salt of RYF peptide, a TFA salt of AYL peptide, an acetic acid salt of Db126 antigen peptide, Peptide-25 (Pep25) and Peptide-25B (Pep25B) were chemically synthesized, purified by HPLC and used. Cetanol, and imiquimod (IMQ) were purchased from Tokyo Chemical Industry Co., Ltd. Cyclic di-GMP (c-di-GMP) and cyclic di-AMP (c-di-AMP) were purchased from Biolog Life Science Institute. Pantoea bacterium-derived lipopolysaccharide manufactured by MACROPHI Inc., $Pam_3CSK_4$ manufactured by InvivoGen, glucopyranosyl lipid manufactured by InvivoGen (MPLAs), Zymosan manufactured by Nacalai Tesque, Inc., Poly(I:C) manufactured by InvivoGen, bropirimine manufactured by TOCRIS bioscience, R848 manufactured by InvivoGen, sodium hyaluronate manufactured by Kikkoman Biochemifa Company (microhyaluronic acid FCH), ODN1826 manufactured by InvivoGen, pidotimod manufactured by Santa Cruz Biotechnology, Inc., bestatin manufactured by Wako Pure Chemical Industries, Ltd., levamisole hydrochloride manufactured by MP Biomedicals, suplatast tosylate manufactured by TOCRIS bioscience, etodolac manufactured by Wako Pure Chemical Industries, Ltd., and loxoprofen Na manufactured by Yoshindo Inc. were respectively used.

The following materials were used.
Imiquimod: Tokyo Chemical Industry Co., Ltd., clofibrate: manufactured by LKT Laboratories, Inc., fenofibrate: manufactured by Wako Pure Chemical Industries, Ltd., quercetin: manufactured by Cayman Chemical Company, berberine (berberine chloride n-hydrate): manufactured by Wako Pure Chemical Industries, Ltd., noscapine: manufactured by Wako Pure Chemical Industries, Ltd., 3,3'-diindolylmethane: manufactured by Wako Pure Chemical Industries, Ltd., xanthone: manufactured by Wako Pure Chemical Industries, Ltd., parthenolide: manufactured by Wako Pure Chemical Industries, Ltd., etodolac: manufactured by Wako Pure Chemical Industries, Ltd., loxoprofen (loxoprofen Na): manufactured by Yoshindo Inc., indomethacin: manufactured by Wako Pure Chemical Industries, Ltd., aspirin: manufactured by Sigma-Aldrich, diclofenac (diclofenac sodium): manufactured by Wako Pure Chemical Industries, Ltd., ketoprofen: manufactured by Wako Pure Chemical Industries, Ltd., celecoxib: manufactured by TOCRIS bioscience, valdecoxib: manufactured by TOCRIS bioscience, docosahexaenoic acid: manufactured by Cayman Chemical Company, 2',5'-dideoxyadenosine: manufactured by BIOMOL International, SCH23390: manufactured by Wako Pure Chemical Industries, Ltd., ropinirole (ropinirole HCl): manufactured by Ragactives, rotigotine: manufactured by STARNASCENS, GW627368X: manufactured by Cayman Chemical Company, sulprostone: manufactured by manufactured by Cayman Chemical Company, cloprostenol: manufactured by Wako Pure Chemical Industries, Ltd., BWA868C: manufactured by Cayman Chemical Company, RO1138452: manufactured by Cayman Chemical Company, leukotriene B4: manufactured by Cayman Chemical Company, montelukast (montelukast sodium): manufactured by LG Life Sciences, zileuton: manufactured by Toronto Research Chemicals, Inc., nicotinic acid: manufactured by Wako Pure Chemical Industries, Ltd., glycyrrhizic acid (dipotassium glycyrrhizinate): manufactured by Wako Pure Chemical Industries, Ltd., pirfenidone: manufactured by TOCRIS bioscience, tranilast: manufactured by Wako Pure Chemical Industries, Ltd., diphenhydramine (diphenhydramine hydrochloride): manufactured by Wako Pure Chemical Industries, Ltd., famotidine: manufactured by Wako Pure Chemical Industries, Ltd., immepip (immepip dihydrobromide): manufactured by TOCRIS bioscience, proxyfan: manufactured by TOCRIS bioscience, azelastine (azelastine hydrochloride): manufactured by LKT Laboratories, Inc., cimetidine: manufactured by Wako Pure Chemical Industries, Ltd., 4-methylhistamine: manufactured by TOCRIS bioscience, olanzapine: manufactured by Wako Pure Chemical Industries, Ltd., yohimbine (yohimbine hydrochloride): manufactured by Wako Pure Chemical Industries, Ltd., acetylcholine (acetylcholine chloride): manufactured by Wako Pure Chemical Industries, Ltd., metergoline (metergoline phenylmethyl ester): manufactured by TOCRIS bioscience, clozapine: manufactured by Wako Pure Chemical Industries, Ltd., sumatriptan: manufactured by MYUNG IN PHARM. CO., LTD., zolmitriptan: manufactured by Cipla, tolvaptan: manufactured by Sigma-Aldrich, desmopressin: manufactured by Sigma-Aldrich, oxybutynin (oxybutynin hydrochloride): manufactured by Sigma-Aldrich, pilocarpine (pilocarpine hydrochloride): manufactured by Wako Pure Chemical Industries, Ltd., tamsulosin (tamsulosin hydrochloride): manufactured by Cipla, midodrine (midodrine hydrochloride): manufactured by Wako Pure Chemical Industries, Ltd., propranolol (propranolol hydrochloride): manufactured by Wako Pure Chemical Industries, Ltd., xylazine: manufactured by Wako Pure Chemical Industries, Ltd., novokinin: manufactured by Sigma-Aldrich, baclofen: manufactured by Tokyo Chemical Industry Co., Ltd., TRAP-6: manufactured by Bachem, adenosine diphosphate: manufactured by MP Biomedicals, somatostatin-14: manufactured by Bachem, GW405833: manufactured by Sigma-Aldrich, SEW2871: manufactured by Cayman Chemical Company, trimebutine (trimebutine maleate): manufactured by Tokyo Chemical Industry Co., Ltd., loperamide (loperamide hydrochloride): manufactured by Wako Pure Chemical Industries, Ltd., melatonin: manufactured by LKT Laboratories, Inc., biphenylindanone A: manufactured by Sigma-Aldrich, L-AP4 (L-2-amino-4-phosphonobutyric acid): manufactured by Wako Pure Chemical Industries, Ltd.

A composite substrate in which a PET film/PET non-woven fabric laminate product (area 0.7 $cm^2$) was stuck to a central portion of an adhesive tape for fixation so that a PET film side was a tape side was prepared. A cream formulation (4 mg) was applied on a non-woven fabric portion of this composite substrate, and this was used as an administration sample of an immunization test.

Mouse Immunization Test 1 (Cream Formulation)

Mouse immunization test was performed with the cream formulations using a model animal for immunological evaluation. Evaluation of the immunity induction level was performed by the ELISPOT method. Specifically, the hair of the back of the mouse was cut. The mouse was kept until it recovered from the skin damage due to the hair cutting. After that, a sample was applied to the back of the mouse for the predetermined time, and then removed. Then, the mouse was kept for predetermined days and the level of the antigen-specific cellular immunity was evaluated. After predetermined days from the application of the sample, the spleen was isolated and a spleen cell suspension was prepared. Spleen cells ($3\times10^6$ cells/well) and the antigen peptide (100 μM) together with the culturing medium were placed into a well of an ELISPOT plate on which an anti-mouse IFN-γ antibody had been immobilized. The plate was cultured for 20 hours under the condition of 37° C. and 5% $CO_2$. The number of the spots representing IFN-γ-producing cells (spot number/$3\times10^6$ cells) was evaluated by the ELISPOT method. In all cases, 4 mg of the cream formulation was applied once for 24 hours and the spleen was isolated 6 days after the completion of the application.

In Example 3, the skin was subjected to tape stripping (TS) ten times using a DUNPLON tape (NITTO DENKO CS SYSTEM CORPORATION, No. 375) before the application of the sample and, in Examples 4 and 5, the skin was injured with a microcutter (MICRO FEATHER No. 7330G, manufactured by FEATHER) and a microneedle (needle length 750 μM, Micro Needle Roller System MR75, manufactured by Ostar Beauty), respectively before the application.

In addition, the cutaneous TSLP level of the mouse after administration, transepidermal water loss of the mouse before administration and the skin permeability of Db126 antigen peptide and imiquimod were also measured in some groups. A mouse used for evaluating the TSLP level, transepidermal water loss, and skin permeability was a C57BL/6 mouse.

(Method of Measuring TSLP Level)

When the application of the sample was completed, the skin of the back of the mouse was isolated, and the skin was ground using a homogenizer (Physcotron, Microtec Co., Ltd.) in an extraction solvent (PBS solution containing protease inhibitor (Protease Inhibitor Cocktail for general use, Sigma-Aldrich) and 10 μM indomethacin (manufactured by Wako Pure Chemical Industries, Ltd.)). The ground skin was centrifuged at 4° C. and 9000 g for 10 minutes, and the supernatant was recovered. The TSLP amount in the supernatant was measured by ELISA (Mouse TSLP Quantikine ELISA Kit, R&D Systems). In addition, the total protein amount in the supernatant was measured by the BCA method (Pierce BCA Protein Assay Kit, Thermo Fisher Scientific K.K.), and the TSLP amount was divided by the total protein amount for standardization.

(Measurement of Transepidermal Water Loss)

Transepidermal water loss was measured using a portable type switching chamber system water loss measuring device (manufactured by Asahibiomed Co., Ltd., VAPO SCAN AS-VT100RS) by contacting a mouse skin with the device for around 5 to 15 seconds. A value which was measured 10 minutes after pre-treatment of a mouse skin was adopted as transepidermal water loss (TEWL) ($g/h \cdot m^2$).

(Mouse Skin Permeability Test)

The skin permeability of Db126 antigen peptide and imiquimod was determined by using a Franz type diffusion cell. A piece of the skin was isolated from the back of a mouse, the hair on which had been cut in advance, was mounted in the Franz-type diffusion cell (application area 4.91 $cm^2$) in which phosphate buffer (pH 7.4 isotonic buffer) at 37° C. was circulated. A 0.7 $cm^2$ preparation was stuck on the mounted skin, and sample in the cell was collected after 24 hours. The collected sample was subjected to high performance liquid chromatograph-tandem mass spectrometer, and the amount of Db126 antigen peptide which had permeated through a skin after 24 hours (Db126 antigen peptide permeated amount, $\mu g/cm^2/24$ hr) and the amount of imiquimod (imiquimod permeated amount, $\mu g/cm^2/24$ hr) were calculated from a pre-determined calibration curve.

The results of the immunization test and the results of measurement of the TSLP level and transepidermal water loss are shown in the following Table 2 together with the mouse strain used in the immunization test. The "genetically modified mouse" in Table 2 is a genetically modified mouse by which cellular immunity induction by a HLA-A*0201 type MHC restrictive peptide can be evaluated. In addition, the results of measurement of skin permeability are shown in Table 3. In addition, for comparison, the results of immunization using an injectable described later (Comparative Examples 4 to 8) are described in an end of the table.

TABLE 2

| | | Composition | | | | | | | Results of immunization (ELISPOT) | |
|---|---|---|---|---|---|---|---|---|---|---|
| | Base | Antigen peptide | Cellular immunity induction promoter | Acid | Additive (Chemical irritation) | TSLP (pg/mg protein) | Physical irritation | TEWL (g/h · m²) | Mouse | average spot number | % Specific Lysis (In vivo CTL assay) |
| Comparative example 1 | base cream | Db126(25) | PEP(0.3) | None | None | | None | 10 | C57BL/6 | 108 | |
| Example 1 | base cream | Db126(25) | IMQ(3) | isostearic acid(8.6) | None | 77 | None | 10 | C57BL/6 | 192 | |
| Example 2 | base cream | Db126(25) | IMQ(3) | isostearic acid(6.2) | SDS(20) | 835 | None | 10 | C57BL/6 | 35 | |
| Example 3 | base cream | Db126(25) | IMQ(3) | isostearic acid(8.6) | None | 54 | TS 10 times | 58 | C57BL/6 | 13 | |
| Example 4 | base cream | Db126(25) | IMQ(3) | isostearic acid(8.6) | None | 42 | microcutter | 66 | C57BL/6 | 8 | |
| Example 5 | base cream | Db126(25) | IMQ(3) | isostearic acid(8.6) | None | 53 | microneedle | 60 | C57BL/6 | 24 | |
| Example 6 | base cream | Db126(25) | c-di-GMP(cyclic dinucleotide) (1) | isostearic acid(8.8) | None | | None | 10 | C57BL/6 | 1209 | 63 |
| Comparative example 2 | base cream | RYf(TFA salt)(4) | IMQ(4) | None | None | | None | 10 | BALB/c | 56 | |
| Example 7 | base cream | RYf(TFA salt)(4) | IMQ(4) | isostearic acid(8.5) | None | 77 | None | 10 | BALB/c | 81 | |
| Comparative example 3 | base cream | AYL(TFA salt)(4) | IMQ(4) | None | None | | None | 10 | BALB/c | 375 | |
| Example 8 | base cream | AYL(TFA salt)(4) | IMQ(4) | isostearic acid(8.5) | None | 78 | None | 10 | BALB/c | 471 | |
| Example 9 | base cream | Db126(25) | c-di-GMP(cyclic dinucleotide) (1) | isostearic acid(8.8) | None | | None | 10 | genetically modified | 1500 | 80 |
| Example 10 | base cream | Db126(25) | c-di-AMP(cyclic dinucleotide) (1) | isostearic acid(8.8) | None | | None | 10 | genetically modified | 1498 | |
| Example 11 | base cream | Db126(25) | Pam3CSK4(TLR1/2 ligand) (1) | isostearic acid(8.8) | None | | None | 10 | genetically modified | 141 | |
| Example 12 | base cream | Db126(25) | Zymosan(ligand for TLR2 and Dectin1) (1) | isostearic acid(8.8) | None | | None | 10 | genetically modified | 152 | |
| Example 13 | base cream | Db126(25) | Poly(I:C) (TLR3 ligand) (1) | isostearic acid(8.8) | None | | None | 10 | genetically modified | 265 | |

TABLE 2-continued

| | | Composition | | | | | | | | Results of immunization (ELISPOT | | |
|---|---|---|---|---|---|---|---|---|---|---|---|---|
| | Base | Antigen peptide | Cellular immunity induction promoter | Acid | Additive (Chemical irritation) | TSLP (pg/mg protein) | Physical irritation | TEWL (g/h·m²) | Mouse | average spot number) | | % Specific Lysis (In vivo CTL assay) |
| Example 14 | base cream | Db126 (25) | lipopolysaccharide derived from Pantoea bacterium(TLR4 ligand) (1) | isostearic acid(8.8) | None | | None | 10 | genetically modified | 173 | | 84 |
| Example 15 | base cream | Db126 (25) | glucopyranosyl lipid(TLR4 ligand) (1) | isostearic acid(8.8) | None | | None | 10 | genetically modified | 207 | | |
| Example 16 | base cream | Db126 (25) | sodium hyaluronate(TLR 4 ligand) (1) | isostearic acid(8.6) | None | | None | 10 | genetically modified | 114 | | |
| Example 17 | base cream | Db126 (25) | IMQ(3) | isostearic acid(8.6) | None | | None | 10 | genetically modified | 342 | | |
| Example 18 | base cream | Db126 (25) | bropirimine(TLR 7 and/or TLR8 ligand) (1) | isostearic acid(8.8) | None | | None | 10 | genetically modified | 267 | | |
| Example 19 | base cream | Db126 (25) | R848(TLR7 and/or TLR8 ligand) (1) | isostearic acid(8.8) | None | | None | 10 | genetically modified | 348 | | |
| Example 20 | base cream | Db126 (25) | ODN1826(TLR9 ligand) (1) | isostearic acid(8.8) | None | | None | 10 | genetically modified | 405 | | |
| Example 21 | base cream | Db126 (25) | pidotimod(immunomodulatory small molecule drug) (1) | isostearic acid(8.8) | None | | None | 10 | genetically modified | 67 | | |
| Example 22 | base cream | Db126 (25) | Bestatin(immunomodulatory small molecule drug) (1) | isostearic acid(8.8) | None | | None | 10 | genetically modified | 96 | | |
| Example 23 | base cream | Db126 (25) | levamisole hydrochloride(immunomodulatory small molecule drug) (1) | isostearic acid(8.8) | None | | None | 10 | genetically modified | 266 | | |
| Example 24 | base cream | Db126 (25) | suplatast tosylate(Th2 cytokine inhibitor)(3) | isostearic acid(8.6) | None | | None | 10 | genetically modified | 159 | | |

TABLE 2-continued

| | Base | Composition | | | Additive (Chemical irritation) | TSLP (pg/mg protein) | Physical irritation | TEWL (g/h·m²) | Mouse | Results of immunization (ELISPOT) average spot number | % Specific Lysis (In vivo CTL assay) |
|---|---|---|---|---|---|---|---|---|---|---|---|
| | | Antigen peptide | Cellular immunity induction promoter | Acid | | | | | | | |
| Example 25 | base cream | Db126 (25) | etodolac(COX inhibitor) (3) | PEP(0.3) | isostearic acid(8.6) | None | | None | 10 | genetically modified | 325 | |
| Example 26 | base cream | Db126 (25) | loxoprofen Na(COX inhibitor) (3) | PEP(0.3) | isostearic acid(8.6) | None | | None | 10 | genetically modified | 352 | |
| Example 27 | base cream | Db126 (25) | clofibrate(PPAR agonist) (3) | PEP(0.3) | isostearic acid(8.6) | None | | None | 12 | genetically modified | 315 | |
| Example 28 | base cream | Db126 (25) | fenofibrate(PPAR agonist) (3) | PEP(0.3) | isostearic acid(8.6) | None | | None | 12 | genetically modified | 237 | |
| Example 29 | base cream | Db126 (25) | quercetin(TSLP production inhibitor) (3) | PEP(0.3) | isostearic acid(8.6) | None | | None | 12 | genetically modified | 156 | |
| Example 30 | base cream | Db126 (25) | berberine(TSLP production inhibitor) (3) | PEP(0.3) | isostearic acid(8.6) | None | | None | 12 | genetically modified | 135 | |
| Example 31 | base cream | Db126 (25) | noscapine(TSLP production inhibitor) (3) | PEP(0.3) | isostearic acid(8.6) | None | | None | 12 | genetically modified | 355 | |
| Example 32 | base cream | Db126 (25) | 3,3'-diindolylmethane (TSLP production inhibitor) (3) | PEP(0.3) | isostearic acid(8.6) | None | | None | 12 | genetically modified | 324 | |
| Example 33 | base cream | Db126 (25) | xanthone(TSLP production inhibitor) (3) | PEP(0.3) | isostearic acid(8.6) | None | | None | 12 | genetically modified | 356 | |
| Example 34 | base cream | Db126 (25) | parthenolide(TSLP production inhibitor) (3) | PEP(0.3) | isostearic acid(8.6) | None | | None | 12 | genetically modified | 305 | |
| Example 35 | base cream | Db126 (25) | indomethacin(COX inhibitor) (3) | PEP(0.3) | isostearic acid(8.6) | None | | None | 12 | genetically modified | 135 | |
| Example 36 | base cream | Db126 (25) | aspirin(COX inhibitor) (3) | PEP(0.3) | isostearic acid(8.6) | None | | None | 12 | genetically modified | 132 | |
| Example 37 | base cream | Db126 (25) | diclofenac(COX inhibitor) (3) | PEP(0.3) | isostearic acid(8.6) | None | | None | 12 | genetically modified | 245 | |
| Example 38 | base cream | Db126 (25) | ketoprofen(COX inhibitor) (3) | PEP(0.3) | isostearic acid(8.6) | None | | None | 12 | genetically modified | 165 | |
| Example 39 | base cream | Db126 (25) | celecoxib(COX inhibitor) (3) | PEP(0.3) | isostearic acid(8.6) | None | | None | 12 | genetically modified | 303 | |
| Example 40 | base cream | Db126 (25) | valdecoxib(COX inhibitor) (3) | PEP(0.3) | isostearic acid(8.6) | None | | None | 12 | genetically modified | 265 | |
| Example 41 | base cream | Db126 (25) | docosahexaenoic acid(omega-3 fatty acid) (3) | PEP(0.3) | isostearic acid(8.6) | None | | None | 12 | genetically modified | 124

TABLE 2-continued

| | Base | Composition | | | | | | | | Results of immunization (ELISPOT average spot number) | % Specific Lysis (In vivo CTL assay) |
|---|---|---|---|---|---|---|---|---|---|---|---|
| | | Antigen peptide | Cellular immunity induction promoter | | Acid | Additive (Chemical irritation) | TSLP (pg/mg protein) | Physical irritation | TEWL (g/h·m²) | Mouse | | |
| Example 42 | base cream | Db126 (25) | 2',5'-dideoxyadenosine (adenylate cyclase inhibitor) (3) | PEP(0.3) | isostearic acid(8.6) | None | | None | 12 | genetically modified | 134 | |
| Example 43 | base cream | Db126 (25) | SCH23390(dopamine receptor antagonist) (3) | PEP(0.3) | isostearic acid(8.6) | None | | None | 12 | genetically modified | 110 | |
| Example 44 | base cream | Db126 (25) | ropinirole(dopamine receptor agonist)(3) | PEP(0.3) | isostearic acid(8.6) | None | | None | 12 | genetically modified | 103 | |
| Example 45 | base cream | Db126 (25) | rotigotine(dopamine receptor agonist) (3) | PEP(0.3) | isostearic acid(8.6) | None | | None | 12 | genetically modified | 205 | |
| Example 46 | base cream | Db126 (25) | GW627368X(prostaglandin receptor antagonist) (3) | PEP(0.3) | isostearic acid(8.6) | None | | None | 12 | genetically modified | 231 | |
| Example 47 | base cream | Db126 (25) | sulprostone (prostaglandin receptor agonist) (3) | PEP(0.3) | isostearic acid(8.6) | None | | None | 12 | genetically modified | 203 | |
| Example 48 | base cream | Db126 (25) | cloprostenol(prostaglandin receptor agonist)(3) | PEP(0.3) | isostearic acid(8.6) | None | | None | 12 | genetically modified | 123 | |
| Example 49 | base cream | Db126 (25) | BWA868C (prostaglandin receptor antagonist) (3) | PEP(0.3) | isostearic acid(8.6) | None | | None | 12 | genetically modified | 132 | |
| Example 50 | base cream | Db126 (25) | RO1138452(prost aglandin receptor antagonist) (3) | PEP(0.3) | isostearic acid(8.6) | None | | None | 12 | genetically modified | 132 | |
| Example 51 | base cream | Db126 (25) | montelukast(leukotriene receptor antagonist) (3) | PEP(0.3) | isostearic acid(8.6) | None | | None | 12 | genetically modified | 132 | |
| Example 52 | base cream | Db126 (25) | leukotriene B4(leukotriene receptor agonist) (3) | PEP(0.3) | isostearic acid(8.6) | None | | None | 12 | genetically modified | 132 | |
| Example 53 | base cream | Db126 (25) | zileuton(leukotriene receptor antagonist) (3) | PEP(0.3) | isostearic acid(8.6) | None | | None | 12 | genetically modified | 132 | |

TABLE 2-continued

| | Base | Composition | | | | | | | Results of immunization (ELISPOT) | |
|---|---|---|---|---|---|---|---|---|---|---|
| | | Antigen peptide | Cellular immunity induction promoter | | Acid | Additive (Chemical irritation) | TSLP (pg/mg protein) | Physical irritation | TEWL (g/h·m²) | Mouse | average spot number | % Specific Lysis (In vivo CTL assay) |
| Example 54 | base cream | Db126 (25) | nicotinic acid(niacin) (adenylate cyclase inhibitor) (3) | PEP(0.3) | isostearic acid(8.6) | None | | None | 12 | genetically modified | 102 | |
| Example 55 | base cream | Db126 (25) | dipotassium glycyrrhizinate (phospholipase A2 inhibitor) (3) | PEP(0.3) | isostearic acid(8.6) | None | | None | 12 | genetically modified | 107 | |
| Example 56 | base cream | Db126 (25) | pirfenidone(TGF-beta production inhibitor) (3) | PEP(0.3) | isostearic acid(8.6) | None | | None | 12 | genetically modified | 197 | |
| Example 57 | base cream | Db126 (25) | tranilast(TGF-beta production inhibitor) (3) | PEP(0.3) | isostearic acid(8.6) | None | | None | 12 | genetically modified | 218 | |
| Example 58 | base cream | Db126 (25) | diphenhydramine (histamine receptor antagonist) (3) | PEP(0.3) | isostearic acid(8.6) | None | | None | 12 | genetically modified | 54 | |
| Example 59 | base cream | Db126 (25) | azelastine(histamine receptor antagonist) (3) | PEP(0.3) | isostearic acid(8.6) | None | | None | 12 | genetically modified | 286 | |
| Example 60 | base cream | Db126 (25) | cimetidine(histamine receptor antagonist) (3) | PEP(0.3) | isostearic acid(8.6) | None | | None | 12 | genetically modified | 187 | |
| Example 61 | base cream | Db126 (25) | famotidine(histamine receptor antagonist) (3) | PEP(0.3) | isostearic acid(8.6) | None | | None | 12 | genetically modified | 187 | |
| Example 62 | base cream | Db126 (25) | proxyfan(histamine receptor agonist) (3) | PEP(0.3) | isostearic acid(8.6) | None | | None | 12 | genetically modified | 189 | |
| Example 63 | base cream | Db126 (25) | 4-methylhistamine (histamine receptor agonist) (3) | PEP(0.3) | isostearic acid(8.6) | None | | None | 12 | genetically modified | 225 | |
| Example 64 | base cream | Db126 (25) | olanzapine(serotonin receptor antagonist) (3) | PEP(0.3) | isostearic acid(8.6) | None | | None | 12 | genetically modified | 235 | |
| Example 65 | base cream | Db126 (25) | yohimbine(serotonin receptor antagonist) (3) | PEP(0.3) | isostearic acid(8.6) | None | | None | 12 | genetically modified | | |

TABLE 2-continued

| | | Composition | | | | | | | | Results of immunization (ELISPOT) | |
|---|---|---|---|---|---|---|---|---|---|---|---|
| | Base | Antigen peptide | Cellular immunity induction promoter | Acid | Additive (Chemical irritation) | TSLP (pg/mg protein) | Physical irritation | TEWL (g/h·m²) | Mouse | average spot number | % Specific Lysis (In vivo CTL assay) |
| Example 66 | base cream | Db126 (25) | acetylcholine(muscarine receptor antagonist)(3) | PEP(0.3) | isostearic acid(8.6) | None | | None | 12 | genetically modified | 102 | |
| Example 67 | base cream | Db126 (25) | metergoline(serotonin receptor antagonist)(3) | PEP(0.3) | isostearic acid(8.6) | None | | None | | genetically modified | | |
| Example 68 | base cream | Db126 (25) | clozapine(serotonin receptor antagonist)(3) | PEP(0.3) | isostearic acid(8.6) | None | | None | 12 | genetically modified | 165 | |
| Example 69 | base cream | Db126 (25) | sumatriptan(serotonin receptor agonist)(3) | PEP(0.3) | isostearic acid(8.6) | None | | None | 12 | genetically modified | 523 | |
| Example 70 | base cream | Db126 (25) | zolmitriptan(serotonin receptor agonist)(3) | PEP(0.3) | isostearic acid(8.6) | None | | None | 12 | genetically modified | 154 | |
| Example 71 | base cream | Db126 (25) | tolvaptan(vasopressin receptor antagonist)(3) | PEP(0.3) | isostearic acid(8.6) | None | | None | 12 | genetically modified | 114 | |
| Example 72 | base cream | Db126 (25) | desmopressin(vasopressin receptor agonist) (3) | PEP(0.3) | isostearic acid(8.6) | None | | None | 12 | genetically modified | 165 | |
| Example 73 | base cream | Db126 (25) | oxybutynin(muscarine receptor antagonist) (3) | PEP(0.3) | isostearic acid(8.6) | None | | None | 12 | genetically modified | 215 | |
| Example 74 | base cream | Db126 (25) | pilocarpine(muscarine receptor agonist) (3) | PEP(0.3) | isostearic acid(8.6) | None | | None | 12 | genetically modified | 134 | |
| Example 75 | base cream | Db126 (25) | tamsulosin(adrenalin receptor antagonist) (3) | PEP(0.3) | isostearic acid(8.6) | None | | None | 12 | genetically modified | 203 | |
| Example 76 | base cream | Db126 (25) | propranolol(adrenalin receptor antagonist) (3) | PEP(0.3) | isostearic acid(8.6) | None | | None | | genetically modified | | |
| Example 77 | base cream | Db126 (25) | xylazine(adrenalin receptor agonist) (3) | PEP(0.3) | isostearic acid(8.6) | None | | None | 12 | genetically modified | 87 | |
| Example 78 | base cream | Db126 (25) | novokinin(angiotensin receptor agonist) (3) | PEP(0.3) | isostearic acid(8.6) | None | | None | | genetically modified | 106 | |
| Example 79 | base cream | Db126 (25) | baclofen(GABA receptor agonist) (3) | PEP(0.3) | isostearic acid(8.6) | None | | None | | genetically modified | 98 | |

TABLE 2-continued

| | Composition | | | | | | | | | Results of immunization (ELISPOT) | |
|---|---|---|---|---|---|---|---|---|---|---|---|
| | Base | Antigen peptide | Cellular immunity induction promoter | | Acid | Additive (Chemical irritation) | TSLP (pg/mg protein) | Physical irritation | TEWL (g/h · m²) | Mouse | average spot number | % Specific Lysis (In vivo CTL assay) |
| Example 80 | base cream | Db126 (25) | TRAP-6(thrombin receptor agonist) (3) | isostearic acid(8.6) | None | | None | 12 | genetically modified mouse | 89 | |
| Example 81 | base cream | Db126 (25) | adenosine diphosphate(ADP receptor agonist) (3) | isostearic acid(8.6) | None | | None | 12 | genetically modified mouse | 95 | |
| Example 82 | base cream | Db126 (25) | somatostatin-14 (somatostatin receptor agonist) (3) | isostearic acid(8.6) | None | | None | 12 | genetically modified mouse | 89 | |
| Example 83 | base cream | Db126 (25) | GW405833 (cannabinoid receptor agonist) (3) | isostearic acid(8.6) | None | | None | 12 | genetically modified mouse | 105 | |
| Example 84 | base cream | Db126 (25) | SEW2871(sphingosine-1 phosphate receptor agonist)(3) | isostearic acid(8.6) | None | | None | 12 | genetically modified mouse | 120 | |
| Example 85 | base cream | Db126 (25) | trimebutine(muscarine receptor antagonist) (3) | isostearic acid(8.6) | None | | None | 12 | genetically modified mouse | 489 | |
| Example 86 | base cream | Db126 (25) | loperamide(opioid receptor agonist) (3) | isostearic acid(8.6) | None | | None | 12 | genetically modified mouse | 234 | |
| Example 87 | base cream | Db126 (25) | melatonin(melatonin receptor agonist) (3) | isostearic acid(8.6) | None | | None | 12 | genetically modified mouse | 204 | |
| Example 88 | base cream | Db126 (25) | biphenylindanone A(metabotropic glutamate receptor agonist) (3) | isostearic acid(8.6) | None | | None | 12 | genetically modified mouse | 165 | |

TABLE 2-continued

| | | Composition | | | | | | | | Results of immunization (ELISPOT | |
|---|---|---|---|---|---|---|---|---|---|---|---|
| | Base | Antigen peptide | Cellular immunity induction promoter | Acid | Additive (Chemical irritation) | TSLP (pg/mg protein) | Physical irritation | TEWL (g/h · m²) | Mouse | average spot number) | % Specific Lysis (In vivo CTL assay) |
| Example 91 | base cream | Db126 (25) | berberine(TSLP production inhibitor) (3), IMQ(3) | isostearic acid(8.6) | None | | None | 12 | genetically modified | 557 | 46 |
| Example 92 | base cream | Db126 (25) | quercetin(TSLP production inhibitor) (3), IMQ(3) | isostearic acid(8.6) | None | | None | 12 | genetically modified mouse | 769 | |
| Comparative example 4 | Saline | Db126 (0.033) | Montanide ISA51VG (50) | None | None | | None | | genetically modified | 33 | |
| Comparative example 5 | Saline | Db126 (0.1) | Montanide ISA51VG (50) | None | None | | None | | genetically modified | 28 | |
| Comparative example 6 | Saline | Db126 (0.33) | Montanide ISA51VG (50) | None | None | | None | | genetically modified | 335 | |
| Comparative example 7 | Saline | Db126(1) | Montanide ISA51VG (50) | None | None | | None | | genetically modified | 347 | |
| Comparative example 8 | Saline | Db126 (3.3) | Montanide ISA51VG (50) | None | None | | None | | genetically modified | 461 | 32 |

IMQ: Imiquimod (TLR7 and/or TLR8 ligand)
c-di-GMP: Cyclic di-GMP (cyclic dinucleotide)
c-di-AMP: Cyclic di-AMP (cyclic dinucleotide)
PEP: Peptide-25 (SEQ ID No.: 7) (helper peptide)
PEPB: Peptide-25B (SEQ ID No.: 11) (helper peptide)
poly(I:C): Polyinosinic-polycytidylic acid (TLR3 ligand)
R848: Resiquimod (TLR7 and/or TLR8 ligand)
SDS: Sodium dodecylsulfate
TS: Tape stripping
Db126 peptide is in a form of an acetic acid salt.
RYF peptide and AYL peptide are in a form of TFA salt.
A numerical value in parenthesis is blending ratio (part(s) by weight) of each ingredient (the same in following Tables).

TABLE 3

| No. | Skin treatment | Permeated Db126 antigen peptide ($\mu g/cm^2/24$ hr) | Permeated Imiquimod ($\mu g/cm^2/24$ hr) |
| --- | --- | --- | --- |
| Example 3 | TS 10 times | 282 | 10 |
| Example 4 | Microcutter | 271 | 11 |
| Example 5 | Microneedle | 179 | 6 |
| Example 1 | None | 35 | 3 |

Tape Preparation

Adhesives for tape preparation were prepared.

(Polymerization of Acrylic Adhesive A)

Under an inert gas atmosphere, 75 parts of 2-ethylhexyl acrylate, 22 parts of N-vinyl-2-pyrrolidone, 3 parts of acrylic acid and 0.2 part of azobisisobutyronitrile were solution polymerized at 60° C. in ethyl acetate to obtain an acrylic adhesive A solution.

(Polymerization of Acrylic Adhesive B)

Under an inert gas atmosphere, 70 parts of 2-ethylhexyl acrylate, 25 parts of N-vinyl-2-pyrrolidone, 5 parts of N-(2-hydroxyethyl)acrylamide and 0.2 part of azobisisobutyronitrile were solution polymerized at 60° C. in ethyl acetate to obtain an acrylic adhesive B solution.

(Preparation of PIB Rubber Adhesive)

In toluene were dissolved 24 parts of polyisobutylene (Oppanol B200, manufactured by BASF), 36 parts of polyisobutylene (Oppanol B12, manufactured by BASF) and 40 parts of an alicyclic petroleum resin (Arkon P-100, manufactured by Arakawa Chemical Industries, Ltd.), to obtain a PIB rubber adhesive solution.

(Preparation of SIS Adhesive A)

In toluene were dissolved 60 parts of a styrene-isoprene-styrene block copolymer (SIS5002, manufactured by JSR Corporation), and 40 parts of an alicyclic petroleum resin (Arkon P-100, manufactured by Arakawa Chemical Industries, Ltd.), to obtain a SIS adhesive A solution.

(Preparation of SIS-PIB Adhesive A)

In toluene were dissolved 30 parts of a styrene-isoprene-styrene block copolymer (SIS5002, manufactured by JSR Corporation), 30 parts of polyisobutylene (Oppanol B100, manufactured by BASF) and 40 parts of an alicyclic petroleum resin (Arkon P-100, manufactured by Arakawa Chemical Industries, Ltd.), to obtain a SIS-PIB adhesive A solution.

Tape preparation shown in the following Table 4 was produced. Specifically, Db126 antigen peptide, a cellular immunity induction promoter, a pharmacologically acceptable acid and, optionally, a skin permeability enhancer, an adhesive solution and an organic solvent (ethyl acetate, ethanol, toluene etc.) in the amounts described in Table 4 were blended, kneaded, and spread on a release liner so that the thickness after drying became about 80 μm, and the organic solvent was removed by drying, and a support was stuck to prepare a tape preparation. The adhesive solution was blended so that the total of respective ingredients and the adhesive after drying the organic solvent became 100 parts by weight. Polyethylene terephthalate (PET) film (thickness 25 μm) was used as the support. Polyethylene terephthalate (PET) sheet (thickness 75 μm) treated with silicone was used as release liner. This tape preparation was cut to give a piece of 0.7 $cm^2$, and was adopted to the immunization test. The release liner was peeled just before the application of the tape preparation.

Sources from which the Db126 antigen peptide, the cellular immunity induction promoter and the pharmacologically acceptable acid were purchased were the same as those in the cream formulation. Isopropyl myristate (IPM) was purchased from Croda Japan. $WT1_{35}$ ($hWT1_{35}$ helper peptide), PADRE (universal helper peptide) and $WT1_{332}$ ($WT1_{332-347}$ helper peptide) were chemically synthesized, and purified by HPLC before use.

Mouse Immunization Test 2 (Tape Preparation)

Using thus obtained tape preparation, mouse immunization test 2 was performed in the same manner as in the mouse immunization test 1. The preparation was applied once for 24 hours/week and a spleen was isolated 6 days after administration. Genetically modified mouse which can be used to evaluate the cellular immunity inducing ability of the HLA-A*0201 type MHC restricted peptide was used as model animal for immunological evaluation.

In Example 69, the skin was injured with a microcutter (MICRO FEATHER No. 7330G, manufactured by FEATHER) before the application of the preparation.

In some groups, the cutaneous TSLP level after the application, transepidermal water loss before the application, and the skin permeability of Db126 antigen peptide and imiquimod were measured in the same manner as conducted in the mouse immunization test 1. The mouse used in evaluation of the TSLP level, transepidermal water loss, and skin permeability was a C57BL/6 mouse.

The results of the immunization test, and the results of measurement of the TSLP level and transepidermal water loss are shown in the following Table 4. In addition, the results of measurement of skin permeability are shown in Table 5.

TABLE 4

| | Base | Antigen peptide | Cellular immunity induction promoter | Skin permeability enhancer | Acid | Additive (Chemical irritation) | TSLP (pg/mg protein) | Physical irritation | TEWL (g/h·m²) | Results of immunization (ELISPOT average spot number) | % Specific Lysis (In vivo CTL assay) |
|---|---|---|---|---|---|---|---|---|---|---|---|
| Comparative example 9 | PIB | Db126(10) | None | | None | None | None | | None | 12 | 3 | |
| Example 93 | PIB | Db126(10) | None | IPM(27) | MA(9) | None | | None | 12 | 10 | |
| Comparative example 10 | PIB | Db126(10) | IMQ(1) | IPM(35.6) | None | None | | None | 12 | 25 | |
| Example 11 | PIB | Db126(10) | None | IPM(35.6) | None | None | | None | 12 | 11 | |
| Comparative example 11 | PIB | Db126(10) | IMQ(1) | IPM(35.2) | None | None | | None | 10 | 40 | |
| Example 12 | PIB | Db126(10) | PEP(1) | IPM(35.6) | MA(8.6) | None | | None | 12 | 18 | |
| Example 94 | PIB | Db126(10) | None | IPM(25.8) | MA(8.6) | None | | None | 10 | 406 | |
| Example 95 | PIB | Db126(10) | IMQ(1) | IPM(25.2) | MA(8.4) | BL-4.2(4) | | None | 10 | 70 | |
| Example 96 | PIB | Db126(10) | IMQ(1) | IPM(25.8) | MA(8.6) | None | | None | 10 | 584 | 35 |
| Example 97 | PIB | Db126(10) | IMQ(3) | IPM(25.8) | MA(8.6) | None | | None | 10 | 1113 | 55 |
| Example 98 | PIB | Db126(10) | WT1₃₅(1) | IPM(25.8) | MA(8.6) | None | | T/S10 | 58 | 56 | |
| Example 99 | PIB | Db126(10) | WT1₃₅(1) | IPM(25.8) | MA(8.6) | None | | None | 10 | 29 | |
| Example 100 | PIB | Db126(10) | IMQ(3) | IPM(26.4) | None | None | | microcutter | 66 | 2 | |
| Comparative example 13 | Acryl A | Db126(10) | None | IPM(26.4) | MA(8.8) | None | | None | 10 | 11 | |
| Example 101 | Acryl A | Db126(10) | IMQ(1) | IPM(26.4) | MA(8.8) | None | | None | 10 | 31 | |
| Example 102 | Acryl A | Db126(10) | IMQ(1) | IPM(26.4) | MA(8.8) | None | | None | 10 | 49 | |
| Example 103 | Acryl A | Db126(10) | PEP(1) | IPM(26.4) | MA(8.8) | None | | None | 10 | 75 | |
| Example 104 | Acryl B | Db126(10) | PEP(1) | IPM(17.4), Liquid paraffin (17.4) | None | None | | None | 10 | 30 | |
| Comparative example 14 | SIS | Db126(10) | IMQ(1) | | | | | | | | |
| Example 105 | SIS | Db126(10) | IMQ(1) | IPM(13.2), Liquid paraffin (13.2) | MA(8.4) | None | | None | 10 | 377 | |
| Comparative example 15 | SIS-PIB | Db126(10) | IMQ(1) | IPM(17.4), Liquid paraffin (17.4) | None | None | | None | 10 | 26 | |
| Example 106 | SIS-PIB | Db126(10) | IMQ(1) | IPM(13.2), Liquid paraffin (13.2) | MA(8.4) | None | | None | 10 | 277 | |
| Example 107 | PIB | Db126(10) | IMQ(3) | IPM(33.0) | octanoic acid(1.7) | None | | None | 10 | 25 | |

TABLE 4-continued

| | Base | Composition | | | | Additive (Chemical irritation) | TSLP (pg/mg protein) | Physical irritation | TEWL (g/h·m²) | Results of immunization (ELISPOT average spot number) | % Specific Lysis (In vivo CTL assay) |
| | | Antigen peptide | Cellular immunity induction promoter | Skin permeability enhancer | Acid | | | | | | |
|---|---|---|---|---|---|---|---|---|---|---|---|
| Example 108 | PIB | Db126(10) | IMQ(3) | IPM(33.0) | isostearic acid(1.7) | None | | None | 10 | 146 | |
| Example 109 | PIB | Db126(10) | IMQ(3) | IPM(25.8) | decanoic acid(8.6) | None | | None | 10 | 375 | |
| Example 110 | PIB | Db126(10) | IMQ(3) | IPM(25.8) | lauric acid(8.6) | None | | None | 10 | 446 | |
| Example 111 | PIB | Db126(10) | IMQ(3) | IPM(25.8) | palmitic acid (8.6) | None | | None | 10 | 40 | |
| Example 112 | PIB | Db126(10) | IMQ(3) | IPM(25.8) | isostearic acid (8.6) | None | | None | 10 | 494 | |
| Example 113 | PIB | Db126(10) | IMQ(3) | IPM(25.8) | oleic acid(8.6) | None | | None | 10 | 495 | |
| Example 114 | PIB | Db126(10) | IMQ(3) | IPM(25.8) | stearic acid (8.6) | None | | None | 10 | 24 | |
| Example 115 | PIB | Db126(10) | IMQ(3) | IPM(31.4) | lactic acid(3) | None | | None | 12 | 501 | |
| Example 116 | PIB | Db126(10) | c-di-GMP (0.3) | IPM(25.8) | MA(8.6) | None | | None | | 450 | |
| Example 117 | PIB | Db126(10) | c-di-AMP (0.3) | IPM(25.8) | MA(8.6) | None | | None | | | |
| Example 118 | PIB | Db126(10) | lipopolysaccharide derived from Pantoea bacterium (TLR4 ligand) (3) | IPM(25.8) | MA(8.6) | None | | None | 12 | 103 | 24 |
| Example 119 | PIB | Db126(10) | glucopyranosyl lipid(TLR4 ligand) (3) | IPM(25.8) | MA(8.6) | None | | None | | | |
| Example 120 | PIB | Db126(10) | sodium hyaluronate (TLR4 ligand) (3) | IPM(25.8) | MA(8.6) | None | | None | | | |
| Example 121 | PIB | Db126(10) | ODN1826(TLR9 ligand) (3) | IPM(25.8) | MA(8.6) | None | | None | | | |
| Example 122 | PIB | Db126(10) | levamisole hydrochloride(immunomodulatory small molecule drug) (3) | IPM(25.8) | MA(8.6) | None | | None | 12 | 45 | |
| Example 123 | PIB | Db126(10) | etodolac(COX inhibitor) (3) | IPM(25.8) | MA(8.6) | None | | None | | | |

TABLE 4-continued

| | | Composition | | | | | | | | Results of immunization (ELISPOT) | |
|---|---|---|---|---|---|---|---|---|---|---|---|
| | Base | Antigen peptide | Cellular immunity induction promoter | Skin permeability enhancer | Acid | Additive (Chemical irritation) | TSLP (pg/mg protein) | Physical irritation | TEWL (g/h · m²) | average spot number | % Specific Lysis (In vivo CTL assay) |
| Example 124 | PIB | Db126(10) | pidotimod(immunomodulatory small molecule drug) (3) | IPM(25.8) | MA(8.6) | None | | None | | | |
| Example 125 | PIB | Db126(10) | Bestatin(immunomodulatory small molecule drug) (3) | IPM(25.8) | MA(8.6) | None | | None | | | |
| Example 126 | PIB | Db126(10) | None | IPM(25.8) | MA(8.6) | None | | None | 10 | 41 | |
| Comparative example 16 | PIB | Db126(10) | loxoprofen Na(COX inhibitor) (3) | IPM(25.8) | None | None | | None | 10 | 185 | 40 |
| Example 127 | PIB | Db126(10) | loxoprofen Na(COX inhibitor) (3) | IPM(25.8) | MA(8.6) | None | | None | 10 | 610 | |
| Example 128 | PIB | Db126(10) | loxoprofen Na(COX inhibitor) (1.5), IMQ(1.5) | IPM(25.8) | MA(8.6) | None | | None | 10 | 736 | 40 |
| Example 129 | PIB | Db126(10) | quercetin(TSLP production inhibitor) (3) | IPM(25.8) | MA(8.6) | None | | None | 12 | 560 | |
| Example 130 | PIB | Db126(10) | quercetin(TSLP production inhibitor) (1.5), IMQ(1.5) | IPM(25.8) | MA(8.6) | None | | None | 12 | 621 | 35 |
| Example 131 | PIB | Db126 (10) | GW62768X(prostaglandin receptor antagonist) (3) | IPM(25.8) | MA(8.6) | None | | None | 12 | 574 | |
| Example 132 | PIB | Db126 (10) | sulprostone (prostaglandin receptor agonist) (3) | IPM(25.8) | MA(8.6) | None | | None | 12 | 530 | |
| Example 133 | PIB | Db126 (10) | clofibrate(PPAR agonist) (3) | IPM(25.8) | MA(8.6) | None | | None | 12 | 610 | |
| Example 134 | PIB | Db126 (10) | tranilast(TGF-beta production inhibitor) (3) | IPM(25.8) | MA(8.6) | None | | None | 12 | 123 | |
| Example 135 | PIB | Db126 (10) | Immepip(histamine receptor agonist) (3) | IPM(25.8) | MA(8.6) | None | | None | 12 | 155 | |
| Example 136 | PIB | Db126 (10) | azelastine(histamine receptor antagonist) (3) | IPM(25.8) | MA(8.6) | None | | None | 12 | 770 | |

TABLE 4-continued

| | Base | Antigen peptide | Cellular immunity induction promoter | Skin permeability enhancer | Acid | Additive (Chemical irritation) | TSLP (pg/mg protein) | Physical irritation | TEWL (g/h·m²) | average spot number | % Specific Lysis (In vivo CTL assay) |
|---|---|---|---|---|---|---|---|---|---|---|---|
| Example 137 | PIB | Db126 (10) | sumatriptan(serotonin receptor agonist) (3) | IPM(25.8) | MA(8.6) | None | | None | 12 | 790 | |
| Example 138 | PIB | Db126 (10) | yohimbine(serotonin receptor antagonist) (3) | IPM(25.8) | MA(8.6) | None | | None | 12 | 173 | |
| Example 139 | PIB | Db126 (10) | oxybutynin(muscarine receptor antagonist) (3) | IPM(25.8) | MA(8.6) | None | | None | 12 | 185 | |
| Example 140 | PIB | Db126 (10) | tamsulosin(adrenalin receptor antagonist) (3) | IPM(25.8) | MA(8.6) | None | | None | 12 | 171 | |
| Example 141 | PIB | Db126 (10) | loperamide (opioid receptor agonist) (3) | IPM(25.8) | MA(8.6) | None | | None | 12 | 480 | |
| Example 142 | PIB | Db126 (10) | melatonin (melatonin receptor agonist) (3) | IPM(25.8) | MA (8.6) | None | | None | 12 | 535 | |
| Example 143 | PIB | Db126 (10) | L-AP4(metabotropic glutamate receptor agonist) (3) | IPM(25.8) | MA(8.6) | None | | None | 12 | 111 | |
| Example 144 | PIB | Db126(10) | PADRE (1) IMQ(3) | IPM(25.8) | MA(8.6) | None | | None | 12 | 613 | |
| Example 145 | PIB | Db126(10) | WT1_332 (1) IMQ(3) | IPM(25.8) | MA(8.6) | None | | None | | | |
| Example 146 | PIB | Db126(10) | PEP(1) IMQ(3) | IPP(25.8) | MA(8.6) | None | | None | 12 | 560 | |
| Example 147 | PIB | Db126(10) | PEP(1) IMQ(3) | None | MA(8.6) | None | | None | 12 | 54 | |
| Comparative example 4 | Saline | Db126 (0.033) | Montanide ISA51VG (50) | None | None | None | | None | | 33 | |
| Comparative example 5 | Saline | Db126 (0.1) | Montanide ISA51VG (50) | None | None | None | None | | 28 | | |
| Comparative example 6 | Saline | Db126 (0.33) | Montanide ISA51VG (50) | None | None | None | None | | 335 | | |
| Comparative example 7 | Saline | Db126(1) | Montanide ISA51VG (50) | None | None | None | None | | 347 | | |

TABLE 4-continued

| | | Composition | | | | | | | Results of immunization (ELISPOT | | |
|---|---|---|---|---|---|---|---|---|---|---|---|
| | Base | Antigen peptide | Cellular immunity induction promoter | Skin permeability enhancer | Acid | Additive (Chemical irritation) | TSLP (pg/mg protein) | Physical irritation | TEWL (g/h·m²) | average spot number) | % Specific Lysis (In vivo CTL assay) |
| Comparative example 8 | Saline | Db126 (3.3) | Montanide ISA51VG (50) | None | None | None | None | | 461 | 32 | |

Acryl A: Acrylic adhesive A
Acryl B: Acrylic adhesive B
PIB: PIB rubber adhesive
SIS: SIS adhesive A
SIS-PIB: SIS-PIB adhesive A
WT1₃₅: hWT1₃₅ helper peptide (SEQ ID No.: 8) (helper peptide)
PADRE: Universal helper peptide (SEQ ID No.: 9) (helper peptide)
WT1₃₃₂: WT1₃₃₂₋₃₄₇ helper peptide (SEQ ID No.: 10) (helper peptide)
IPM: Isopropyl myristate, manufactured by Croda Japan
IPP: Isopropyl palmitate, manufactured by Wako Pure Chemical Industries, Ltd.
MA: Myristic acid
BL-4.2: Polyoxyethylene (4,2) lauryl ether, manufactured by Nikko Chemicals Co., Ltd.
Db126 peptide is in a form of an acetic acid salt, in all cases.
A numerical value in parenthesis is blending ratio (part(s) by weight) of each ingredient.

TABLE 5

| No. | Characteristic | Permeated Db126 antigen peptide ($\mu g/cm^2/24$ hr) | Permeated Imiquimod ($\mu g/cm^2/24$ hr) |
|---|---|---|---|
| Example 95 | Surfactant-free tape | 2.8 | 4.5 |
| Example 96 | BL-4.2 containing tape | 13.4 | 5.8 |

Liquid Formulation for External Use

A liquid formulation for external use having a composition of the following Table 6 was produced. Db126 antigen peptide, a cellular immunity induction promoter and a pharmacologically acceptable acid at the blending amounts described in Table 6, and 15 parts by weight of DMSO were blended, a base was added thereto to the total of 100 parts by weight, and the materials were kneaded to obtain a liquid formulation for external use. Propylene glycol (PG) and oleyl alcohol (OA) were mixed so that the weight ratio became the ratio of 98:2 or 90:10 to give the base. A composite substrate in which a cellulose non-woven fabric portion (area 0.8 cm²) was stuck to a central portion of an adhesive tape for fixation was prepared. The non-woven fabric portion of this composite substrate was impregnated with 67 µL of the prepared liquid formulation for external use, and this was used in the immunization test.

Sources from which the Db126 antigen peptide, the cellular immunity induction promoter and the pharmacologically acceptable acid were purchased were the same as those in the cream formulation. Lactic acid was purchased from Wako Pure Chemical Industries, Ltd.

Mouse Immunization Test 3 (Liquid Formulation for External Use)

Using a liquid formulation for external use produced as described above, mouse immunization test was performed in the same manner as that in the mouse immunization test 1. The dose was 67 µL as described above. The liquid formulation was applied once for 24 hours/week and a spleen was isolated 6 days after completion of the application. The mouse used was a C57BL/6.

In some groups, the cutaneous TSLP level of amuse after the application, and transepidermal water loss of a mouse before the application were measured using a C57BL/6 mouse in the same manner as conducted in the mouse immunization test 1.

The results of the immunization test, the TSLP level and transepidermal water loss are shown in the following Table 6 together with each mouse used.

TABLE 6

| | Composition | | | | TSLP | | | | | Result of immunization (ELISPOT average |
|---|---|---|---|---|---|---|---|---|---|---|
| | Base | Antigen peptide | Cellular immunity induction promoter | Acid | Chemical irritation | (pg/mg protein) | Physical irritation | TEWL (g/h · m²) | Mouse | spot number) |
| Comparative example 17 | PG/OA [98/2] | Db126(10) | IMQ(10) | PEP(0.3) | None | None | 174 | None | 10 | C57BL/6 | 503 |
| Exanple 148 | PG/OA [98/2] | Db126(10) | IMQ(10) | PEP(0.3) | lactic acid(0.5) | None | 185 | None | 10 | C57BL/6 | 595 |
| Example 149 | PG/OA [98/2] | Db126(10) | IMQ(10) | PEP(0.3) | salicylic acid(0.5) | None | | None | 10 | C57BL/6 | 576 |
| Example 150 | PG/OA [98/2] | Db126(10) | IMQ(10) | PEP(0.3) | DL-malic acid(0.5) | None | | None | 10 | C57BL/6 | 520 |
| Example 151 | PG/OA [98/2] | Db126(10) | IMQ(10) | PEP(0.3) | methanesulfonic acid(0.5) | None | | None | 10 | C57BL/6 | 540 |
| Example 152 | PG/OA [98/2] | Db126(10) | IMQ(10) | PEP(0.3) | maleic acid(0.5) | None | | None | 10 | C57BL/6 | 523 |
| Example 153 | PG/OA [98/2] | Db126(10) | IMQ(10) | PEP(0.3) | citric acid(0.5) | None | | None | 10 | C57BL/6 | 552 |
| Comparative example 18 | PG/OA [90/10] | Db126(10) | IMQ(10) | PEP(0.3) | None | Given (Increase in OA ratio) | 270 | None | 10 | C57BL/6 | 435 |
| Example 154 | PG/OA [90/10] | Db126(10) | IMQ(10) | PEP(0.3) | lactic acid(0.5) | Given (Increase in OA ratio) | 313 | None | 10 | C57BL/6 | 515 |

PG/OA: A mixture of propylene glycol and oleyl alcohol (both are manufactured by Wako Pure Chemical Industries, Ltd.). A numerical value in brackets [ ] represents the amount ratio of PG and OA.
A Db126 peptide is in a form of an acetic acid salt.
A numerical value in parenthesis ( ) is blending ratio (part(s) by weight) of each ingredient.

Injectable

Intradermal injectable formulations having a composition of the following Table 7 was produced. Specifically, a saline as a base was added to a Db126 antigen peptide and Montanide ISA51VG (manufactured by Freund Corporation) as an adjuvant at the blending amounts described in Table 7, to the total of 100 parts by weight, and the materials were kneaded with a homogenizer to prepare an injectable.

Mouse Immunization Test 4 (Injectable)

Using an injectable produced as described above, mouse immunization test was performed in the same manner as in the mouse immunization test 1. 30 µL of the injectable formulation was administered once to the back of mouse by intradermal injection, and a spleen was isolated 6 days after the administration. Genetically modified mouse which can be used to evaluate the cellular immunity inducing ability of the HLA-A*0201 type MHC restricted peptide was used as model animal. The results of the immunization test are shown in the following Table 7.

TABLE 7

| | Base | Antigen peptide | Cellular immunity induction promoter | Immunity result (ELISPOT average spot number) | % Specific Lysis (In vivo CTL assay) |
|---|---|---|---|---|---|
| Comparative Example 4 | Saline | Db126(0.033) | Montanide ISA51VG (50) | 33 | |
| Comparative Example 5 | Saline | Db126(0.1) | Montanide ISA51VG (50) | 28 | |
| Comparative Example 6 | Saline | Db126(0.33) | Montanide ISA51VG (50) | 335 | |
| Comparative Example 7 | Saline | Db126(1) | Montanide ISA51VG (50) | 347 | |
| Comparative Example 8 | Saline | Db126(3.3) | Montanide ISA51VG (50) | 461 | 32 |

A Db126 peptide is in a form of an acetic acid salt in all cases. A numerical value in parenthesis is blending ratio (part(s) by weight) of each ingredient.

In Vivo CTL Assay

Seven days after final immunization, the spleen cells (target cell or control cell) were transplanted according to the following procedure, the spleen was isolated after 18 hours. The % Specific Lysis was obtained by performing the FACS measurement.

Procedure 1. Collection of Spleen Cell of Naïve Mouse

Naïve mouse that is the same kind mouse as that used in the immunization test was used. Spleen was isolated from the naïve mouse and mashed using a glass slide in a petri dish containing RPMI1640 medium. The mashed spleen was put into a 50 mL tube and centrifuged at 10° C. and 1100 rpm for 5 minutes. The supernatant was discarded. 20 mL of Lysis Buffer was added to the tube, followed by incubation at room temperature for 5 minutes. 20 mL of the medium was added to the tube and the tube was then centrifuged. The medium was added to the tube and the resultant was passed through a cell strainer to give spleen cell suspension.

Procedure 2. Labeling of Spleen Cell with Antigen

The spleen cells prepared in Procedure 1 were centrifuged at 10° C. and 1100 rpm for 5 minutes, the supernatant was discarded, and HBSS buffer was added to give cell suspension of $2\times10^7$ cells/mL. The cell suspension was dispensed into two 50 mL tubes, 100 μM of the antigen solution (the antigen was the same antigen used in the immunization test) was added to one of the tubes containing the cell solution so that the final concentration became 10 μM, to obtain a target cell. The cell in another tube was adopted as control. The cells in both tubes were incubated at 37° C. for 1 hour, centrifuged, the supernatant was discarded, and a medium was added.

Procedure 3. Labelling of Spleen Cell with CFSE

The cell labelled with the antigen according to the procedure 2 was centrifuged, and 0.1% BSA-PBS was added to $1\times10^7$ cells/mL. To the target cell solution was added a 5 mM CFSE solution to the final concentration of 10 μM, and to the control cell solution was added a 5 mM CFSE solution to the final concentration of 1 μM, and the mixture was vortexed, followed by incubation at 37° C. for 10 minutes. Thereafter, centrifugation was performed, the supernatant was discarded, and a medium was added.

Procedure 4. Transplantation of Spleen Cell

The cell labelled with CFSE according to the procedure 3 was centrifuged, the supernatant was discarded, and cells were adjusted to $5\times10^7$ cells/mL using a HBSS buffer. Equal amounts of the target cell solution and the control cell solution were mixed, and each 200 μL was administered to an immunized mouse via orbital veins (transplantation cell number: $1\times10^7$ cells/animal).

Procedure 5. Preparation of Spleen Cell of Immunized Mouse and Measurement of FACS Eighteen hours after transplantation of the spleen cells, spleen of the mouse was isolated, and spleen cell suspension was prepared in the same manner as in Procedure 1. Thereafter, a CFSE-positive cell was detected by FACS, and the ratio between a CFSE high cell (target cell) and a CFSE low cell (control cell) was obtained. The cytotoxic activity was evaluated by the formula shown below. The obtained value can be used as an index showing the ability of the antigen-specific killer cells induced by the immunization with the vaccine composition to specifically attack the cells that present the antigen in the living body. It was confirmed that the composition of the present invention can induce strong antigen-induced cellular immunity.

$r = (\% \text{ CFSE low cells})/(\% \text{ CFSE high cells})$

% Specific Lysis=$(1-(r_{non\ immunized}/r_{immunized}))\times 100$

By comparison between Comparative Example 1 and Example 1, comparison between Comparative Example 2 and Example 7, comparison between Comparative Example 3 and Example 8, comparison between Comparative Example 12 and Example 95, comparison between Comparative Example 14 and Example 105, comparison between Comparative Example 15 and Example 106, comparison between Comparative Example 16 and Example 127, comparison between Comparative Example 17 and Examples 148-153, and comparison between Comparative Example 18 and Example 154, it is indicated that cellular immunity is induced and promoted by addition of an acid.

Figure 2:
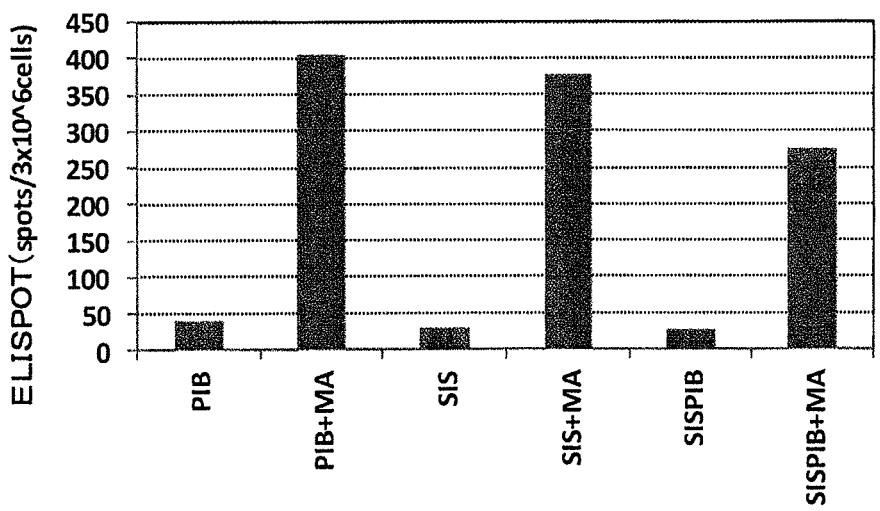
FIG. 2 is a view showing the acid addition effect in various tape preparations.

In addition, it is indicated that cellular immunity was induced in various tape preparations with an acid blended therein (see Table 4 and FIGS. 1 and 2). It is indicated that octanoic acid, isostearic acid, decanoic acid, lauric acid, palmitic acid, isostearic acid, oleic acid, stearic acid and lactic acid are preferable and that strong cellular immunity was induced by blending, particularly, decanoic acid, lauric acid, myristic acid, isostearic acid, oleic acid and lactic acid. Among them, particularly, lauric acid, myristic acid, isostearic acid, oleic acid and lactic acid produced excellent results.

Also in the transdermal immunization using liquid formulation, the addition of an acid promoted the induction of immunity. Lactic acid, salicylic acid, malic acid, methanesulfonic acid, maleic acid, and citric acid were effective. Particularly, lactic acid, salicylic acid, citric acid, and methanesulfonic acid were effective.

Further, it is also indicated that cellular immunity stronger than that by injection was induced (see Tables 4 and 7).

Based on the above results, it was confirmed that a cancer vaccine composition for transdermal administration for cellular immunity induction comprising (i) WT1 peptide and/or modified WT1 peptide and (ii) a pharmacologically acceptable acid or a pharmacologically acceptable salt thereof as a first cellular immunity induction promoter was effective for the induction of cellular immunity.

In addition, from Table 2, Table 4 and Table 6, it is also indicated that cellular immunity is weakened by giving physical damage to a skin by pre-treatment such as tape stripping or skin gash, or by giving chemical irritation to a skin by the use of a surfactant or a specific kind of base material.

Concerning tape preparations in which the kinds of organic fatty acids were different, clear correspondence was not seen between the skin permeation amount and the immunity induction level. In addition, it was confirmed that the skin permeation amount of Db126 and imiquimod was increased by a pre-treatment of a skin.

When compared and checked with the result of an immunity test, it is indicated that TSLP which is an index of skin irritation was increased, and the cellular immunity induction level was reduced by increasing the OA ratio of a PG/OA liquid formulation, or adding a surfactant to a tape. From this result, it is indicated that it is important to induce cellular immunity under the mildly irritating condition.

It is indicated that the TEWL value was increased by pre-treatment of a skin, and skin barrier was destructed by physical irritation. This result corresponds to the fact that the skin permeation amount of Db126 and imiquimod was considerably increased by pre-treatment of a skin, in the skin permeability test. However, in spite of increase in the permeation amount, cellular immunity was not increased, but rather attenuated. From this result, it is indicated that administration under the mildly irritating condition is more important for cellular immunity induction rather than increase in the skin permeation amount of an antigen and an adjuvant.

What is claimed is:

1. A method for inducing cellular immunity in a subject, which comprises transdermally administering to the subject a cancer vaccine composition comprising: (i) a WT1 peptide and/or a modified WT1 peptide; and (ii) a first cellular immunity induction promoter that is a pharmacologically acceptable acid or a pharmacologically acceptable salt thereof, wherein the pharmacologically acceptable acid is selected from the group consisting of isostearic acid, decanoic acid, myristic acid, and malic acid.

2. The method according to claim 1, wherein the method is for treating a cancer in the subject.

3. The method according to claim 1, wherein the cancer vaccine composition further comprises a second cellular immunity induction promoter selected from a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor, and a combination of two or more kinds of them.

4. The method according to claim 3, wherein the second cellular immunity induction promoter is a helper peptide.

5. The method according to claim 3, wherein the second cellular immunity induction promoter is a combination of a helper peptide and at least one substance selected from the group consisting of a TLR ligand, a cyclic dinucleotide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor.

6. The method according to claim 1, wherein the cancer vaccine composition is in the form of a cream formulation.

7. The method according to claim 1, wherein the cancer vaccine composition is in the form of a liquid formulation.

8. The method according to claim 1, wherein the cancer vaccine composition is administered under a mildly irritating condition.

9. The method according to claim 8, wherein the mildly irritating condition is a condition under which transepidermal water loss (TEWL) in a model animal for skin irritation evaluation before the administration of the composition is 50 g/h·m or less.

10. The method according to claim 8, wherein the mildly irritating condition is a condition under which the cutaneous TSLP level in a model animal for skin irritation evaluation at completion of the administration of the composition is 10000 pg/mg protein or less.

11. The method according to claim 1, wherein the pharmacologically acceptable acid or a pharmacologically acceptable salt thereof is isostearic acid.

\* \* \* \* \*